(12) United States Patent
Esposito et al.

(10) Patent No.: US 12,162,855 B2
(45) Date of Patent: Dec. 10, 2024

(54) TETRAHYDROQUINOLINO DERIVATIVES FOR THE TREATMENT OF METASTATIC AND CHEMORESISTANT CANCERS

(71) Applicant: THE TRUSTEES OF PRINCETON UNIVERSITY, Princeton, NJ (US)

(72) Inventors: Mark Esposito, Princeton, NJ (US); Yibin Kang, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 782 days.

(21) Appl. No.: 17/162,827

(22) Filed: Jan. 29, 2021

(65) Prior Publication Data

US 2021/0155602 A1    May 27, 2021

Related U.S. Application Data

(63) Continuation of application No. PCT/US2019/044278, filed on Jul. 31, 2019.

(60) Provisional application No. 62/712,434, filed on Jul. 31, 2018.

(51) Int. Cl.
C07D 401/12    (2006.01)

(52) U.S. Cl.
CPC ................. C07D 401/12 (2013.01)

(58) Field of Classification Search
CPC .................................. C07D 401/12
USPC ........................................ 514/336
See application file for complete search history.

(56) References Cited

U.S. PATENT DOCUMENTS

| | | | |
|---|---|---|---|
| 4,593,035 A * | 6/1986 | Tominaga | C07D 407/12 514/312 |
| 4,954,498 A | 9/1990 | Mertens et al. | |
| 10,752,640 B2 | 8/2020 | Seitzberg et al. | |
| 2005/0239825 A1 | 10/2005 | Heise et al. | |
| 2011/0112067 A1 | 5/2011 | Hartmann et al. | |
| 2017/0057982 A1 | 3/2017 | Yang et al. | |
| 2017/0182009 A1 | 6/2017 | Piomelli et al. | |
| 2023/0128402 A1 | 4/2023 | Esposito et al. | |

FOREIGN PATENT DOCUMENTS

| | | |
|---|---|---|
| CN | 106573915 | 4/2017 |
| JP | S61145162 | 7/1986 |
| JP | S63192773 | 8/1988 |
| JP | 1989319453 | 12/1989 |
| JP | 2006349902 | 12/2006 |
| WO | 2004099146 | 11/2004 |
| WO | 2005046589 | 5/2005 |
| WO | 2013027168 | 2/2013 |
| WO | 2015/127137 | 8/2015 |
| WO | 2016/016316 | 2/2016 |
| WO | 2020/028461 A1 | 2/2020 |
| WO | 2021151062 | 7/2021 |
| WO | 2022123039 | 6/2022 |
| WO | 2022226383 | 10/2022 |

OTHER PUBLICATIONS

Database Registry XP002795180, dated Oct. 22, 2019, 1 page.
Database Registry XP002795181, dated Nov. 15, 2019, 1 page.
Database Registry XP002795170, dated Oct. 22, 2019, 1 page.
Database Registry XP002795737, dated Nov. 15, 2019, 2 pages.
Database Registry XP002795172, dated Oct. 22, 2019, 1 page.
Database Registry XP002795171, dated Oct. 22, 2019, 1 page.
Database Registry XP002795173, dated Oct. 22, 2019, 1 page.
Database Registry XP002795174, dated Oct. 22, 2019, 1 page.
Database Registry XP002795178, dated Oct. 22, 2019, 1 page.
Database Registry XP002795179, dated Oct. 22, 2019, 1 page.
Henry et al., "One-pot ortho-amination of aryl C—H bonds using consecutive iron and copper catalysis", XP-002795169 Organic & Biomolecular Chemistry, Royal Society of Chemistry, Org. Biomol. Chem., 2019, 17, 4629, 11 pgs.
Joshi et al., "Identification of Potent and Selective CYP1A1 Inhibitors via Combined Ligand and Stracture-Based Virtual Screening and Their in Vitro Validation in Sacchrosomes and Live Human Cells", Chemical Information and Modeling, 2017, v.57, 12 pages.
Vasiliou Vasilis et al: "Aldehyde dehydrogenases: From eye crystallins to metabolic disease and cancer stem cells", Chemico-Biological Interactions, Elsevier Science Irland, IR, vol. 202, No. 1, Nov. 16, 2012 (Nov. 16, 2012), pp. 2-10, XP028995541, ISSN: 0009-2797, DOI: 10.1016/J.CBI. 2012.10.026.
Database Caplus (STN) [Online] Jan. 1, 2006 (Jan. 1, 2006), Nakagawa Nhajime N H: "Black and white heat-developable photographic material", XP093055941, Database accession No. 2006:1351625-rn: 917242-17-2.
Lack Nathan A. et al: "Targeting the Binding Function 3 (BF3) Site of the Human Androgen Receptor through Virtual Screening.", Journal of Medicinal Chemistry, vol. 54, No. 24, Nov. 18, 2011 (Nov. 18, 2011), pp. 8563-8573, XP093055950, US ISSN: 0022-2623, DOI: 10.1021/jm201098n; compound with rn: 921999-77-1.

(Continued)

Primary Examiner — Kristin A Vajda
(74) Attorney, Agent, or Firm — NIXON & VANDERHYE, PC

(57) ABSTRACT

Disclosed herein are compounds of Structural Formula I. Compounds of Structural Formula I inhibit aldehyde dehydrogenase isoform Ia3 (ALDHIa3) and are useful for treating cancer, for example, metastatic or chemoresistant cancer, such as metastatic cancer resistant to chemotherapy. Also disclosed herein are compositions comprising compounds of Structural Formula I and uses of compounds of Structural Formula I for treating cancer, for example, metastatic or chemoresistant cancer.

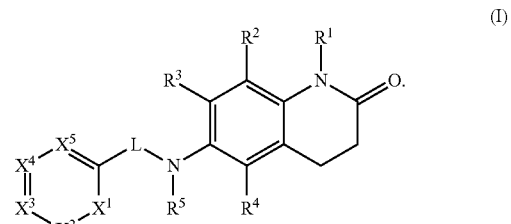

(I)

2 Claims, 33 Drawing Sheets

(56) References Cited

OTHER PUBLICATIONS

Database STN [Online] Jan. 1, 1990 (Jan. 1, 1990), Yoshizawa Toyokichi N C: "Preparation of heterocyclyl-substituted benzoquinone derivatives as drugs", XP093055964, Database accession No. 113:5936; compound with rn: 127430-92-6.
Database Caplus [Online] STN; Jan. 1, 1988 (Jan. 1, 1988), Der Saal Alfred ; et al: "Preparation of heterocyclobenzimidazoles as cardiovascular agents", XP093055966, Database accession No. 1988:590420; rn: 117242-02-1.
Database Caplus [Online] STN; Jan. 1, 1976 (Jan. 1, 1976), Nakagawa Kazuyuki: "Carbostyril derivatives", XP093055968, Database accession No. 1977:468181; rn:63430-44-4.
STN International Registry 2217474-28-5/RN; Oct. 11, 2023, 34 pages.
Database Registry Chemical Abstracts Service, Columbus, Ohio, US; Jun. 6, 2011 (Jun. 6, 2011), XP002795177, Database accession No. 1306404-60-3 rn: 1306404-60-3 Supplier: Ryan Scientific, Inc.
Database Registry Chemical Abstracts Service, Columbus, Ohio, US; Jun. 10, 2011 (Jun. 10, 2011), XP002795176, Database accession No. 1308446-19-6 rn: 1308446-19-6 Supplier: Ryan Scientific, Inc.
Database Registry Chemical Abstracts Service, Columbus, Ohio, US; Nov. 3, 2013 (Nov. 3, 2013), XP002795175, Database accession No. 1468571-74-5 rn: 1468571-74-5 Supplier: Aurora Fine Chemicals.
Buchman, C.D., et al., "Discovery of a series of aromatic lactones as ALDH1/2-directed inhibitors", Chem Biol Interact, 2015, 234, 38-44.
Chefetz, I., "A Pan-ALDH1A Inhibitor Induces Necroptosis in Ovarian Cancer Stem-Like Cells", Cell Rep. 2019, 26, 3061-3075.
Yasgar, A. et al., "A High-Content Assay Enables the Automated Screening and Identification of Small Molecules and Specific ALDH1A1-Inhibitory Activity", PLoS one, 2017, 12, e0170937, 1-19.
Database Registry Chemical Abstracts Service, Columbus, Ohio, US, Database accession No. 1152985-39-1, entered Jun. 7, 2009, Supplier: UkrOrgSynthesis, 1 page.
Database Registry Chemical Abstracts Service, Columbus, Ohio, US, Database accession No. 1154533-39-7, entered Jun. 9, 2009, Supplier: UkrOrgSynthesis, 1 page.
Huddle, B.C., "Structure-Based Optimization of a Novel Class of Aldehyde Dehydrogenase 1A (ALDH1A) Subfamily-Selective Inhibitors as Potential Adjuncts to Ovarian Cancer Chemotherapy," J. Med. Chem., 2018, 61, 8754-8773.
International Preliminary Report on Patentability for International Application No. PCT/US2022/026059 dated Nov. 2, 2023, 7 pages.
International Search Report and Written Opinion for International Application No. PCT/US2022/026059 dated Sep. 9, 2022, 14 Pages.
International Search Report and Written Opinion issued in PCT/US2021/014883, mailed Jun. 3, 2021, 9 pages.
International Search Report and Written Opinion for PCT Application No. PCT/US2019/044278 mailed on Nov. 27, 2019, 14 pages.
Jimenez, R., "Inhibitors of aldehyde dehydrogenases of the 1A subfamily as putative anticancer agents: Kinetic characterization and effect on human cancer cells," Chem. Biol. Interact. 2019, 306, 123-130.
Khanna, M. et al., "Discovery of a Novel Class of Covalent Inhibitors for Aldehyde Dehydrogenases", J. Biol. Chem., Dec. 16, 2011, 286(50): 43486-43494.
Kimble-Hill, A.C., "Development of selective inhibitors for aldehyde dehydrogenases based on substituted indole-2,3-diones", J. Med. Chem., 2014, 57, 714-722.
Koppaka, V. et al., "Aldehyde dehydrogenase inhibitors: a comprehensive review of the pharmacology, mechanism of action, substrate specificity, and clinical application", Pharmacol. Rev., 2012, 64, 520-539.

Yoshizawa Toyokichi NC: "Preparation of heterocyclyl-substituted benzoquinone derivatives as drugs", Database STN [Online] Jan. 1, 1990 (Jan. 1, 1990), Database accession No. 113:5936; compound with rn: 127430-92-6, 2 pages.
Li, D. et al., "Abstract 17192: ALDH1A3 Induces NFY to Coordinate Transcription of Cell Cycle and Metabolic Genes Necessary for Smooth Muscle Proliferation in Pulmonary Hypertension", Circulation, 2018, 138(Supp. 1) (abstract), 1 page.
Liang, D. et al., "Discovery of coumarin-based selective aldehyde dehydrogenase 1A1 inhibitors with glucose metabolism improving activity", Eur. J. Med. Chem, 2020, 187, 111923.
Mertens—Database Caplus [Online] STN; Jan. 1, 1988 (Jan. 1, 1988), Der Saal Alfred, et al., "Preparation of heterocyclobenzimidazoles as cardiovascular agents", Database accession No. 1988:590420; rn: 117242-02-1.
Morgan, C.A. et al., "Characterization of two distinct structural classes of selective aldehyde dehydrogenase 1A1 inhibitors", J. Med. Chem. 2015, 58, 1964-1975.
Nakagawa Nhajime N H, "Black and white heat-developable photographic material", Database Caplus (STN) [Online] Jan. 1, 2006, Database accession No. 2006:1351625-rn: 917242-17-2, 1 page.
Office Action for Japanese Application No. JP20210505202 dated Aug. 17, 2023, 5 pages, with English translation.
Pubchem 165301313, modified Feb. 4, 2023, created Oct. 10, 2022, 7 pages.
Pubchem, SID 322785251, available and deposit Jan. 24, 2017, 7 pages.
Pubchem, SID 403637055, available and deposit Jan. 24, 2020, 5 pages.
Registry (STN) [online] [date-of-search Jun. 14, 2023] CAS Registration No. 1788963-83-6, entered Jun. 26, 2015, Supplier: Aurora Fine Chemicals, 3 pages.
Xie, X. et al. "ALDH1A3 Regulations of Matricellular Proteins Promote Vascular Smooth Muscle Cell Proliferation", iScience, 2019, 19: 872-882.
Yang, S.M., "Discovery of Orally Bioavailable, Quinoline-Based Aldehyde Dehydrogenase 1A1 (ALDH1A1) Inhibitors with Potent Cellular Activity", J. Med. Chem, 2018, 61, 4883-4903.
International Search Report for PCT/US2019/044278 dated Nov. 27, 2019, 7 pages.
Invitation to Pay Additional fees received for International Application No. PCT/US2023/077659, mailed Jan. 17, 2024. 2 pages.
International Search Report and Written Opinion for International Application No. PCT/US2023/077659, mailed Mar. 1, 2024, 13 pages.
Database Registry Chemical Abstracts Service, Columbus, Ohio, US, Database accession No. 1153283-51-2, entered Jun. 7, 2009, Supplier: UkrOrgSynthesis, 1 page.
Database Registry Chemical Abstracts Service, Columbus, Ohio, US, Database accession No. 1153283-98-7, Supplier: UkrOrgSynthesis, entered Jun. 7, 2009, 1 page.
Database Registry Chemical Abstracts Service, Columbus, Ohio, US, Database accession No. 1153284-52-6, entered Jun. 7, 2009, Supplier: UkrOrgSynthesis, 1 page.
Database Registry Chemical Abstracts Service, Columbus, Ohio, US, Database accession No. 1153285-10-9, entered Jun. 7, 2009, Supplier: UkrOrgSynthesis, 1 page.
Database Registry Chemical Abstracts Service, Columbus, Ohio, US, Database accession No. 1303823-01-9 rn: 1303823-01-9, entered Jun. 1, 2011, Supplier: Ryan Scientific, Inc., 1 page.
Database Registry Chemical Abstracts Service, Columbus, Ohio, US; Database accession No. 1874534-18-5 rn: 1874534-18-5, entered Feb. 26, 2016, Supplier: Ukrorgsyntez Ltd., 1 page.
Database Registry Chemical Abstracts Service, Columbus, Ohio, US, Database accession No. 2094147-63-2, entered May 2, 2017, Supplier: Enamine LLC, 1 page.
Dorwald, F. Zaragoza. Side Reactions in Organic Synthesis: A Guide to Successful Synthesis Design, Weinheim: Wiley-VCH Verlag GmbH & Co. KGaA, 2005, Preface. 4 printed pages.
Extended European Search report for Application No. 21744411.6, dated Feb. 8, 2024, 9 pages.
Jordan, "Tamoxifen: a most unlikely pioneering medicine", Nat Rev Drug Discov. Mar. 2003; 2(3): 205-13.

(56) References Cited

OTHER PUBLICATIONS

PubChem SID 164995132, Source: Life Chemicals, available date Nov. 14, 2013, 5 pages.
PubChem SID 228844606, Source: SureChEMBL, available date Feb. 12, 2015, 5 pages.
PubChem SID 355035722, Source: Fisher Drug Discovery Resource Center, available date Mar. 12, 2018, 5 pages.
Pubchem, SID 464908864, Modify Date: Jun. 23, 2022 [retrieved on Mar. 4, 2024], Retrieved from the Internet <URL: https://pubchem.ncbi.nlm.nih.gov/ substance/464908864>, 5 pages.
STN Database Registry accession No. 635674-82-7/RN, pp. 1-5, Jul. 9, 2015.
UniProtKB Accession No. P47895, "AL1A3_HUMAN", integrated into UniProtKB/Swiss-Prot., Feb. 1, 1996. Available at: https://www.uniprot.org/uniprotkb/P47895/entry, retrieved on Feb. 13, 2024. 10 printed pages.
Wilen et al., "Strategies in optical resolutions," Tetrahedron, vol. 33, Issue 21, 1977, pp. 2725-2736.
Wilen, S. H., "Tables of Resolving Agents and Optical Resolutions", p. 268, E.L. Eliel, Ed., Univ. of Notre Dame Press, Notre Dame, IN, (1972), 31 printed pages.
Zhao, L. et al., "Huaxue Shiji", 2005, v.27, pp. 95-96.
Zhao, L. et al., "Huaxue Shiji" 2003, v.25, pp. 222-224.
Japanese Office Action in corresponding JP Application No. JP2021-505202 dated Jun. 6, 2024, 4 pages.

* cited by examiner

TETRAHYDROQUINOLINO DERIVATIVES FOR THE TREATMENT OF METASTATIC AND CHEMORESISTANT CANCERS

RELATED APPLICATIONS

This application is a continuation application of International Application No. PCT/US2019/044278 filed Jul. 31, 2019 which designated the U.S. and claims priority to U.S. Provisional Patent Application No. 62/712,434 filed Jul. 31, 2019, the entire contents of each of which are hereby incorporated by reference.

BACKGROUND

Current therapies for treating aggressive and/or chemoresistant metastatic cancers have limited efficacy. Accordingly, there is a need for therapeutic agents having improved efficacy for the treatment of these cancers.

SUMMARY

Provided herein are compounds, compositions and methods for treating cancers, for example, metastatic cancers (e.g., a metastatic breast cancer, such as a basal-like breast cancer, a HER-2 positive breast cancer), chemoresistant cancers (e.g., cancers resistant to paclitaxel and/or doxorubicin) in a subject in need thereof.

One embodiment is a compound of Structural Formula II:

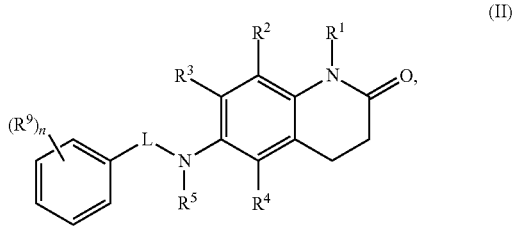

(II)

or a pharmaceutically acceptable salt thereof, wherein values for the variables (e.g., $R^1$, $R^2$, $R^3$, $R^4$, $R^5$, $R^9$, L, n) are as described herein.

Another embodiment is a method of treating a metastatic or chemoresistant cancer in a subject in need thereof, comprising administering to the subject a compound of Structural Formula I:

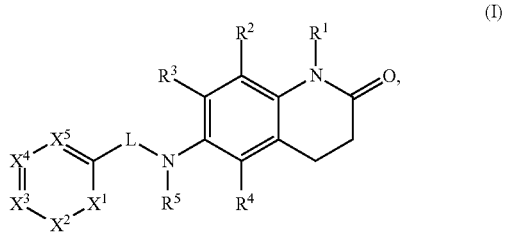

(I)

or a pharmaceutically acceptable salt thereof, wherein values for the variables (e.g., $R^1$, $R^2$, $R^3$, $R^4$, $R^5$, $R^9$, L, $X^1$, $X^2$, $X^3$, $X^4$, $X^5$) are as described herein. Also provided is a compound for use in the treatment of a metastatic or chemoresistant cancer, wherein the compound is represented by Structural Formula I, or a pharmaceutically acceptable salt thereof. Also provided is use of a compound of Structural Formula I, or a pharmaceutically acceptable salt thereof, for the manufacture of a medicament for the treatment of a metastatic or chemoresistant cancer.

Yet another embodiment is a method of inhibiting the proliferation of a metastatic or chemoresistant cancer cell, comprising administering to the cell an effective amount of a compound of Structural Formula I, or a pharmaceutically acceptable salt thereof. Also provided is a compound for inhibiting the proliferation of a metastatic or chemoresistant cancer cell, wherein the compound is represented by Structural Formula I, or a pharmaceutically acceptable salt thereof. Also provided is use of a compound of Structural Formula I, or a pharmaceutically acceptable salt thereof, for the manufacture of a medicament for inhibiting the proliferation of a metastatic or chemoresistant cancer cell.

Another embodiment is a method of treating type 2 diabetes in a subject in need thereof, comprising administering to the subject a compound of Structural Formula I, or a pharmaceutically acceptable salt thereof. Also provided is a compound for use in the treatment of type 2 diabetes, wherein the compound is represented by Structural Formula I, or a pharmaceutically acceptable salt thereof. Also provided is use of a compound of Structural Formula I, or a pharmaceutically acceptable salt thereof, for the manufacture of a medicament for the treatment of type 2 diabetes.

The compounds, compositions and methods described herein can be used to inhibit an enzymatic target (ALDH1a3) that is important for metastasis and/or resistance to chemotherapy, and is broadly expressed in many tumor types. Many of the compounds described herein possess low nanomolar affinity for ALDH1a3, and Compound MBE1 has been shown to shrink metastatic lesions in mice without toxicity.

BRIEF DESCRIPTION OF THE DRAWINGS

The foregoing will be apparent from the following more particular description of example embodiments.

dataset, and shows the survival time of breast cancer patients by subtype and stratification by median ALDH1a3 expression level.

Figure 12:
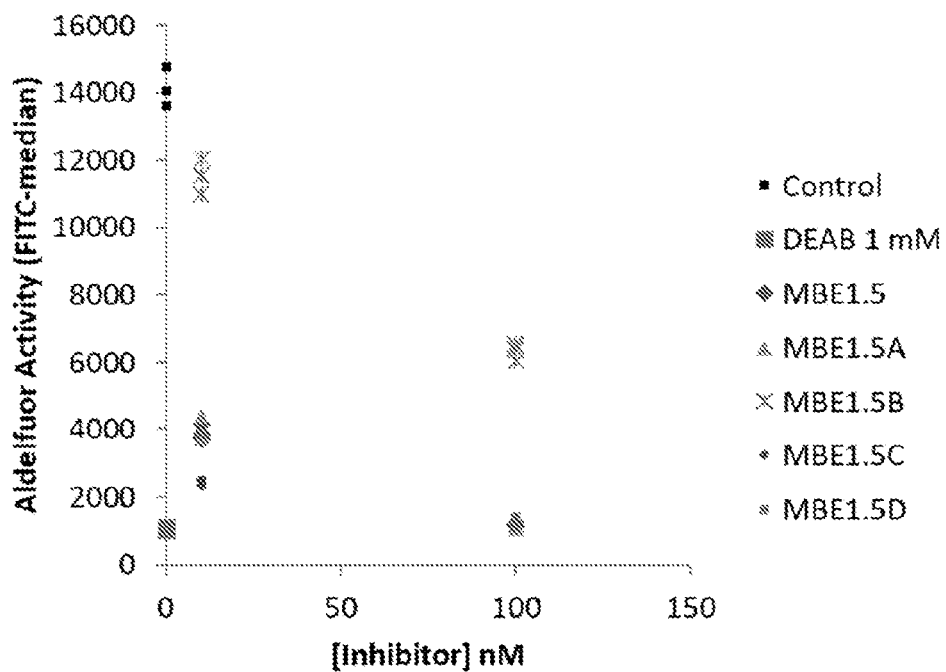

FIG. 12 is a graph of ALDEFLUOR™ activity versus concentration, and shows the ALDEFLUOR™ activity of several compounds described herein at concentrations of 10 nM and 100 nM.

Figure 13A:
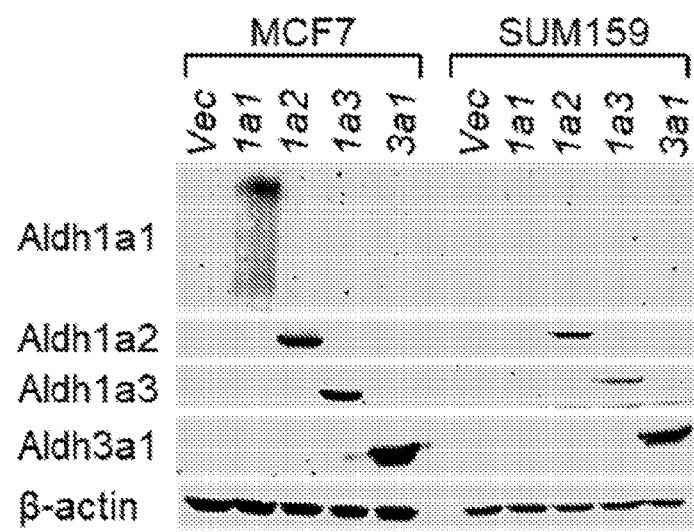

FIG. 13A is a Western blot, and shows the expression of various ALDH isoforms, including 1a1, 1a2, 1a3 and 3a1, in MCF7 and SUM 159 cells.

Figure 13B:
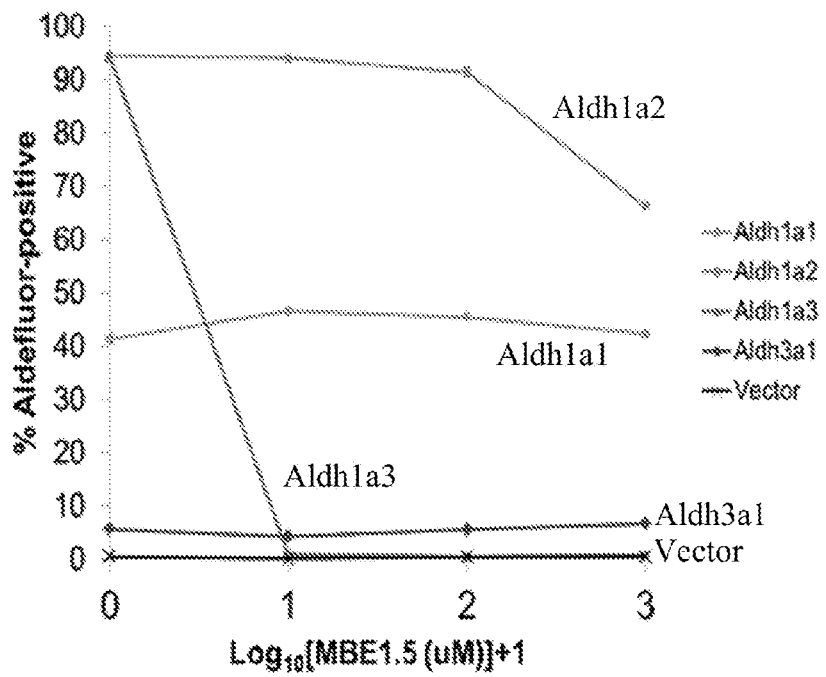

FIG. 13B is a line graph of percentage of ALDE-FLUOR™-positive MCF7 cells expressing the indicated ALDH isoform versus the log of MBE 1.5 concentration, and shows that MBE 1.5 specifically inhibits ALDH1a3 at concentrations below 10 μM.

Figure 13C:
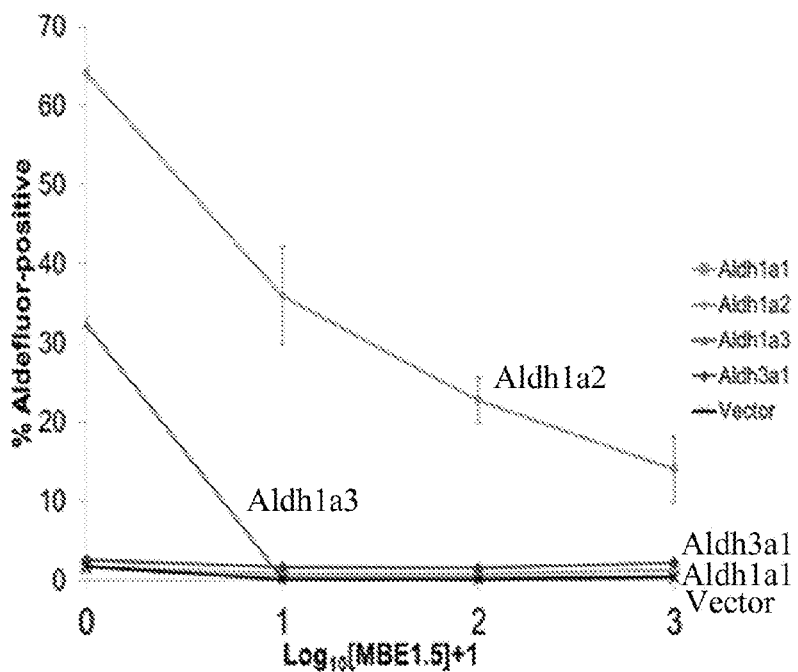

FIG. 13C is a line graph of percentage of ALDE-FLUOR™-positive SUM159 cells expressing the indicated ALDH isoform versus the log of MBE 1.5 concentration, and shows that MBE 1.5 specifically inhibits ALDH1a3 at concentrations below 10 μM.

Figure 14:
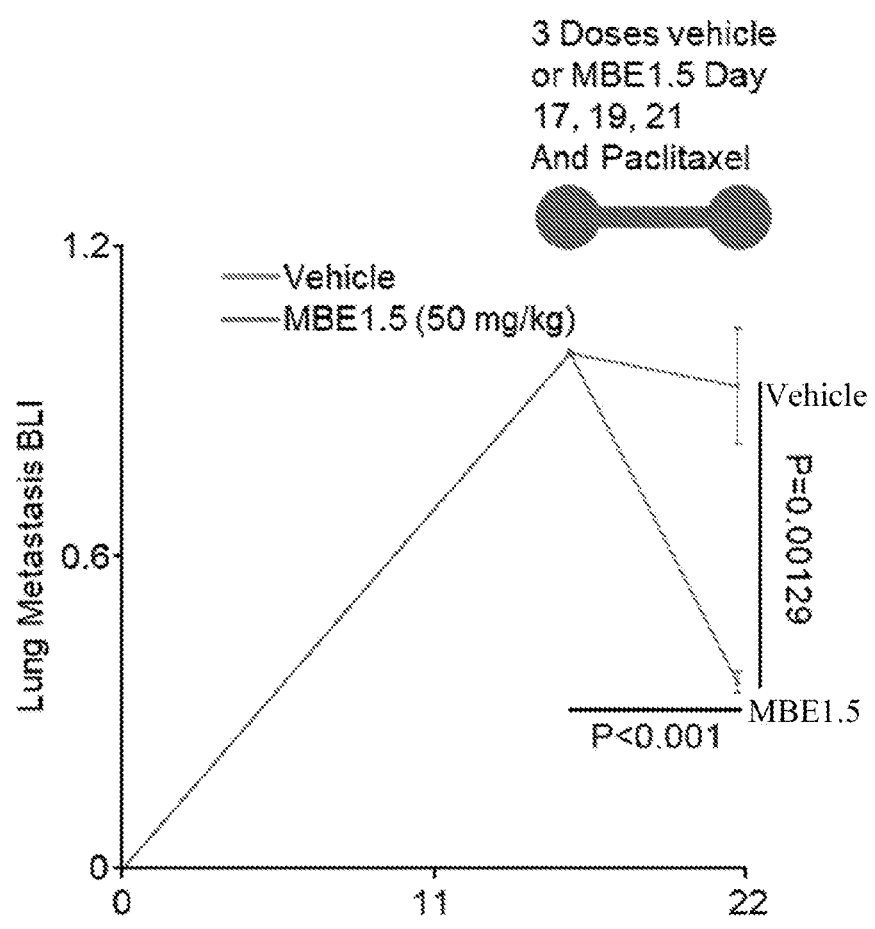

FIG. 14 is a line graph of lung metastasis, as measured by bioluminescent imaging (BLI), versus time (days), and shows that three doses of 50 mg/kg MBE1.5 in combination with 25 mg/kg paclitaxel, administered on days 17, 19 and 21 caused regression of established metastatic disease in a mouse xenograft model. Student's t-test, two-tailed, assuming unequal variance.

Figure 15A:
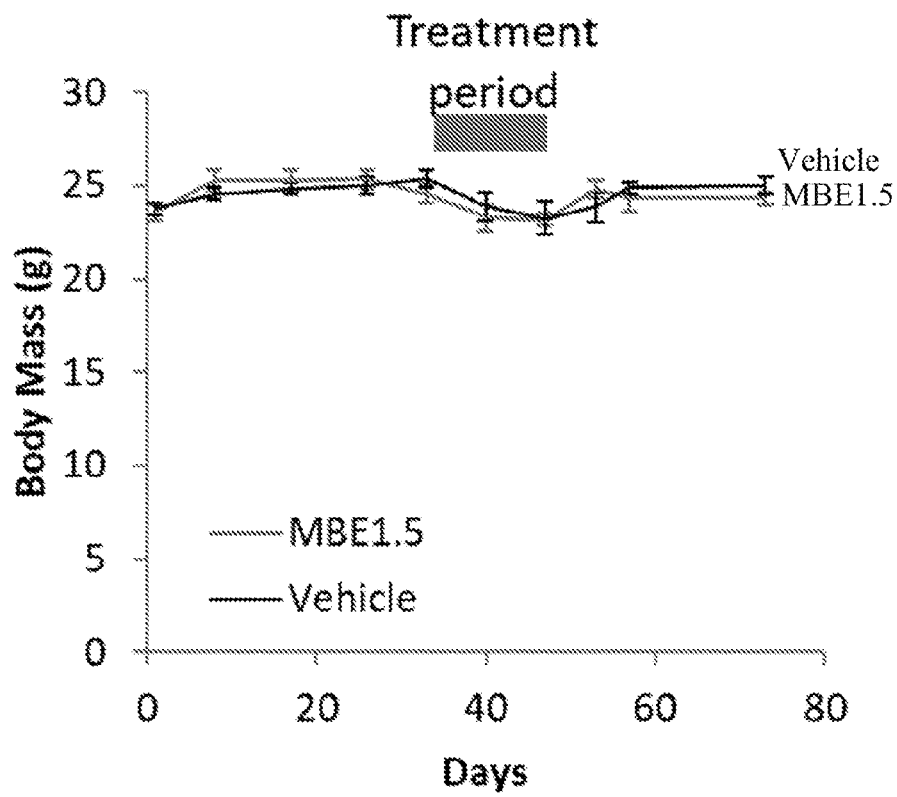

FIG. 15A is a line graph of body mass (g) versus time (days), and shows that there was no gross toxicity associated with MBE1.5 treatment in this experiment.

Figure 15B:
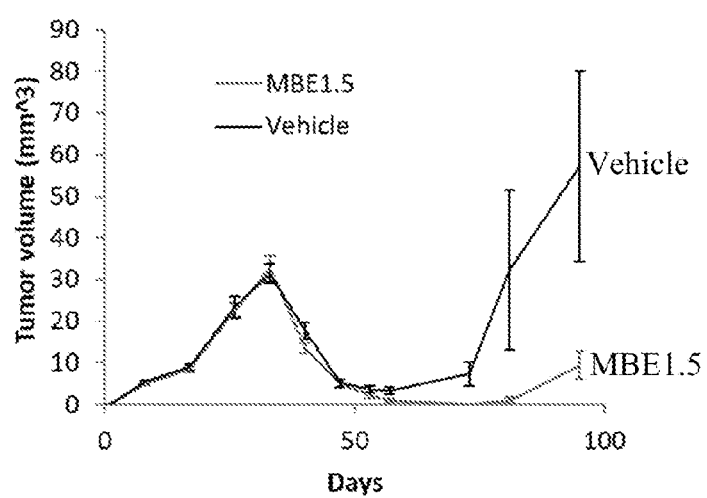

FIG. 15B is a line graph of tumor volume (mm$^3$) versus time (days), and shows that 12-day treatment with MBE1.5 caused regression of MDA-MB-468 primary breast tumors. Statistics by Student's t-test. *$p<0.05$.

Figure 16A:
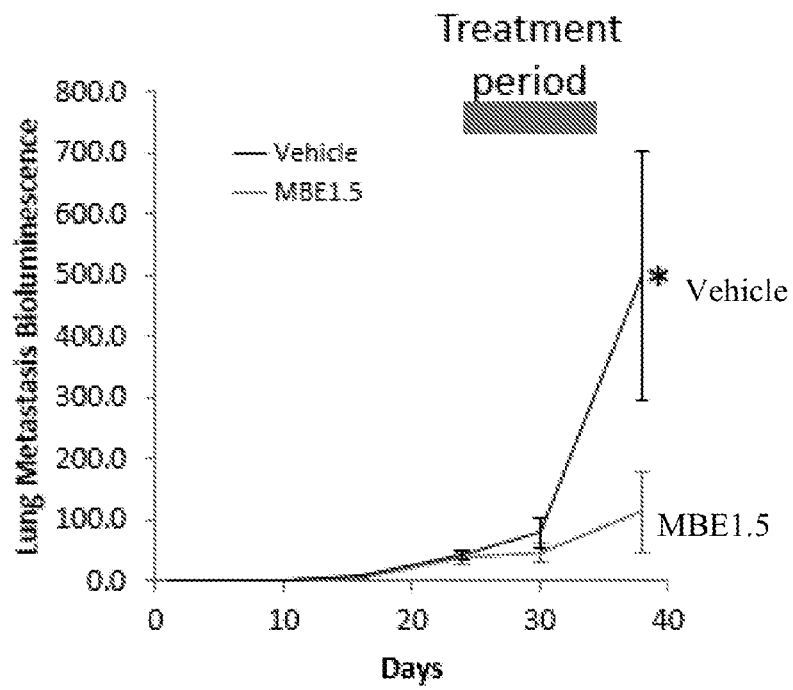

FIG. 16A is a line graph of lung metastasis bioluminescence versus time (days), and shows the progression of lung metastasis before and after treatment with MBE1.5 or vehicle. Statistics by Student's t-test. *$p<0.05$.

Figure 16B:
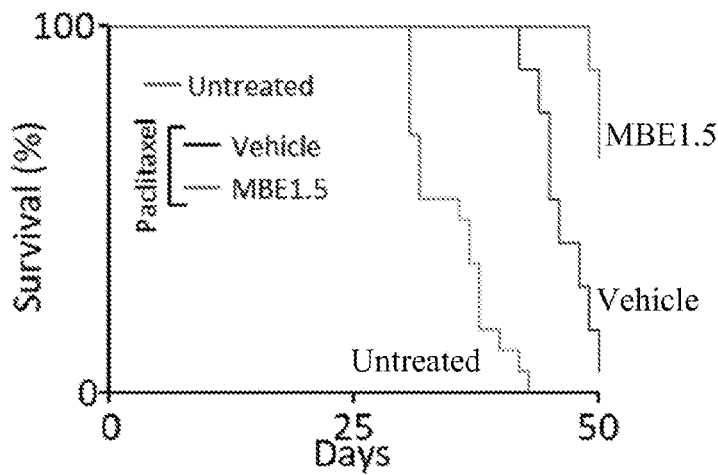

FIG. 16B is a Kaplan-Meier plot of mouse survival over time as a function of treatment group, and shows that 12-day treatment with MBE1.5 extended survival in mice with late-stage established breast cancer lung metastasis. Statistics by Cox's proportional hazards model.

DETAILED DESCRIPTION

The compounds, compositions and methods are based, in part, on the discovery that aldehyde dehydrogenase (Aldh, ALDH), and particularly ALDH isoform 1a3 (ALDH1a3), is implicated in many cancer types and other ALDH1a3-mediated diseases and disorders, such as type 2 diabetes. Accordingly, the compounds, compositions and method provided herein relate to modulating (e.g., inhibiting) ALDH, for example, ALDH1a3.

A description of example embodiments follows.

Definitions

Compounds described herein include those described generally, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are incorporated herein by reference.

Unless specified otherwise within this specification, the nomenclature used in this specification generally follows the examples and rules stated in Nomenclature of Organic Chemistry, Sections A, B, C, D, E, F, and H, Pergamon Press, Oxford, 1979, which is incorporated by reference herein for its chemical structure names and rules on naming chemical structures. Optionally, a name of a compound may be generated using a chemical naming program (e.g., CHEMDRAW®, version17.0.0.206, PerkinElmer Informatics, Inc.).

Compounds of the present invention may have asymmetric centers, chiral axes, and chiral planes (e.g., as described in: E. L. Eliel and S. H. Wilen, Stereo-chemistry of Carbon Compounds, John Wiley & Sons, New York, 1994, pages 1119-1190), and occur as racemates, racemic mixtures, and as individual diastereomers or enantiomers, with all possible isomers and mixtures thereof, including optical isomers, being included in the present invention.

"Alkyl" refers to a saturated aliphatic branched or straight-chain monovalent hydrocarbon radical having the specified number of carbon atoms. Thus, "$(C_1-C_3)$ alkyl" means a radical having from 1-3 carbon atoms in a linear or branched arrangement. Alkyl includes methyl, ethyl, propyl, isopropyl, butyl, pentyl, hexyl, etc. "$(C_1-C_3)$alkyl" includes methyl, ethyl, propyl and isopropyl.

"Amino" means —$NH_2$.

"Alkylamino" means (alkyl)(H)—N—, wherein the alkyl group is as described herein. In one aspect, an alkylamino is a $(C_1-C_3)$alkylamino. Particular alkylamino groups include methylamino, ethylamino, propylamino and isopropylamino.

"Dialkylamino" means (alkyl)$_2$-N—, wherein the alkyl groups, which may be the same or different, are as described herein. Particular dialkylamino groups are (($C_1-C_3$)alkyl)$_2$-N—, wherein the alkyl groups may be the same or different. Dialkylamino groups include dimethylamino, diethylamino and methylethylamino.

"Halogen" and "halo" are used interchangeably herein and each refers to fluorine, chlorine, bromine, or iodine. In some embodiments, halogen is selected from fluoro or chloro.

"Chloro" means —Cl.

"Fluoro" means —F.

"Cyano" means —CN.

"Nitro" means —$NO_2$.

"Hydroxy" means —OH.

"Sulfhydryl" means —SH.

"Alkoxy" refers to an alkyl radical attached through an oxygen linking atom, wherein "alkyl" is as described herein. "$(C_1-C_6)$alkoxy" includes methoxy, ethoxy, propoxy, butoxy, pentoxy and hexoxy.

"Thioalkoxy" refers to an alkyl radical attached through a sulfur linking atom, wherein "alkyl" is as described herein.

"Haloalkyl" includes mono, poly, and perhaloalkyl groups, where each halogen is independently selected from fluorine, chlorine, and bromine, and alkyl is as described herein. In one aspect, haloalkyl is perhaloalkyl (e.g., perfluoroalkyl). Haloalkyl groups include trifluoromethyl and pentafluoroethyl.

"Haloalkoxy" refers to a haloalkyl radical attached through an oxygen linking atom, wherein "haloalkyl" is as described herein.

It is understood that substituents on the compounds of the invention can be selected by one of ordinary skill in the art to provide compounds that are chemically stable and that can be readily synthesized by techniques known in the art, as well as those methods set forth below. Combinations of substituents (e.g., $R^1$-$R^9$, m, n, L, $X^1$-$X^5$) envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, the relevant teachings of which are incorporated herein by reference in their entirety. Pharmaceutically acceptable salts of the compounds described herein include salts derived from suitable inorganic and organic acids and bases that are compatible with the treatment of subjects.

Examples of pharmaceutically acceptable, nontoxic acid addition salts are salts of an amino group formed with inorganic acids such as hydrochloric acid, hydrobromic acid, phosphoric acid, sulfuric acid and perchloric acid, or with organic acids such as acetic acid, oxalic acid, maleic acid, tartaric acid, citric acid, succinic acid or malonic acid or by using other methods used in the art such as ion-exchange. Other pharmaceutically acceptable acid addition salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

In some embodiments, exemplary inorganic acids which form suitable salts include, but are not limited to, hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids, such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms.

In some embodiments, acid addition salts are most suitably formed from pharmaceutically acceptable acids, and include, for example, those formed with inorganic acids, e.g., hydrochloric, sulfuric or phosphoric acids and organic acids, e.g., succinic, maleic, acetic or fumaric acid.

Illustrative inorganic bases which form suitable salts include, but are not limited to, lithium, sodium, potassium, calcium, magnesium or barium hydroxides. Illustrative organic bases which form suitable salts include aliphatic, alicyclic or aromatic organic amines, such as methylamine, trimethyl amine and picoline, or ammonia. The selection criteria for the appropriate salt will be known to one skilled in the art.

Salts derived from appropriate bases include alkali metal, alkaline earth metal, ammonium and $N^+((C_1\text{-}C_4)\text{alkyl})_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxyl, sulfate, phosphate, nitrate, lower alkyl sulfonate and aryl sulfonate.

Additionally, unless otherwise stated, structures depicted herein are also meant to include compounds that differ only in the presence of one or more isotopically enriched atoms. For example, compounds produced by the replacement of a hydrogen with deuterium or tritium, or of a carbon with a $^{13}C$- or $^{14}C$-enriched carbon are within the scope of this invention. Such compounds are useful, for example, as analytical tools, as probes in biological assays, or as therapeutic agents in accordance with the present invention.

When introducing elements disclosed herein, the articles "a," "an," "the," and "said" are intended to mean that there are one or more of the elements. The terms "comprising," "having" and "including" are intended to be open-ended and mean that there may be additional elements other than the listed elements.

Compounds

A first embodiment is a compound represented by Structural Formula I:

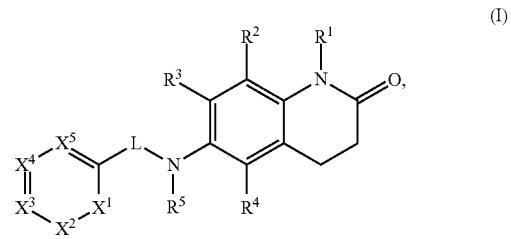

or a pharmaceutically acceptable salt thereof, wherein:
$R^1$ and $R^5$ are each independently hydrogen or $(C_1\text{-}C_6)$ alkyl;
$R^2$, $R^3$ and $R^4$ are each independently hydrogen, halo, halo$(C_1\text{-}C_3)$alkyl, $(C_1\text{-}C_3)$alkyl, $(C_1\text{-}C_3)$alkoxy, $(C_1\text{-}C_3)$thioalkoxy, halo$(C_1\text{-}C_3)$alkoxy, amino, $(C_1\text{-}C_3)$alkylamino, $(C_1\text{-}C_3)$dialkylamino, cyano, nitro, hydroxy or sulfhydryl;
L is —C(O)—, —C($R^6$)($R^7$)—, —C(CH$_2$CH$_2$)—, —C(OCH$_2$)— or —C(N(H)CH$_2$)—;
$R^6$ and $R^7$ are each independently hydrogen, hydroxy, sulfhydryl, halo, $(C_1\text{-}C_3)$alkyl, $(C_1\text{-}C_3)$alkoxy, $(C_1\text{-}C_3)$thioalkoxy or halo$(C_1\text{-}C_3)$alkoxy;

$X^1$, $X^2$, $X^3$, $X^4$ and $X^5$ are each independently —C($R^8$)— or —N—; and each $R^8$ is independently hydrogen, halo, halo($C_1$-$C_6$)alkyl, ($C_1$-$C_6$)alkyl, ($C_1$-$C_6$)alkoxy, ($C_1$-$C_6$)thioalkoxy, halo($C_1$-$C_6$)alkoxy, amino, ($C_1$-$C_6$)alkylamino, ($C_1$-$C_6$)dialkylamino, cyano, nitro, hydroxy or sulfhydryl.

In a first aspect of the first embodiment, the compound is not MBE1, MBE2, MBE3.1, MBE3.2, MBE3.3, MBE3.4, MBE3.5 or MBE3.6, or a pharmaceutically acceptable salt of any of the foregoing. Values for the variables are as described in the first embodiment.

In a second aspect of the first embodiment, $R^2$ and $R^4$ are each hydrogen. Values for the remaining variables are as described in the first embodiment, or first aspect thereof.

In a third aspect of the first embodiment, $R^1$ is hydrogen. Values for the remaining variables are as described in the first embodiment, or first or second aspect thereof.

In a fourth aspect of the first embodiment, $R^5$ is hydrogen. Values for the remaining variables are as described in the first embodiment, or first through third aspects thereof.

In a fifth aspect of the first embodiment, $R^3$ is hydrogen or halo (e.g., halo). Values for the remaining variables are as described in the first embodiment, or first through fourth aspects thereof.

In a sixth aspect of the first embodiment, $R^3$ is halo (e.g., fluoro). Values for the remaining variables are as described in the first embodiment, or first through fifth aspects thereof.

In a seventh aspect of the first embodiment, L is —C(O)— or —C($R^6$)($R^7$)—. Values for the remaining variables are as described in the first embodiment, or first through sixth aspects thereof.

In an eighth aspect of the first embodiment, L is —C(O)—. Values for the remaining variables are as described in the first embodiment, or first through seventh aspects thereof.

In a ninth aspect of the first embodiment, L is —$CH_2$—. Values for the remaining variables are as described in the first embodiment, or first through eighth aspects thereof.

In a tenth aspect of the first embodiment, one of $X^1$, $X^2$, $X^3$, $X^4$ and $X^5$ is —N—. Values for the remaining variables are as described in the first embodiment, or first through ninth aspects thereof.

In an eleventh aspect of the first embodiment, $X^3$ is —N—; and $X^1$, $X^2$, $X^4$ and $X^5$ are each independently —C($R^8$)—. Values for the remaining variables are as described in the first embodiment, or first through tenth aspects thereof.

In a twelfth aspect of the first embodiment, each $R^8$ is independently hydrogen, halo, halo($C_1$-$C_3$)alkyl, ($C_1$-$C_3$)alkyl, ($C_1$-$C_3$)alkoxy, ($C_1$-$C_3$)thioalkoxy, halo($C_1$-$C_3$)alkoxy, amino, ($C_1$-$C_3$)alkylamino, ($C_1$-$C_3$)dialkylamino, cyano, nitro, hydroxy or sulfhydryl. Values for the remaining variables are as described in the first embodiment, or first through eleventh aspects thereof.

In a thirteenth aspect of the first embodiment, each $R^8$ is independently hydrogen, halo or ($C_1$-$C_6$)alkyl (e.g., hydrogen or ($C_1$-$C_6$)alkyl). Values for the remaining variables are as described in the first embodiment, or first through twelfth aspects thereof.

In a fourteenth aspect of the first embodiment, $R^6$ and $R^7$ are each independently hydrogen, hydroxy, halo, ($C_1$-$C_3$)alkyl or ($C_1$-$C_3$)alkoxy, for example, $R^6$ and $R^7$ are each independently hydrogen, hydroxy or halo, for example, $R^6$ and $R^7$ are each hydrogen. Values for the remaining variables are as described in the first embodiment, or first through thirteenth aspects thereof.

Compounds of Structural Formula I include MBE1, MBE1.2, MBE1.3, MBE1.5, MBE1.6, MBE2, MBE3.1, MBE3.2, MBE3.3, MBE3.4, MBE3.5 and MBE3.6, or a pharmaceutically acceptable salt of any of the foregoing. Compounds of Structural Formula I also include MBE1.5A, MBE1.5B, MBE1.5C and MBE1.5D, or a pharmaceutically acceptable salt of the foregoing.

In a second embodiment, the compound is represented by Structural Formula II:

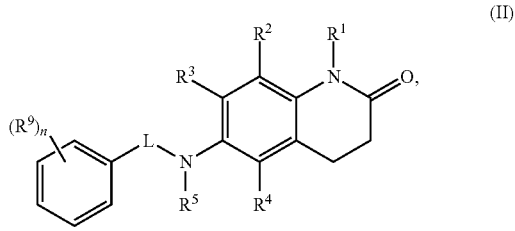

(II)

or a pharmaceutically acceptable salt thereof, wherein:

$R^1$ and $R^5$ are each independently hydrogen or ($C_1$-$C_6$)alkyl;

$R^2$ and $R^4$ are each independently hydrogen, halo, halo($C_1$-$C_3$)alkyl, ($C_1$-$C_3$)alkyl, ($C_1$-$C_3$)alkoxy, ($C_1$-$C_3$)thioalkoxy, halo($C_1$-$C_3$)alkoxy, amino, ($C_1$-$C_3$)alkylamino, ($C_1$-$C_3$)dialkylamino, cyano, nitro, hydroxy or sulfhydryl;

$R^3$ is halo, halo($C_1$-$C_3$)alkyl, ($C_1$-$C_3$)alkyl, ($C_1$-$C_3$)alkoxy, ($C_1$-$C_3$)thioalkoxy, halo($C_1$-$C_3$)alkoxy, amino, ($C_1$-$C_3$)alkylamino, ($C_1$-$C_3$)dialkylamino, cyano, nitro, hydroxy or sulfhydryl;

L is —C(O)—, —C($R^6$)($R^7$)—, —C($CH_2CH_2$)—, —C($OCH_2$)— or —C(N(H)$CH_2$)—;

$R^6$ and $R^7$ are each independently hydrogen, hydroxy, sulfhydryl, halo, ($C_1$-$C_3$)alkyl, $C_3$)alkoxy, ($C_1$-$C_3$)thioalkoxy or halo($C_1$-$C_3$)alkoxy;

each $R^9$ is independently halo, halo($C_1$-$C_6$)alkyl, ($C_1$-$C_6$)alkyl, ($C_1$-$C_6$)alkoxy, ($C_1$-$C_6$)thioalkoxy, halo($C_1$-$C_6$)alkoxy, amino, ($C_1$-$C_6$)alkylamino, ($C_1$-$C_6$)dialkylamino, cyano, nitro, hydroxy or sulfhydryl; and n is 0, 1, 2, 3, 4, or 5. Alternative values for the variables are as described in the first embodiment, or any aspect thereof.

In a first aspect of the second embodiment, each $R^9$ is independently halo, halo($C_1$-$C_3$)alkyl, ($C_1$-$C_3$)alkyl, ($C_1$-$C_3$)alkoxy, ($C_1$-$C_3$)thioalkoxy, halo($C_1$-$C_3$)alkoxy, amino, ($C_1$-$C_3$)alkylamino, ($C_1$-$C_3$)dialkylamino, cyano, nitro, hydroxy or sulfhydryl. Values for the remaining variables are as described in the first embodiment, or any aspect thereof, or the second embodiment.

In a second aspect of the second embodiment, each $R^9$ is independently halo or ($C_1$-$C_6$)alkyl (e.g., halo or ($C_1$-$C_3$)alkyl). Values for the remaining variables are as described in the first embodiment, or any aspect thereof, or the second embodiment, or first aspect thereof.

In a third aspect of the second embodiment, n is 0, 1 or 2 (e.g., n is 0, n is 1 or n is 2). Values for the remaining variables are as described in the first embodiment, or any aspect thereof, or the second embodiment, or first or second aspects thereof.

In a fourth aspect of the second embodiment, each $R^9$ is independently ($C_1$-$C_6$)alkyl. Values for the remaining variables are as described in the first embodiment, or any aspect thereof, or the second embodiment, or first through third aspects thereof.

In a fifth aspect of the second embodiment, n is 1 or 2 (e.g., 1). Values for the remaining variables are as described in the first embodiment, or any aspect thereof, or the second embodiment, or first through fourth aspects thereof.

Compounds of Structural Formula II include MBE1.5, or a pharmaceutically acceptable salt thereof. Compounds of Structural Formula II also include MBE1.5A, MBE1.5B, MBE1.5C and MBE1.5D, or a pharmaceutically acceptable salt of the foregoing.

A third embodiment is a compound represented by Structural Formula III:

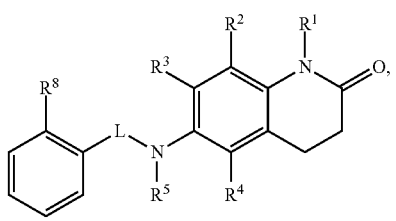

(III)

or a pharmaceutically acceptable salt thereof, wherein values for the variables are as described in the first or second embodiment, or any aspect of the foregoing.

A fourth embodiment is a compound represented by Structural Formula IV:

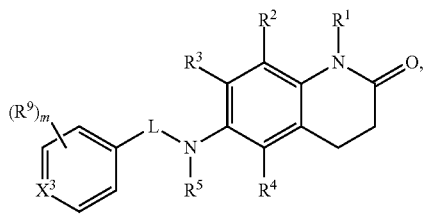

(IV)

or a pharmaceutically acceptable salt thereof, wherein:
each $R^9$ is independently halo, halo($C_1$-$C_6$)alkyl, ($C_1$-$C_6$) alkyl, ($C_1$-$C_6$)alkoxy, ($C_1$-$C_6$)thioalkoxy, halo($C_1$-$C_6$) alkoxy, amino, ($C_1$-$C_6$)alkylamino, ($C_1$-$C_6$)dialkylamino, cyano, nitro, hydroxy or sulfhydryl; and
m is 0, 1, 2, 3 or 4. Alternative values for variables $R^9$ and values for the remaining variables are as described in the first or second embodiment, or any aspect of the foregoing.

In a first aspect of the fourth embodiment, $X^3$ is —C($R^8$)—. Values for the remaining variables are as described in the first or second embodiment or any aspect of the foregoing, or the fourth embodiment.

In a second aspect of the fourth embodiment, $X^3$ is —N—. Values for the remaining variables are as described in the first or second embodiment or any aspect of the foregoing, or the fourth embodiment, or first aspect thereof.

In a third aspect of the fourth embodiment, m is 0, 1 or 2. Values for the remaining variables are as described in the first or second embodiment, or any aspect of the foregoing, or the fourth embodiment, or first or second aspect thereof.

In a fourth aspect of the fourth embodiment, $R^3$ is halo, halo($C_1$-$C_3$)alkyl, ($C_1$-$C_3$)alkyl, ($C_1$-$C_3$)alkoxy, ($C_1$-$C_3$) thioalkoxy, halo($C_1$-$C_3$)alkoxy, amino, ($C_1$-$C_3$)alkylamino, ($C_1$-$C_3$)dialkylamino, cyano, nitro, hydroxy or sulfhydryl. Values for the remaining variables are as described in the first or second embodiment, or any aspect of the foregoing, or the fourth embodiment, or first through third aspects thereof.

In a fifth aspect of the fourth embodiment, the compound is not MBE1 or MBE3.6, or a pharmaceutically acceptable salt of the foregoing. Values for the remaining variables are as described in the first or second embodiment, or any aspect of the foregoing, or the fourth embodiment, or first through fourth aspects thereof.

A fifth embodiment is a compound represented by Structural Formula V:

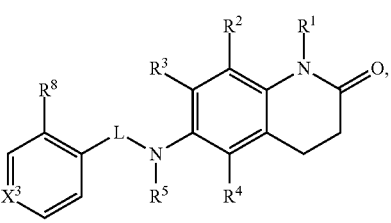

(V)

or a pharmaceutically acceptable salt thereof. Values for the variables are as described in the first, second or fourth embodiment, or any aspect of the foregoing.

Compounds of Structural Formula V include MBE1.2, MBE1.3 and MBE1.6, or a pharmaceutically acceptable salt of the foregoing.

A sixth embodiment is a compound represented by Structural Formula VI:

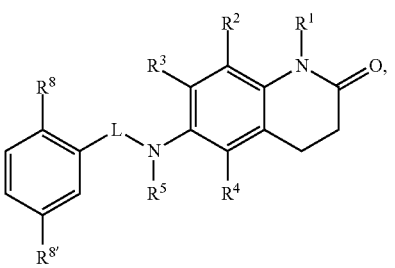

(VI)

or a pharmaceutically acceptable salt thereof, wherein $R^{8'}$ is hydrogen, halo, halo($C_1$-$C_6$)alkyl, ($C_1$-$C_6$)alkyl, ($C_1$-$C_6$) alkoxy, ($C_1$-$C_6$)thioalkoxy, halo($C_1$-$C_6$)alkoxy, amino, ($C_1$-$C_6$)alkylamino, ($C_1$-$C_6$)dialkylamino, cyano, nitro, hydroxy or sulfhydryl (e.g., hydrogen or ($C_1$-$C_6$)alkyl). Values for the remaining variables are as described in the first, second or fourth embodiment, or any aspect of the foregoing.

In a first aspect of the sixth embodiment, $R^8$ is ($C_1$-$C_6$) alkyl. Values for the remaining variables are as described in the first, second or fourth embodiment, or any aspect of the foregoing, or the sixth embodiment.

A seventh embodiment is a compound represented by Structural Formula VII:

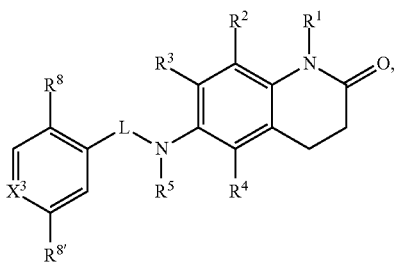

(VII)

or a pharmaceutically acceptable salt thereof, wherein $R^{8'}$ is hydrogen, halo, halo($C_1$-$C_6$)alkyl, ($C_1$-$C_6$)alkyl, ($C_1$-$C_6$) alkoxy, ($C_1$-$C_6$)thioalkoxy, halo($C_1$-$C_6$)alkoxy, amino, ($C_1$-$C_6$)alkylamino, ($C_1$-$C_6$)dialkylamino, cyano, nitro, hydroxy or sulfhydryl (e.g., hydrogen or ($C_1$-$C_6$)alkyl). Values for the remaining variables are as described in the first, second, fourth or sixth embodiment, or any aspect of the foregoing.

Compositions and Kits

Provided herein is a composition (e.g., a pharmaceutically acceptable composition) comprising an agent that inhibits ALDH1a3 (e.g., a compound of any of Structural Formulas I-V, or a pharmaceutically acceptable salt of the foregoing), and a pharmaceutically acceptable carrier or excipient. In certain embodiments, a composition of the invention is formulated for administration to a subject (e.g., patient) in need of the composition. In some embodiments, a composition of the invention is formulated for oral, intravenous, subcutaneous, intraperitoneal or dermatological administration to a subject in need thereof.

The phrase "pharmaceutically acceptable carrier or excipient" refers to a non-toxic carrier or excipient that does not destroy the pharmacological activity of the agent with which it is formulated and is nontoxic when administered in doses sufficient to deliver a therapeutic amount of the agent. Pharmaceutically acceptable carriers or excipients that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium tri silicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions described herein may be administered orally, parenterally (including subcutaneous, intramuscular, intravenous and intradermal), by inhalation spray, topically, rectally, nasally, buccally, vaginally or via an implanted reservoir. In some embodiments, provided compounds or compositions are administrable intravenously and/or intraperitoneally.

The term "parenteral," as used herein, includes subcutaneous, intracutaneous, intravenous, intramuscular, intraocular, intravitreal, intra-articular, intra-arterial, intra-synovial, intrasternal, intrathecal, intralesional, intrahepatic, intraperitoneal intralesional and intracranial injection or infusion techniques. Preferably, the compositions are administered orally, subcutaneously, intraperitoneally or intravenously.

Compositions provided herein can be orally administered in any orally acceptable dosage form including, but not limited to, capsules, tablets, aqueous suspensions, dispersions and solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions and/or emulsions are required for oral use, the active ingredient can be suspended or dissolved in an oily phase and combined with emulsifying and/or suspending agents. If desired, certain sweetening, flavoring or coloring agents may also be added.

In some embodiments, an oral formulation is formulated for immediate release or sustained/delayed release.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders, such as carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium salts, (g) wetting agents, such as acetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Compositions suitable for buccal or sublingual administration include tablets, lozenges and pastilles, wherein the active ingredient is formulated with a carrier such as sugar and acacia, tragacanth, or gelatin and glycerin.

Solid compositions of a similar type may also be employed as fillers in soft and hard-filled gelatin capsules using excipients such as lactose or milk sugar, as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

An agent can also be in micro-encapsulated form with one or more excipients, as noted above. In such solid dosage forms, the agent can be admixed with at least one inert diluent such as sucrose, lactose or starch. Such dosage forms can also comprise, as is normal practice, additional substances other than inert diluents, e.g., tableting lubricants and other tableting aids such a magnesium stearate and microcrystalline cellulose.

Compositions for oral administration may be designed to protect the active ingredient against degradation as it passes through the alimentary tract, for example, by an outer coating of the formulation on a tablet or capsule.

In another embodiment, an agent can be provided in an extended (or "delayed" or "sustained") release composition. This delayed-release composition comprises the agent in combination with a delayed-release component. Such a composition allows targeted release of a provided agent into the lower gastrointestinal tract, for example, into the small intestine, the large intestine, the colon and/or the rectum. In certain embodiments, a delayed-release composition further comprises an enteric or pH-dependent coating, such as cellulose acetate phthalates and other phthalates (e.g., polyvinyl acetate phthalate, methacrylates (Eudragits)). Alternatively, the delayed-release composition provides controlled release to the small intestine and/or colon by the provision of pH sensitive methacrylate coatings, pH sensitive polymeric microspheres, or polymers which undergo degradation by hydrolysis. The delayed-release composition can be formulated with hydrophobic or gelling excipients or coatings. Colonic delivery can further be provided by coatings which are digested by bacterial enzymes such as amylose or pectin, by pH dependent polymers, by hydrogel plugs swelling with time (Pulsincap), by time-dependent hydrogel coatings and/or by acrylic acid linked to azoaromatic bonds coatings.

Compositions described herein can also be administered in the form of suppositories for rectal administration. These can be prepared by mixing an agent with a suitable non-irritating excipient that is solid at room temperature but liquid at rectal temperature and, therefore, will melt in the rectum to release the drug. Such materials include cocoa butter, beeswax and polyethylene glycols.

Compositions described herein can also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches can also be used.

For other topical applications, the compositions can be formulated in a suitable ointment containing the active component suspended or dissolved in one or more carriers. Carriers for topical administration of an agent include, but are not limited to, mineral oil, liquid petrolatum, white petrolatum, propylene glycol, polyoxyethylene, polyoxypropylene compound, emulsifying wax and water and penetration enhancers. Alternatively, compositions can be formulated in a suitable lotion or cream containing the active component suspended or dissolved in one or more pharmaceutically acceptable carriers. Alternatively, the composition can be formulated with a suitable lotion or cream containing the active compound suspended or dissolved in a carrier with suitable emulsifying agents. In some embodiments, suitable carriers include, but are not limited to, mineral oil, sorbitan monostearate, polysorbate 60, cetyl esters wax, cetearyl alcohol, 2-octyldodecanol, benzyl alcohol and water. In other embodiments, suitable carriers include, but are not limited to, mineral oil, sorbitan monostearate, polysorbate 60, cetyl esters wax, cetearyl alcohol, 2-octyldodecanol, benzyl alcohol and water and penetration enhancers.

For ophthalmic use, compositions can be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the compositions can be formulated in an ointment such as petrolatum.

Compositions can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents.

The amount of an agent that can be combined with the carrier materials to produce a composition in a single dosage form will vary depending upon the host treated, the particular mode of administration and the activity of the agent employed. Preferably, compositions should be formulated so that a dosage of from about 0.01 mg/kg to about 100 mg/kg body weight/day of the agent can be administered to a subject receiving the composition.

It should also be understood that a specific dosage and treatment regimen for any particular patient will depend upon a variety of factors, including the activity of the specific agent employed, the age, body weight, general health, sex, diet, time of administration, rate of excretion, drug combination, the judgment of the treating physician and the severity of the particular disease being treated. The amount of an agent in the composition will also depend upon the particular agent in the composition.

Other pharmaceutically acceptable carriers, adjuvants and vehicles that can be used in the compositions of this invention include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-3-cyclodextrins, or other solubilized derivatives can also be advantageously used to enhance delivery of agents described herein.

The compositions can be in the form of a sterile injectable preparation, for example, as a sterile injectable aqueous or oleaginous suspension. This suspension can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium. For this purpose, any bland fixed oil can be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms can also be used for the purposes of formulation.

In some embodiments, compositions comprising an agent that inhibits ALDH1a3 (e.g., a compound of any of Structural Formulas I-VII, or a pharmaceutically acceptable salt of the foregoing) can also include one or more other therapeutic agents (e.g., a chemotherapeutic agent, for example, paclitaxel, doxorubicin, 5-fluorouracil, tamoxifen, octreotide). When the compositions of this invention comprise a combination of an agent that inhibits ALDH1a3 and one or more other therapeutic agents, the agents should be present at dosage levels of between about 1 to 100%, and more preferably between about 5% to about 95% of the dosage normally administered in a monotherapy regimen. The additional agent(s) can be administered separately, as part of a multiple dose regimen, from the agent that inhibits ALDH1a3. Alternatively, the additional agent(s) can be part of a single dosage form, mixed together with the agent that inhibits ALDH1a3 in a single composition.

The compositions described herein can, for example, be administered by injection, intravenously, intraarterially, intraocularly, intravitreally, subdermallym, orally, buccally, nasally, transmucosally, topically, in an ophthalmic preparation, or by inhalation, with a dosage ranging from about 0.5 mg/kg to about 100 mg/kg of body weight or, alternatively, in a dosage ranging from about 1 mg/dose to about 1000 mg/dose, every 4 to 120 hours, or according to the requirements of the particular drug. Typically, the compositions will be administered from about 1 to about 6 times per day or, alternatively, as a continuous infusion. The amount of active ingredient that can be combined with a carrier material to produce a single dosage form will vary depending upon the host treated and the particular mode of administration. A typical preparation will contain from about 5% to about 95% active compound (w/w). Alternatively, a preparation can contain from about 20% to about 80% active compound (w/w).

Doses lower or higher than those recited above may be required. Specific dosage and treatment regimens for any particular patient will depend upon a variety of factors, including the activity of the specific agent employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a subject's condition, a maintenance dose of an agent (e.g., a compound of any of Structural Formulas I-VII, or a pharmaceutically acceptable salt of the foregoing), composition or combination of this invention can be administered, if necessary. Subsequently, the dosage or frequency of administration, or both, can be reduced, as a function of the symptoms, to a level at which the improved condition is retained when the symptoms have been alleviated to the desired level. Subjects may, however, require intermittent treatment on a long-term basis upon recurrence of disease symptoms.

Also provided herein is a kit comprising an agent described herein (e.g., a compound of any of Structural Formulas or a pharmaceutically acceptable salt of the foregoing), and an additional agent(s). In one embodiment, the kit comprises an effective amount of an agent described herein to treat a disease, disorder or condition described herein (e.g., cancer, type 2 diabetes), and an effective amount of an additional agent(s) to treat the disease, disorder or condition. In some embodiments, the kit further comprises written instructions for administering the agent and the additional agent(s) to a subject to treat a disease, disorder or condition described herein (e.g., cancer, type 2 diabetes).

Methods

Aldehyde dehydrogenases (ALDHs) belong to a super-family of NAD(P+)-dependent enzymes that play a role in the metabolism of aldehydes by irreversibly catalyzing the oxidation of both endogenously and exogenously produced aldehydes to their respective carboxylic acids. ALDHs have a broad spectrum of biological activities, including biosynthesis of retinoic acid (RA) and alcohol metabolism, among others.

The ALDH family of enzymes contains 19 members with diverse functions. Enzymes within this family irreversibly catalyze the oxidation of an aldehyde into the corresponding carboxylic acid while reducing NAD+/NADP+ to NADH/NADPH. These enzymes are found in several cellular compartments, however, most are localized to the cytosol or the mitochondria. Some ALDH enzymes participate in global metabolism via expression in the liver where they function to detoxify acetylaldehyde formed from alcohol dehydrogenases, biosynthesize vitamin A from retinal stereoisomers, or detoxify other reactive aldehydes. In contrast, most ALDH enzymes are expressed in a cell- or disease-specific manner and modulate cellular biochemistry, often with unknown mechanisms of action.

Aldehyde dehydrogenase isoform 1a3 (ALDH1a3) is an isoform/isozyme of the ALDH1a subfamily that is crucial in the biosynthesis of RA and the regulation of RA signaling, and is cell- and disease-specific. ALDH1a3 was known as ALDH6 prior to 2000, and as Raldh3 from 2000-2007. In normal conditions, ALDH1a3 is only required during embryonic development and is dispensable to healthy adult mice. In contrast to its minor role in normal physiology, ALDH1a3 has recently been shown to be the major determinant of ALDEFLUOR™ reactivity across most cancer types. ALDEFLUOR™ activity has long been used as a marker to differentiate aggressive cancer cells from the bulk tumor despite an overlying ignorance regarding if/how ALDEFLUOR™ activity affects tumor progression.

It has been discovered that ALDEFLUOR™ activity driven by ALDH1a3 is a functional driver of cancer aggressiveness, and is critical for tumor progression, metastasis, and resistance to chemotherapy. Thus, human ALDH1a3 (UniProtKB Accession No.: P47895) is a functional driver of chemoresistant and metastatic phenotypes in cancer, including breast cancer. Accordingly, ALDH1a3 represents a potential therapeutic target in multiple pathologies, and targeting ALDH1a3 may overcome the current barrier in treating Stage 3/4 patients whose tumors are resistant to conventional forms of therapy.

Accordingly, provided herein is a method of treating a cancer (e.g., a metastatic cancer, a chemoresistant cancer) in a subject in need thereof, comprising administering to the subject an effective amount of an agent that inhibits ALDH1a3 (e.g., a compound of any of Structural Formulas I-VII, or a pharmaceutically acceptable salt of the foregoing, or a composition comprising a compound of any of Structural Formulas I-VII, or a pharmaceutically acceptable salt of the foregoing). Thus, in some embodiments, provided is a method of treating a cancer (e.g., a metastatic cancer, a chemoresistant cancer) in a subject in need thereof, comprising administering to the subject an effective amount of a compound of any of Structural Formulas I-VII, or a pharmaceutically acceptable salt of the foregoing, or a composition comprising a compound of any of Structural Formulas or a pharmaceutically acceptable salt of the foregoing. In further embodiments, provided is a method of treating a cancer (e.g., a metastatic cancer, a chemoresistant cancer) in a subject in need thereof, comprising administering to the subject an effective amount of a compound of Table 1 (e.g., MBE1, MBE1.5, MBE1.5A, MBE1.5B, MBE1.5C, MBE1.5D), or a pharmaceutically acceptable salt thereof, or a composition comprising a compound of Table 1 (e.g., MBE1, MBE1.5, MBE1.5A, MBE1.5B, MBE1.5C, MBE1.5D), or a pharmaceutically acceptable salt thereof.

Also provided herein is a method of treating type 2 diabetes in a subject in need thereof, comprising administering to the subject an effective amount of an agent that inhibits ALDH1a3 (e.g., a compound of any of Structural Formulas I-VII, or a pharmaceutically acceptable salt of the foregoing, or a composition comprising a compound of any of Structural Formulas I-VII, or a pharmaceutically acceptable salt of the foregoing). Thus, in some embodiments, provided is a method of treating type 2 diabetes in a subject in need thereof, comprising administering to the subject an effective amount of a compound of any of Structural Formulas I-VII, or a pharmaceutically acceptable salt of the foregoing, or a composition comprising a compound of any of Structural Formulas I-VII, or a pharmaceutically acceptable salt of the foregoing. In further embodiments, provided is a method of treating type 2 diabetes in a subject in need thereof, comprising administering to the subject an effective amount of a compound of Table 1 (e.g., MBE1, MBE1.5, MBE1.5A, MBE1.5B, MBE1.5C, MBE1.5D), or a pharmaceutically acceptable salt thereof, or a composition comprising a compound of Table 1 (e.g., MBE1, MBE1.5, MBE1.5A, MBE1.5B, MBE1.5C, MBE1.5D), or a pharmaceutically acceptable salt thereof.

As used herein, the terms "treat," "treating," or "treatment," mean to counteract a medical condition (e.g., a condition related to cancer) to the extent that the medical condition is improved according to a clinically-acceptable standard (e.g., reduced number of cancer metastases in a subject).

In an embodiment, the subject (e.g., patient) is a mammal (e.g., human, non-human primate, cow, sheep, goat, horse, dog, cat, rabbit, guinea pig, rat, mouse or other bovine, ovine, equine, canine, feline, or rodent organism). In a particular embodiment, the subject is a human. A "subject in need thereof" refers to a subject who has, or is at risk for developing, a disease or condition described herein (e.g., cancer, a metastatic cancer). A skilled medical professional (e.g., physician) can readily determine whether a subject has, or is at risk for developing, a disease or condition described herein (e.g., cancer).

In an embodiment, the subject in need thereof has cancer (e.g., a metastatic cancer, a chemoresistant cancer). The cancer can be a solid tumor, a leukemia, a lymphoma or a myeloma. In particular embodiments, the subject in need thereof has a breast cancer, a colon cancer, a lung cancer, a pancreatic cancer, a prostate cancer, a bone cancer, a blood cancer, a brain cancer, or a liver cancer. In some embodiments, the cancer is breast (e.g., triple negative breast), clear cell renal cell, gastric, bladder, ovarian, squamous cell lung, colorectal or glioma (e.g., low-grade glioma) cancer.

Cancers include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Mantle Cell Lymphoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor.

Metastases of the aforementioned cancers can also be treated in accordance with the methods described herein. Thus, in some embodiments, the cancer is a metastatic cancer.

"Metastatic cancer," as used herein, refers to a cancer that has spread from its primary site of origin or where it first formed to other areas of a subject's body. Examples of metastatic cancers include metastatic breast cancer, metastatic colon cancer, metastatic lung cancer, metastatic pancreatic cancer, metastatic prostate cancer, metastatic bone cancer, metastatic blood cancer, metastatic brain cancer, and metastatic liver cancer. In one embodiment, the subject has a bone metastasis (e.g., spontaneous bone metastasis) of a breast cancer. In another embodiment, the subject has a lung metastasis of a breast cancer. In yet another embodiment, the subject has a bone metastasis.

In a particular embodiment, the subject in need thereof has a breast cancer (e.g., a metastatic breast cancer). Breast cancer subtypes that are particularly suitable for treatment using the methods described herein include, but are not limited to, basal-like breast cancers and HER2-positive breast cancers.

"Resistant cancer," as used herein, is cancer that does not respond to treatment. "Resistant cancers" include those that are non-responsive to treatment at the beginning of treatment, and those that become non-responsive to treatment during treatment. In an embodiment, the cancer is resistant cancer.

In an embodiment, the subject in need thereof has a cancer that is resistant to treatment with one or more chemotherapeutic agents, or a chemoresistant cancer. "Chemoresistant cancer," as used herein, refers to a cancer that does not respond to treatment with one or more chemotherapeutic agents. "Chemoresistant cancers" include those that are non-responsive to treatment with one or more therapeutic agents at the beginning of treatment, and those that become non-responsive to treatment with one or more therapeutic agents during treatment. Chemoresistant cancers that are particularly suitable for treatment using the methods described herein include, but are not limited to, cancers that are resistant to treatment with paclitaxel and/or doxorubicin.

In an embodiment, the subject in need thereof has an aggressive cancer. As used herein, "aggressive cancer" refers to a cancer that progresses (e.g., forms, grows, and/or metastasizes) quickly, or a cancer that requires treatment that is more severe or intense than typical cancer treatments for the same type of cancer. Aggressive cancers include but are not limited to cancers of the lung, breast, pancreas, kidney, colon, rectum, brain, liver, and prostate or the hematological system that do not respond to conventional treatment, e.g., chemotherapy (including taxanes, anthracyclines, alkylating agents, etc.), radiotherapy (e.g., proton beam irradiation) or targeted biological treatment (e.g., herceptin, Keytruda, etc.), or which progress during treatment with any accepted modality or which have metastasized upon diagnosis (Stage III/IV cancers). As a specific example, aggressive cancers of the prostate either lose response to anti-androgen therapies or radiation and often metastasize to the bone, while aggressive melanoma is any tumor which has spread beyond the dermis. All diagnoses of glioblastoma multiforme are considered aggressive. Aggressive cancers often spread to distant sites and cause significant morbidity owing to the lack of targeted treatments.

In some embodiments, the subject in need thereof has an advanced (e.g., Stage III/IV) cancer.

In some embodiments, the cancer is a primary cancer (e.g., a primary solid tumor). As used herein, "primary cancer" refers to the original site of a cancer (e.g., tumor) in a subject's body.

As used herein, an "effective amount" is an amount of agent that, when administered to a subject, is sufficient to achieve a desired therapeutic effect in the subject under the conditions of administration, such as an amount sufficient to inhibit (e.g., reduce, decrease, prevent) tumor formation, tumor growth (e.g., proliferation, size), tumor vascularization, tumor progression (e.g., invasion, metastasis) and/or chemoresistance in a subject (e.g., patient) with a cancer. The effectiveness of a therapy (e.g., the reduction and/or prevention of tumor metastasis) can be determined by any suitable method known to those of skill in the art (e.g., in situ immunohistochemistry, imaging (e.g., ultrasound, CT scan, MRI, NMR), $^3$H-thymidine incorporation).

An effective amount of the agent to be administered can be determined by a clinician of ordinary skill using the guidance provided herein and other methods known in the art, and is dependent on several factors including, for example, the particular agent chosen, the subject's age, sensitivity, tolerance to drugs and overall well-being. For example, suitable dosages can be from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg body weight per treatment. Determining the dosage for a particular agent, subject and cancer is well within the abilities of one of skill in the art. Preferably, the dosage does not cause or produces minimal adverse side effects (e.g., immunogenic response, nausea, dizziness, gastric upset, hyperviscosity syndromes, congestive heart failure, stroke, pulmonary edema).

An agent that inhibits ALDH1a3 can be administered in a single dose or as multiple doses, for example, in an order and on a schedule suitable to achieve a desired therapeutic effect (e.g., inhibition of cancer metastasis). Suitable dosages and regimens of administration can be determined by a clinician of ordinary skill.

An agent that inhibits ALDH1a3 can also be administered in combination with one or more other therapies or treatments. With respect to the administration of an agent in combination with one or more other therapies or treatments (adjuvant, targeted, cancer treatment-associated, and the like), the agent is typically administered as a single dose (by, e.g., injection, infusion, orally), followed by repeated doses at particular intervals (e.g., one or more hours) if desired or indicated.

In one embodiment, the agent can be administered in a metronomic dosing regimen, whereby a lower dose is administered more frequently relative to maximum tolerated dosing. A number of preclinical studies have demonstrated superior anti-tumor efficacy, potent antiangiogenic effects, and reduced toxicity and side effects (e.g., myelosuppression) of metronomic regimes compared to maximum tolerated dose (MTD) counterparts (Bocci, et al., *Cancer Res*, 62:6938-6943, (2002); Bocci, et al., *Proc. Natl. Acad. Sci.*, 100(22):12917-12922, (2003); and Bertolini, et al., *Cancer Res*, 63(15):4342-4346, (2003)). Metronomic chemotherapy appears to be effective in overcoming some of the shortcomings associated with chemotherapy.

An agent that inhibits ALDH1a3 can be administered to the subject in need thereof as a primary therapy (e.g., as the principal therapeutic agent in a therapy or treatment regimen); as an adjunct therapy (e.g., as a therapeutic agent used together with another therapeutic agent in a therapy or treatment regime, wherein the combination of therapeutic agents provides the desired treatment; "adjunct therapy" is also referred to as "adjunctive therapy"); in combination with an adjunct therapy; as an adjuvant therapy (e.g., as a therapeutic agent that is given to the subject in need thereof after the principal therapeutic agent in a therapy or treatment regimen has been given); or in combination with an adjuvant therapy. Adjuvant therapies include, for example, chemotherapy (e.g., paclitaxel, doxorubicin, tamoxifen, cisplatin, mitomycin, 5-fluorouracil, sorafenib, octreotide, dacarbazine (DTIC), cis-platinum, cimetidine, cyclophosphamide), radiation therapy (e.g., proton beam therapy), hormone therapy (e.g., anti-estrogen therapy, androgen deprivation therapy (ADT), luteinizing hormone-releasing hormone (LH-RH) agonists, aromatase inhibitors (AIs, such as anastrozole, exemestane, letrozole), estrogen receptor modulators (e.g., tamoxifen, raloxifene, toremifene), or biological therapy. Numerous other therapies can also be administered during a cancer treatment regime to mitigate the effects of the disease and/or side effects of the cancer treatment including therapies to manage pain (narcotics, acupuncture), gastric discomfort (antacids), dizziness (anti-vertigo medications), nausea (anti-nausea medications), infection (e.g., medications to increase red/white blood cell counts) and the like, all of which are readily appreciated by the person skilled in the art.

In some embodiments, the method comprises administering an effective amount of an agent that inhibits ALDH1a3 in combination with one or more additional therapies (e.g., chemotherapy, radiation and/or the surgical removal of a tumor(s)). When administered in a combination therapy, the agent can be administered before, after or concurrently with the other therapy (e.g., administration of a chemotherapeutic agent, such as paclitaxel or doxorubicin). When co-administered simultaneously (e.g., concurrently), the agent and other therapy can be in separate formulations or the same formulation. Alternatively, the agent and other therapy can be administered sequentially, as separate compositions, within an appropriate time frame (e.g., a cancer treatment session/interval such as about 1.5 to about 5 hours) as determined by a skilled clinician (e.g., a time sufficient to allow an overlap of the pharmaceutical effects of the therapies).

An agent that inhibits ALDH1a3 can be administered via a variety of routes of administration, including, for example, oral, dietary, topical, transdermal, rectal, parenteral (e.g., intra-arterial, intravenous, intramuscular, subcutaneous injection, intradermal injection), intravenous infusion and inhalation (e.g., intrabronchial, intranasal or oral inhalation, intranasal drops) routes of administration, depending on the agent and the particular cancer to be treated. Administration can be local or systemic as indicated. The preferred mode of administration can vary depending on the particular agent chosen.

The actual dose of a therapeutic agent and treatment regimen can be determined by the physician, taking into account, for example, the nature of the cancer (primary or metastatic), number and size of tumors, other therapies being given, and subject characteristics.

Also provided herein is a method of inhibiting the proliferation of a cancer cell (e.g., a metastatic cancer cell, a chemoresistant cancer cell). The method comprises administering to the cell (e.g., an effective amount of) an agent that inhibits ALDH1a3 (e.g., a compound of any of Structural Formulas I-VII, or a pharmaceutically acceptable salt of the foregoing, or a composition comprising a compound of any of Structural Formulas I-VII, or a pharmaceutically acceptable salt of the foregoing). In a particular embodiment, the cancer cell is a breast cancer cell (e.g., a basal-like breast cancer cell or a HER-2 positive breast cancer cell). The cell can be a cultured cell (e.g., cell line) or a cell in a subject. In a particular embodiment, the cell is present in a human subject (e.g., a human subject with a cancer).

Also provided herein is a method of inhibiting ALDH1a3 in a subject in need thereof. The method comprises administering to the subject (e.g., an effective amount of) an agent that inhibits ALDH1a3 (e.g., a compound of any of Structural Formulas I-VII, or a pharmaceutically acceptable salt of the foregoing, or a composition comprising a compound of any of Structural Formulas I-VII, or a pharmaceutically acceptable salt of the foregoing).

Also provided herein is a method of treating a disease or disorder mediated by ALDH1a3, such as a cancer type described herein, in a subject in need thereof. The method comprises administering to the subject an effective amount of an agent that inhibits ALDH1a3 (e.g., a compound of any of Structural Formulas I-VII, or a pharmaceutically acceptable salt of the foregoing, or a composition comprising a compound of any of Structural Formulas I-VII, or a pharmaceutically acceptable salt of the foregoing). ALDH1a3 has also been implicated in type 2 diabetes. Accordingly, type 2 diabetes is another example of an ALDH1a3-mediated disease or disorder.

EXEMPLIFICATION

Synthesis of N-(7-fluoro-2-oxo-1,2,3,4-tetrahydroquinolin-6-yl)isonicotinamide (MBE1.2)

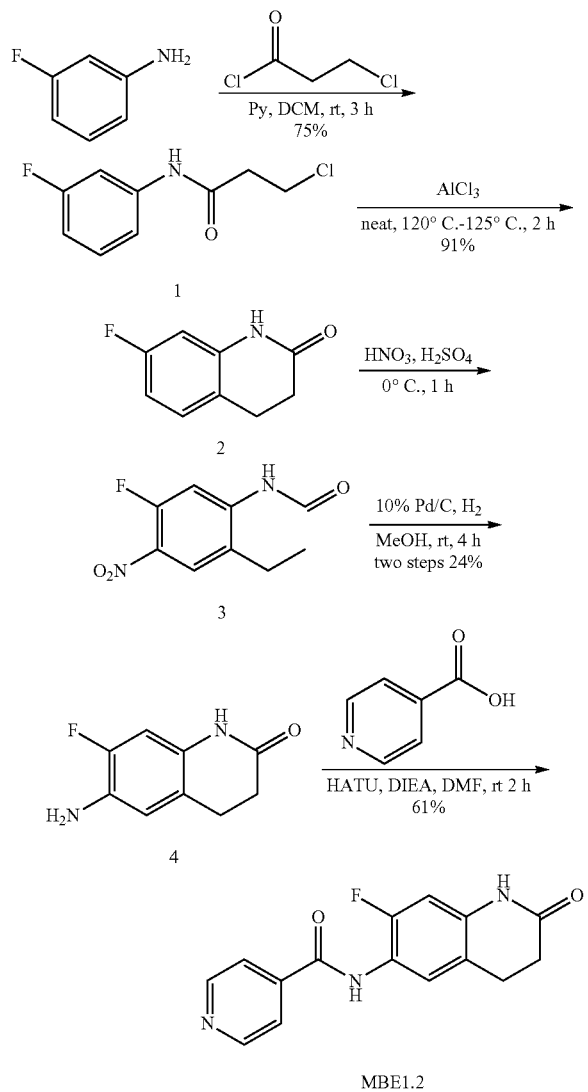

3-Chloro-N-(3-fluorophenyl)propanamide: Into a 2-L round-bottom flask, was placed a mixture of 3-fluoroanilline (48.0 g, 0.432 mol, 1.00 equiv) and dichloromethane (440 mL). Pyridine (85.8 mL, 1.08 mol, 2.50 equiv) and 3-chloropropionyl chloride (49.5 mL, 0.518 mol, 1.20 equiv) were added dropwise in turn. The reaction mixture was stirred for 3 hours at room temperature until the starting material disappeared as shown by TLC analysis. The reaction mixture was then diluted with water (440 mL) and extracted with ethyl acetate (2.2 L×3). The combined organic layer was washed with brine (1.0 L×2), dried over anhydrous sodium sulfate and concentrated in vacuum to provide 64.0 g (75%) of 3-chloro-N-(3-fluorophenyl)propanamide as a light brown solid. LC-MS (ES) [M+1]⁻ m/z: 202.1.

7-Fluoro-3,4-dihydroquinolin-2(1H)-one: Into a 1-L round-bottomed flask was placed a mixture of 3-chloro-N-(3-fluorophenyl)propanamide (64.0 g, 0.317 mol, 1.00 equiv) and aluminum trichloride (148 g, 1.11 mol, 3.50 equiv). The reaction mixture was stirred for 2 hours at 120° C.-125° C. until the starting material disappeared, as shown by TLC analysis. The reaction mixture was poured into iced water (1.2 L) and filtered. The filter cake was collected and washed with water (60 mL×3) and methyl tert-butyl ether (60 mL×3). This resulted in 47.8 g (91%) of 7-fluoro-3,4-dihydroquinolin-2(1H)-one as a light brown solid. LC-MS (ES) [M+1]⁺ m/z: 166.1.

7-Fluoro-6-nitro-3,4-dihydroquinolin-2(1H)-one: Into a 2-L round-bottomed flask, was placed a mixture of 7-fluoro-3,4-dihydroquinolin-2(1H)-one (47.8 g, 0.289 mol, 1.00 equiv) and concentrated sulfuric acid (290 ml). Nitric acid (20.8 mL, 0.304 mol, 1.05 equiv) was added dropwise. The reaction mixture was stirred for 2 hours at 0° C. until the starting material had disappeared, as shown by TLC analysis. The reaction mixture was poured into ice/water (600 mL) and filtered. The filter was collected and washed with water (60 mL×3) and methyl tert-butyl ether (60 mL×3). This resulted in 37.0 g (crude) of 7-fluoro-6-nitro-3,4-dihydroquinolin-2(1H)-one as a light brown solid. LC-MS (ES) [M+1]+m/z: 211.1. ¹H NMR (DMSO-d₆, 300 MHz) was consistent with a compound having the structure of 7-fluoro-6-nitro-3,4-dihydroquinolin-2(1H)-one.

6-Amino-7-fluoro-3,4-dihydroquinolin-2(1H)-one: Into a 3-L round-bottomed flask was placed a mixture of 7-fluoro-6-nitro-3,4-dihydroquinolin-2(1H)-one (37.0 (crude), 0.176 mol, 1.00 equiv), methanol (1800 ml) and Pd/C (3.70 g). The reaction mixture was stirred under hydrogen atmosphere for 4 hours at room temperature until the starting material had disappeared, as shown by TLC analysis. The reaction mixture was filtered and the filtrate was concentrated. The residue was purified by column chromatography silica gel (DCM/MeOH=200/1). This resulted in 12.1 g (two steps 24%) of 6-amino-7-fluoro-3,4-dihydroquinolin-2(1H)-one as an orange solid. LC-MS (ES) [M+1]⁺ m/z: 211.1.

N-(7-Fluoro-2-oxo-1,2,3,4-tetrahydroquinolin-6-yl)isonicotinamide (MBE1.2): Into a 40-mL vial was placed a mixture of 6-amino-7-fluoro-3,4-dihydroquinolin-2(1H)-one (180 mg, 1.00 mmol, 1.00 equiv), N,N-dimethylformamide (5 mL), isonicotinic acid (135 mg, 1.10 mmol, 1.10 equiv), N-ethyl-N-isopropylpropan-2-amine (387 mg, 3.00 mmol, 3.00 equiv) and 1-((dimethylamino)(dimethyliminio)methyl)-1H-[1,2,3]triazolo[4,5-b]pyridine 3-oxide hexafluorophosphate(V) (570 mg, 1.50 mmol, 1.50 equiv). The reaction mixture was stirred for 2 hours at room temperature. The reaction mixture was filtered and the filtrate was purified by prep-HPLC. This resulted in 175 mg (61%) of N-(7-fluoro-2-oxo-1,2,3,4-tetrahydroquinolin-6-yl)isonicotinamide as an off-white solid. LC-MS (ES) [M+1]⁺ m/z: 286.0. ¹H NMR (DMSO-d₆, 300 MHz) was consistent with a compound having the structure of N-(7-fluoro-2-oxo-1,2,3,4-tetrahydroquinolin-6-yl)isonicotinamide.

Synthesis of 6-((3-Ethylpyridin-4-yl)methylamino)-7-fluoro-3,4-dihydroquinolin-2(1H)-one (MBE1.3)

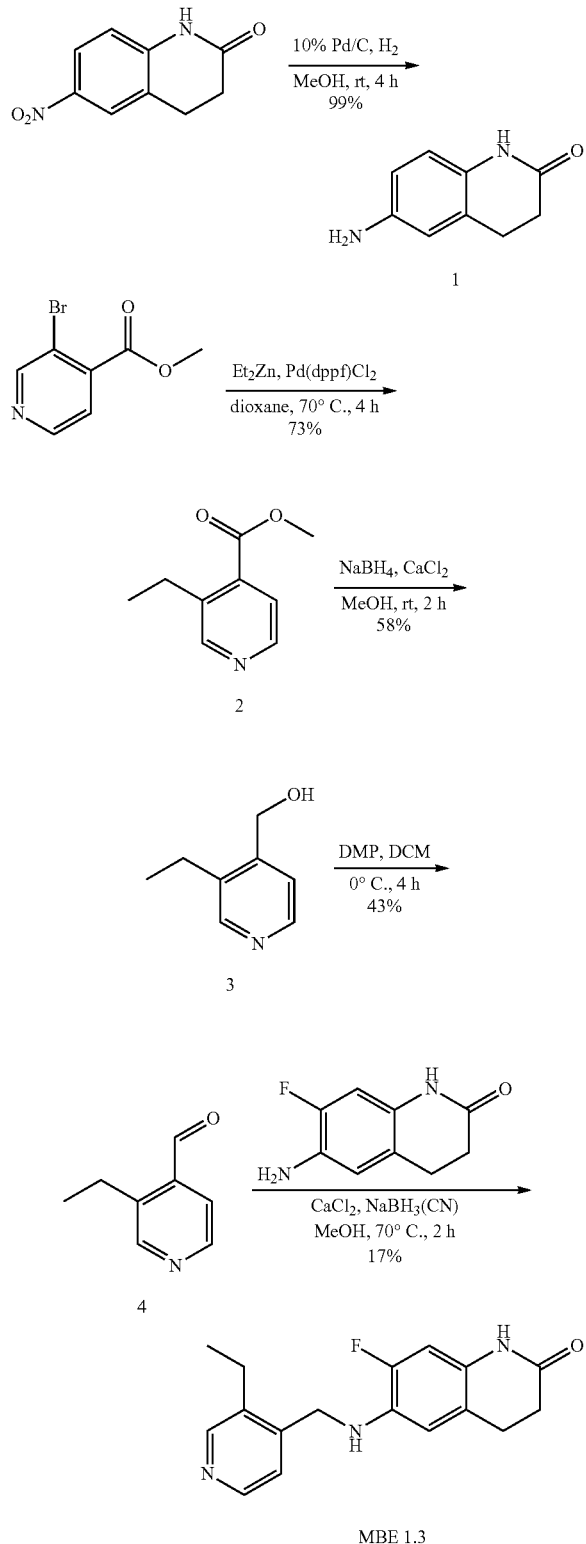

MBE 1.3

6-Amino-3,4-dihydroquinolin-2(1H)-one: Into a 100-mL round-bottomed flask was placed a mixture of 6-nitro-3,4-dihydroquinolin-2(1H)-one (1.92 g, 10.0 mmol, 1.00 equiv), methanol (50 mL) and Pd/C (200 mg). The reaction mixture was stirred under hydrogen atmosphere for 4 hours at room temperature until the starting material had disappeared, as shown by TLC analysis. The reaction mixture was filtered and the filtrate was concentrated. This resulted in 1.60 g (99%) of 6-amino-3,4-dihydroquinolin-2(1H)-one as a light green solid. LC-MS (ES) [M+1]+m/z: 163.1.

Methyl 3-ethylisonicotinate: Into a 1-L 3-necked round-bottomed flask was placed a mixture of methyl 3-bromoisonicotinate (21.6 g, 100 mmol, 1.00 equiv), dioxane (300 mL) and Pd(dppf)Cl$_2$ (3.66 g, 5.00 mmol, 0.05 equiv). A solution of diethylzinc in toluene (100 mL, 100 mmol, 1.00 equiv) was added dropwise at room temperature. The reaction mixture was stirred under nitrogen atmosphere for 4 hours at 70° C. The reaction mixture was poured into water (100 mL), extracted with ethyl acetate (200 mL×3). The organic layer was dried over anhydrous sodium sulfate, filtered and concentrated under vacuum. The residue was purified by silica gel flash eluted with PE/EtOAc (10/1) to provide 12.0 g (73%) of methyl 3-ethylisonicotinate as a light yellow liquid. LC-MS (ES) [M+1]$^+$ m/z: 166.0.

(3-Ethylpyridin-4-yl)methanol: Into a 100-mL round-bottomed flask was placed a mixture of methyl 3-ethylisonicotinate (3.75 g, 22.7 mmol, 1.00 equiv), methanol (50 mL) and calcium chloride (2.52 g, 22.7 mmol, 1.00 equiv). Sodium borohydride (1.72 g, 45.5 mol, 2.00 equiv) was added in portions at 0° C. The reaction mixture was stirred for 2 hours at room temperature until the starting material had disappeared, as shown by TLC analysis. The reaction mixture was poured into water (50 mL), extracted with ethyl acetate (100 mL×3). The organic layer was dried over anhydrous sodium sulfate, filtered and concentrated. This resulted in 1.80 g of (3-ethylpyridin-4-yl)methanol as a white solid. LC-MS (ES) [M+1]+m/z: 138.1.

3-Ethylisonicotinaldehyde: Into a 100-mL round-bottomed flask was placed a mixture of (3-ethylpyridin-4-yl)methanol (823 mg, 6.00 mol, 1.00 equiv), dichloromethane (25 ml) and DIVIP (510 mg, 7.20 mol, 1.20 equiv). The reaction mixture was stirred for 4 hours at room temperature until the starting material had disappeared as shown by TLC analysis. The reaction mixture was diluted with dichloromethane (25 ml) and washed with sodium bicarbonate saturated solution (25 ml×3). The organic layer was dried by hydrous sodium sulfate, filtered and concentrated. The residue was purified by column chromatography silica gel (PE/EtOAc=3/1). This resulted in 350 mg (43%) of 3-ethylisonicotinaldehyde as an orange solid. LC-MS (ES) [M+1]$^+$ m/z: 136.1.

6-((3-Ethylpyridin-4-yl)methylamino)-7-fluoro-3,4-dihydroquinolin-2(1H)-one: Into a 40-mL vial was placed a mixture of 6-amino-7-fluoro-3,4-dihydroquinolin-2(1H)-one (252 mg, 1.40 mmol, 1.00 equiv), methanol (5 ml), 3-ethylisonicotinaldehyde (189 mg, 1.00 mmol, 1.00 equiv), calcium chloride (776 mg, 6.99 mmol, 5.00 equiv) and sodium cyanoborohydride (132 mg, 1.50 mmol, 2.10 equiv). The reaction mixture was stirred for 2 hours at 70° C. The reaction mixture was filtered and the filtrate was purified by prep-HPLC. This resulted in 69.9 mg (17%) of 6-((3-ethylpyridin-4-yl)methylamino)-7-fluoro-3,4-dihydroquinolin-2(1H)-one as an off-white solid. LC-MS (ES) [M+1]$^+$ m/z: 300.1. $^1$H NMR (DMSO-d$_6$, 300 MHz) was consistent with a compound having the structure of 6-((3-ethylpyridin-4-yl)methylamino)-7-fluoro-3,4-dihydroquinolin-2(1H)-one.

Synthesis of 2-Ethyl-N-(7-fluoro-2-oxo-1,2,3,4-tetrahydroquinolin-6-yl)benzamide (MBE1.5)

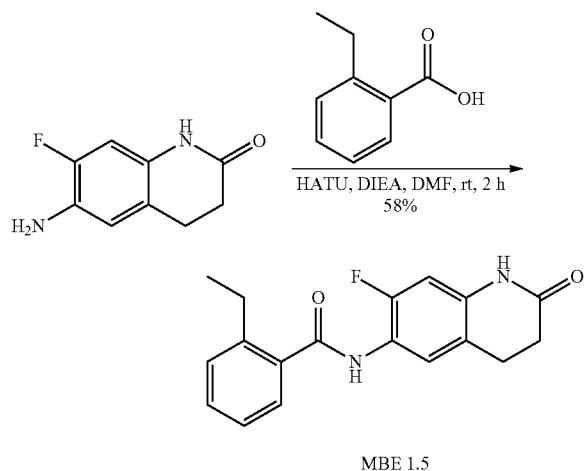

MBE 1.5

2-Ethyl-N-(7-fluoro-2-oxo-1,2,3,4-tetrahydroquinolin-6-yl)benzamide: Into a 40-mL vial was placed a mixture of 6-amino-7-fluoro-3,4-dihydroquinolin-2(1H)-one (180 mg, 1.00 mmol, 1.00 equiv), N,N-dimethylformamide (5 mL), 2-ethylbenzoic acid (135 mg, 1.10 mmol, 1.10 equiv), N-ethyl-N-isopropylpropan-2-amine (387 mg, 3.00 mmol, 3.00 equiv) and 1-((dimethylamino)(dimethyliminio)methyl)-1H-[1,2,3]triazolo[4,5-b]pyridine 3-oxide hexafluorophosphate(V) (570 mg, 1.50 mmol, 1.50 equiv). The reaction mixture was stirred for 2 hours at room temperature. The reaction mixture was filtered and the filtrate was purified by prep-HPLC. This resulted in 181 mg (58%) of 2-ethyl-N-(7-fluoro-2-oxo-1,2,3,4-tetrahydroquinolin-6-yl)benzamide as an off-white solid. LC-MS (ES) $[M+1]^+$ m/z: 313.1. $^1$H NMR (DMSO-$d_6$, 300 MHz) was consistent with a compound having the structure of 2-ethyl-N-(7-fluoro-2-oxo-1,2,3,4-tetrahydroquinolin-6-yl)benzamide.

Synthesis of 3-Ethyl-N-(2-oxo-1,2,3,4-tetrahydroquinolin-6-yl)isonicotinamide (MBE1.6)

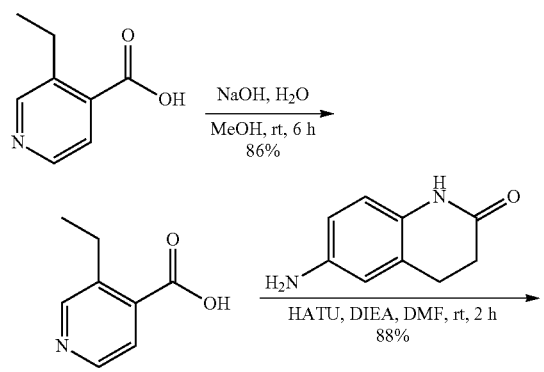

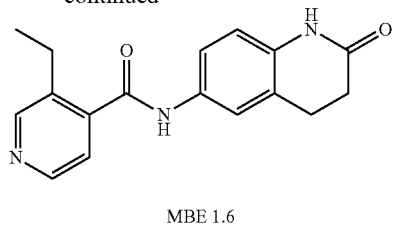

MBE 1.6

3-Ethylisonicotinic acid: Into a 100-mL round-bottomed flask was placed a mixture of methyl 3-ethylisonicotinate (3.30 g, 20.0 mmol, 1.00 equiv), methanol (20 mL), water (4 ml) and sodium hydroxide (1.60 g, 40.0 mmol, 2.00 equiv). The reaction mixture was stirred for 6 hours at room temperature. The pH was adjusted to a pH of approximately 4 with 2 M hydrochloric acid solution. The mixture was filtered and the filter cake was collected. This resulted in 2.60 g (86%) of 3-ethylisonicotinic acid as a white solid. LC-MS (ES) [M+1]+m/z: 152.0.

3-Ethyl-N-(2-oxo-1,2,3,4-tetrahydroquinolin-6-yl)isonicotinamide: Into a 40-mL vial was placed a mixture of 6-amino-7-fluoro-3,4-dihydroquinolin-2(1H)-one (180 mg, 1.00 mmol, 1.00 equiv), N,N-dimethylformamide (5 mL), 3-ethylisonicotinic acid (166 mg, 1.10 mmol, 1.10 equiv), N-ethyl-N-isopropylpropan-2-amine (387 mg, 3.00 mmol, 3.00 equiv) and 1-((dimethylamino)(dimethyliminio)methyl)-1H-[1,2,3]triazolo[4,5-b]pyridine 3-oxide hexafluorophosphate(V) (570 mg, 1.50 mmol, 1.50 equiv). The reaction mixture was stirred for 2 hours at room temperature. The reaction mixture was filtered and the filtrate was purified by prep-HPLC. This resulted in 260 mg (88%) of 3-ethyl-N-(2-oxo-1,2,3,4-tetrahydroquinolin-6-yl)isonicotinamide. LC-MS (ES) [M+1]+m/z: 296.1. $^1$H NMR (DMSO-$d_6$, 300 MHz) was consistent with a compound having the structure of 3-ethyl-N-(2-oxo-1,2,3,4-tetrahydroquinolin-6-yl)isonicotinamide.

Cell Lines and Cell Culture

MDA-MB-468, MCF7, 293T, B16F10, HCT116, HepG2, LN229, HTB140 and SW480 cells were cultured in DMEM+10% FBS; DU145 cells and its derivatives, PC3, AsPC-1, NCI-H358 were cultured in RPMI-1640+10% FBS; and SUM159 cells and its derivatives were cultured in F12 media supplemented with 10% FBS, 10 μg/mL Insulin and 20 ng/mL EGF. Cell lines were labeled with retroviral vectors with bi-cistronic expression of GFP/firefly luciferase to facilitate imaging and flow cytometry experiments. All cell lines were verified negative for mycoplasma contamination by monthly PCR analysis. No cells lines used here appear in the database of commonly misidentified cell lines (ICLAC). All cell lines were validated with STR analysis and compared to NCBI repository data.

Cloning, Viral Production, and Transduction

The coding sequences of Aldh1a1, Aldh1a2, Aldh1a3 and Aldh3a1 were cloned from cDNA made from pooled human reference RNA samples. Cloned sequences flanked by Age1 and Xho1 restriction sites were inserted into the pLex lentiviral plasmid. Clones were sequenced and compared against NCBI expressed sequence tags (ESTs) for accuracy. Viral production of each enzyme was performed by transfection into the 293T packaging cell line using PEI along with PsPax2 and VSVG packaging vectors. Viruses were collected and filtered at 0.45 μm, then cells were transduced using polybrene (8 μg/mL) for 12 hours, followed by culture with 1 μg/mL puromycin for the duration of experiments. All viral transduction and selection was performed on a cell population-wide basis.

ALDH1a3 in Development and Adult Physiology; Mechanism of Action

While certain enzymes within the ALDH family have well-characterized substrate preferences, regulation, and function, most members of this family are either poorly studied or the main mechanism of action is not understood. For example, it has been shown how ALDH1L1 and ALDH1L2 function in folate metabolism by oxidizing 10-formyl-THF. Another key example of a well-characterized Aldh enzyme is ALDH3a1, which constitutes 50% of soluble corneal protein and functions to protect against UV-induced oxidative damage of the retina and cornea by oxidizing 4-hydroxynonenal. Perhaps the most studied ALDH enzyme is ALDH2, the key catalyzer of acetylaldehyde oxidation to acetic acid in liver mitochondria. ALDH2 is inhibited by ANTABUSE® (disulfiram), a therapy given to alcoholics to prevent substance abuse. On the other hand, the ALDH1a subfamily has shown broad significance across developmental biology and various pathologies, yet its mechanism of action and key regulators remain to be elucidated.

The ALDH1a sub-family is the most biologically significant group among the ALDH family, and has recently become the focus of considerable research given its importance to developmental biology and the notable ability of the ALDEFLUOR™ assay (Stem Cell Technology) to identify stem cells, particularly in cancer. As described herein, the ALDEFLUOR™ assay predominantly measures activity from ALDH1a3.

Total knockout of ALDH1a3 results in postnatal mouse death due to nasal closure defects. Importantly, this phenotype can be rescued by all-trans retinoic acid supplementation during a short window of pregnancy, resulting in normal adults. In humans, homozygous mutations in ALDH1a3 are associated with small-eye disease, but this phenotype is not fully penetrant and additional pathologies were not mentioned. Further supporting the idea that ALDH1a3 is developmentally restricted, recent studies have shown that ALDH1a3 is specifically repressed in certain developmental tissues to prevent vitamin A signaling. Additional analyses have shown ALDH1a3 is not needed for the developing ovary, and it is expressed only in the prostate and salivary gland of adults. Among the colon, liver, lung, bladder, prostate and ovary, only the ovary has a significant ALDEFLUORm-positive population, and this small population is only partially inhibited by an ALDH1a3 inhibitor.

In metabolic disease, ALDH1a3 is a marker of failing pancreatic islet cells. Additional research indicates that ALDH1a3 expression directly reduces insulin secretion by pancreatic islet cell clones while increasing glucagon secretion. This suggests that ALDH1a3 can also drive the pathology of Type 2 diabetes.

Taken together, these results suggest that ALDH1a3 could potentially be ablated without significant on-target toxicity. Data indicate that ALDH1a3 is dispensable to adult mammals. Inhibition of ALDH1a3 during pregnancy would likely be contraindicated.

Published research has predominantly claimed two mechanisms for the cancer-promoting effect of ALDH1a3. These are split between the detoxification of reactive oxygen species or the oxidation of retinal into bioactive retinoic acid. Multiple reasons exist for the discrepancy between the number of papers detailing the functional consequence of ALDH1a3 expression compared to its mechanism of action. Primarily, reactive oxygen species are transient and difficult to detect. Current methods use fluorescent reporters, such as DCFDA and DHE, both of which are insensitive. Furthermore, oxidative stress in in vitro conditions is not reflective of the in vivo condition. There have been attempts to induce oxidative stress in vitro with paclitaxel and detect via DCFDA, however, the detection range for this assay is smaller than the deviations inherent within the data. However, additional literature evidence does support a ROS-related mechanism: ALDH1a3 was found to detoxify 4-HNE in stallion sperm samples, which led to improved motility. ALDH1a3 was also induced by radiotherapy in head and neck squamous cell carcinoma (SCC), indicating it may respond to cellular damage.

Interestingly, high profile work in melanoma has demonstrated that oxidative stress is the major determinant of metastatic dissemination. In this work, it was shown that oxidative stress is not present in a primary tumor, whereas it was dramatically induced and affected the fitness of metastatic cells. Systemic antioxidant delivery could then facilitate lung metastasis in normally non-metastatic cells. Manipulation of ALDH1a3 expression does not strongly affect primary tumor growth until challenged with an oxidative stressor, such as chemotherapy. On the other hand, it has been observed that the greatest effect of ALDH1a3 inhibition is on lung or bone metastasis, sites with high levels of oxidative stress (FIGS. 5A-6B).

Studies of retinoic acid (RA) signaling dependent on ALDH1a3 are equally difficult, as they require exogenous supplementation with retinal in tissue culture conditions and are far removed from the microenvironmental conditions of the tumor. Data showing gene correlations between each of the ALDH1a enzymes and each component of the RA signaling pathway in tumors from breast cancer patients has been developed, and demonstrates that of ALDH1a1, ALDH1a2 and ALDH1a3, ALDH1a3 shows the least correlation with components of the RA signaling pathway in breast tumors. Furthermore, if ALDH1a3 were influencing the RA signaling pathway, it would be expected that tissue culture growth or primary tumor growth would be affected. No differences in primary tumor or in vitro growth have been observed in studies on breast cancer cells.

The functional importance of ALDH1a3 to therapeutic resistance, tumor progression and metastasis across most solid tumor types makes it an appealing target for drug discovery. Coupled with the low chance for on-target toxicity, systemic pharmacological inhibition of ALDH1a3 alone or in combination with other therapeutics (e.g., approved therapeutics) is expected to be useful for treating primary cancers, as well as indolent and overt metastatic disease.

ALDEFLUOR™ Assay

The ALDEFLUOR™ assay assesses the ability of cells to oxidize bodipy-aminoacetaldehyde (BAAA) to bodipy-aminoacetate (BAA), which spontaneously esterifies to form a non-cell membrane permeable product. This activity can be used to sort live cells and thereby discriminate between ALDH activity levels within heterogenous populations. When it was first discovered in 2007 that ALDEFLUOR™-positive cancer cells were more tumorigenic and predicted worse clinical outcome, it was assumed that ALDEFLUOR™ activity was a marker of a broader transcriptional program that promoted tumor aggressiveness. Since these early studies, ALDEFLUOR™ activity has become the most cited method for assessing the "stemness" or aggressiveness of tumor cell populations.

Following this seminal discovery, ALDEFLUOR™ activity was often assessed with little consideration for the function of ALDH1 enzymes. Rather, publications showed that the ALDEFLUOR™ assay isolated aggressive or metastatic cancer cells, regardless of the site of the primary tumor. Since, hundreds of papers have used the ALDEFLUOR™ assay in assessing cancer cell traits across almost all cancer types. Only beginning with Marcato and colleagues in 2011 was it shown that ALDH1a3 is responsible for ALDEFLUOR™ activity in most breast cancer cell lines.

Since Marcato's and colleagues' publication, an accelerating rate of emerging studies has established that ALDH1a3 is not only responsible for ALDEFLUOR™ activity across most cancer types, but that it also functionally promotes cancer growth, therapeutic resistance, and metastasis. Research of varying quality has established that ALDH1a3 is expressed and important for growth in melanoma patient-derived xenografts or cell lines, metabolism, chemoresistance and radioresistance in mesenchymal-like glioma or glioblastoma, tumorigenicity and cisplatin resistance in lung cancer, growth and radioresistance in pancreatic cancer, FAK inhibitor resistance in colon and thyroid cells, cisplatin resistance in mesothelioma, Gleason score and growth in prostate cancer, apoptosis-resistance and metastasis in breast cancer and prognosis in cholangiocarcinoma. It is shown herein that ALDH1a3 is the dominant ALDEFLUOR™-inducing enzyme across most solid tumor types (see FIGS. 3A and 3B).

Expression and prognosis studies have further shown that ALDH1a3 is strongly predictive of poor outcomes across cancer types. Hypermethylation of the ALDH1a3 promoter leading to lower ALDH1a3 expression was the strongest predictor of favorable outcome in a set of primary glioblastoma patients. High ALDH1a3 predicted lymph node metastasis in cholangiocarcinoma patients. ALDH1a3 expression is driven by androgen in prostate cancer, where androgen is the major mitogen for prostate cancer cells, while mir187 targets ALDH1a3 in prostate cancer and high mir187 was correlated to favorable prognosis.

In the ALDEFLUOR™ assay used herein, cells were grown until they reached 50-80% confluence, harvested with 0.25% Trypsin/EDTA (Sigma), and washed once with PBS by centrifugation/resuspension (190 g for 5 min at 4° C.). Cells were counted, centrifuged and resuspended at 1,000,000 cells/mL in ALDEFLUOR™ buffer (Stemcell Technologies). ALDEFLUOR™ substrate (Stemcell Technologies, 1:200) and test compound or 1 mM DEAB were added to cell suspension and incubated at 37° C. for 45 minutes with vortexing every 15 minutes. Cells were centrifuged and resuspended in ALDEFLUOR™ buffer with DAPI at 5 µg/mL. Samples were analyzed with the BD LSR2 flow cytometry platform. Gating was performed using DEAB as a negative control.

Figure 1A:
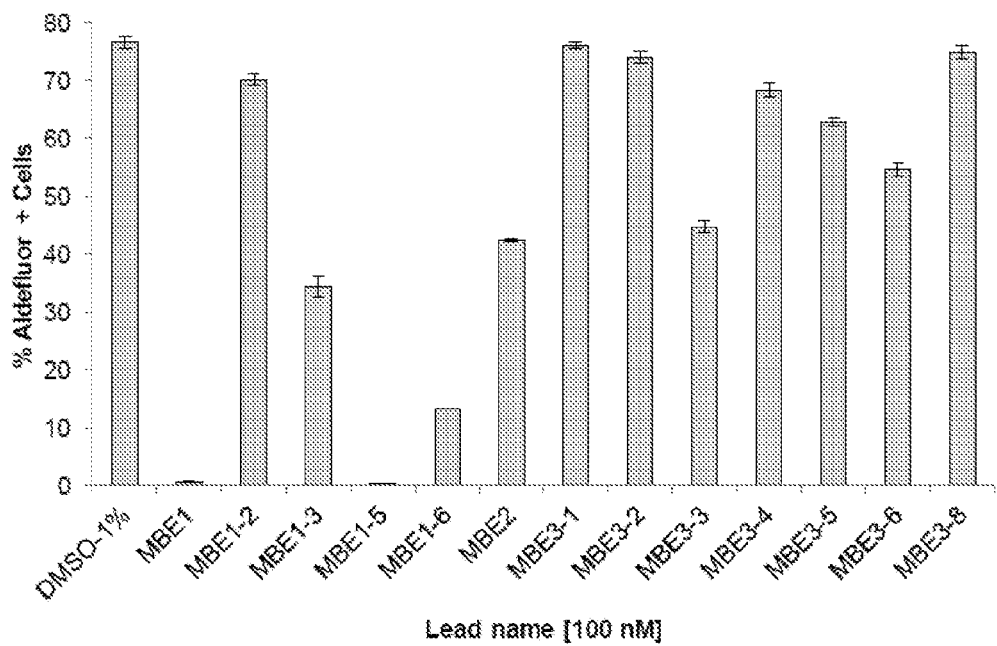
FIG. 1A is a bar graph of percentage of ALDEFLUOR™-positive cells in the presence of various compounds described herein, and shows the percentage of SUM159-M1a-Aldh1a3 cells that are above background fluorescence levels, as detected by flow cytometry after incubation using the standard ALDEFLUOR™ protocol described herein with compounds at a concentration of 100 nanomolar. Gating for background fluorescence was performed using 1 millimolar N,N-diethylaminobenzaldehyde (DEAB) as a negative control.

FIG. 1A is a bar graph of percentage of ALDEFLUOR™-positive cells in the presence of various compounds described herein, and shows the percentage of SUM159-Mla-Aldh1a3 cells that are above background fluorescence levels, as detected by flow cytometry after incubation using the standard ALDEFLUOR™ protocol described herein with compounds at a concentration of 100 nM. Gating for background fluorescence was performed using 1 millimolar DEAB as a negative control. FIG. 1A demonstrates that MBE1-5, MBE1 and MBE1-6 are high-affinity compounds for the inhibition of ALDH1a3 activity.

Figure 1B:
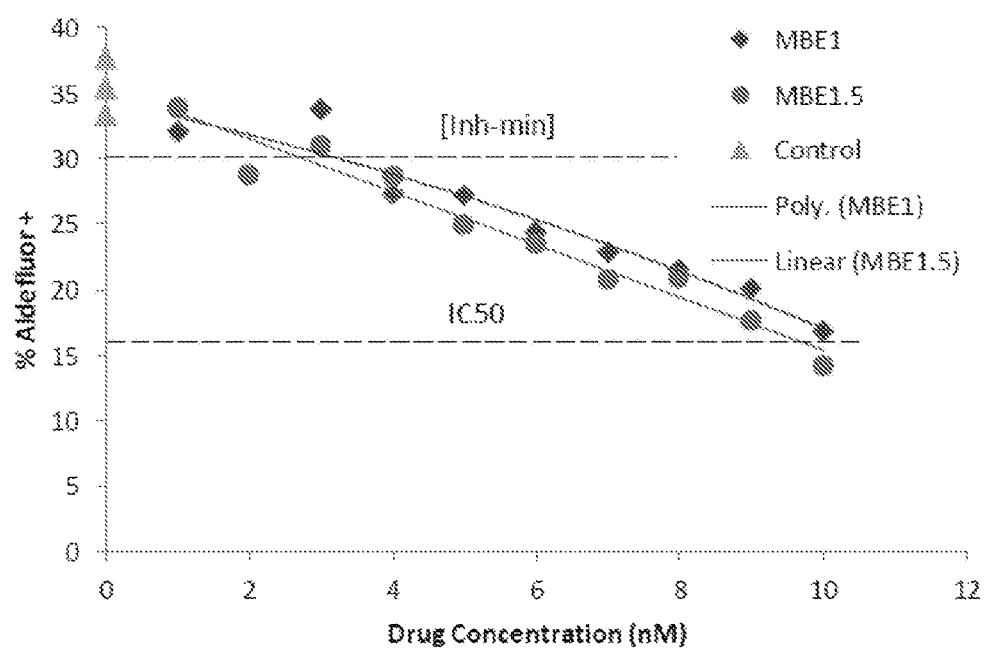
FIG. 1B is a line graph of percentage of ALDEFLUOR™-positive cells in the presence of varying concentrations of MBE1 or MBE1.5, and shows the percentage of SUM159-M1a-Aldh1a3 cells that are above background fluorescence levels, as detected by flow cytometry after incubation according to the standard ALDEFLUOR™ protocol described herein combined with a dose titration of MBE1 or MBE1-5. The [inh-min] threshold was set at the lower bound of two standard deviations of control samples, while the $IC_{50}$ threshold was set at 50% of the average of control samples.

FIG. 1B is a line graph of percentage of ALDEFLUOR™-positive cells in the presence of varying concentrations of MBE1 or MBE1-5, and shows the percentage of SUM159-Mla-Aldh1a3 cells that are above background fluorescence levels, as detected by flow cytometry after incubation according to the standard ALDEFLUOR™ protocol described herein combined with a dose titration of MBE1 or MBE1-5. The [inh-min] threshold was set at the lower bound of two standard deviations of control samples, while the $IC_{50}$ threshold was set at 50% of the average of control samples. FIG. 1B demonstrates that MBE1 and MBE1-5 show $IC_{50}$ values in the 8-10 nanomolar range with inhibitory activity detected at concentrations as low as 2 nanomolar.

Figure 1C:
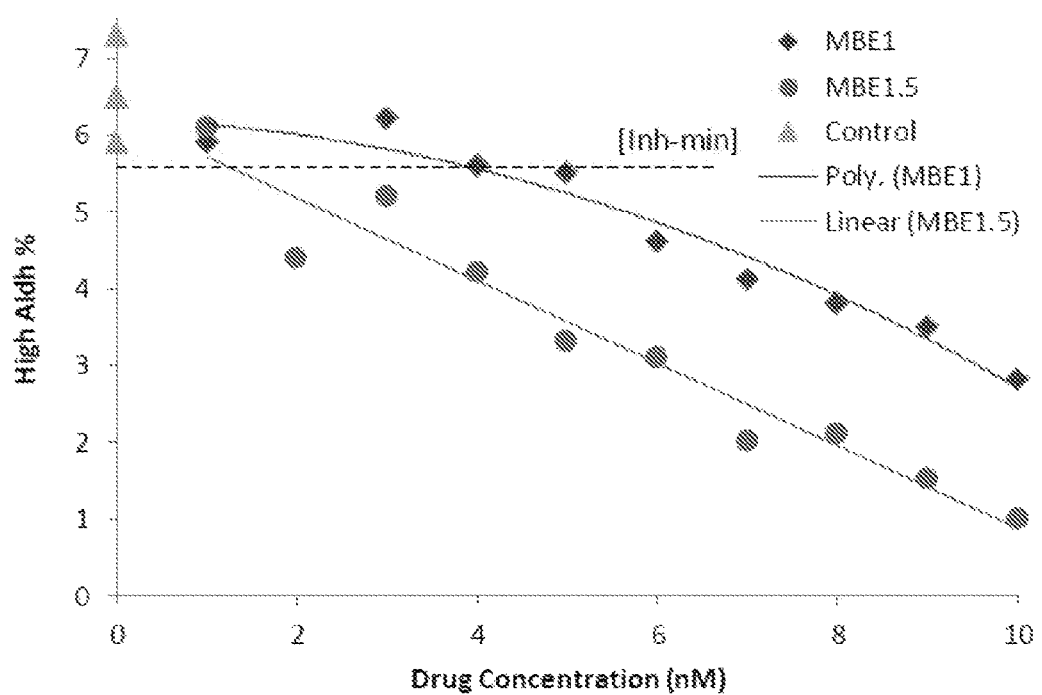
FIG. 1C is a line graph of high ALDH percentage in the presence of varying concentrations of MBE1 and MBE1.5, and shows the percentage of SUM159-M1a-Aldh1a3 cells that are at high fluorescence levels, as detected by flow cytometry after incubation according to the standard ALDE-FLUOR™ protocol described herein combined with a dose titration of MBE1 or MBE1.5. High activity was gated at the 99th percentile of cells at a MBE1.5 concentration of 10 nanomolar. The [inh-min] threshold was set at the lower bound of two standard deviations of control samples.

FIG. 1C is a line graph of high ALDH percentage in the presence of varying concentrations of MBE1 and MBE1.5, and shows the percentage of SUM159-Mla-Aldh1a3 cells that are at high fluorescence levels, as detected by flow cytometry after incubation according to the ALDEFLUOR™ protocol described herein combined with a dose titration of MBE1 or MBE1.5. High activity was gated at the 99th percentile of cells at a MBE1.5 concentration of 10 nanomolar. The [inh-min] threshold was set at the lower bound of two standard deviations of control samples. FIG. 1C demonstrates MBE1.5 is more adept at inhibiting highly ALDH1a3-active cells than MBE1.

Figure 2A:
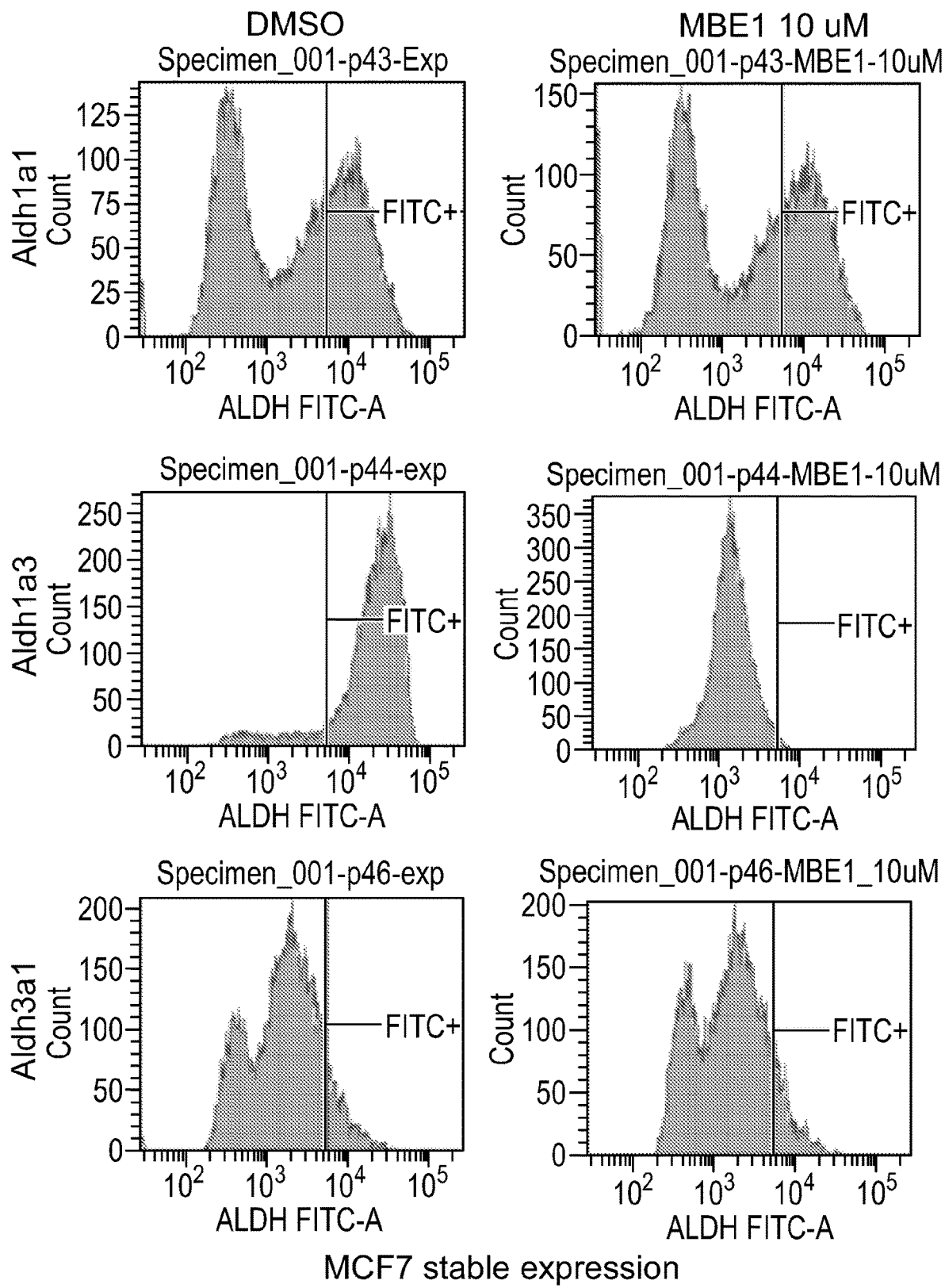
FIG. 2A is a histogram of MCF7 cells stably transduced with human Aldh1a1, Aldh1a3 or Aldh3a1 and analyzed using the ALDEFLUOR™ protocol by flow cytometry in combination with DMSO or MBE1 at the listed concentrations, and shows the effect of DMSO or MBE1 on the ALDEFLUOR™ activity induced by each enzyme.

FIG. 2A is a histogram of MCF7 cells stably transduced with human Aldh1a1, Aldh1a3 or Aldh3a1 and analyzed using the ALDEFLUOR™ protocol by flow cytometry in combination with DMSO or MBE1 at the listed concentrations, and shows the effect of DMSO or MBE1 on the ALDEFLUOR™ activity induced by each enzyme. FIG. 2A demonstrates that MBE1 does not inhibit Aldh1a1 or Aldh3a1 activity at concentrations below 10 µM while it is effective at inhibiting Aldh1a3 activity in a separate cancer cell line, MCF7.

Figure 2B:
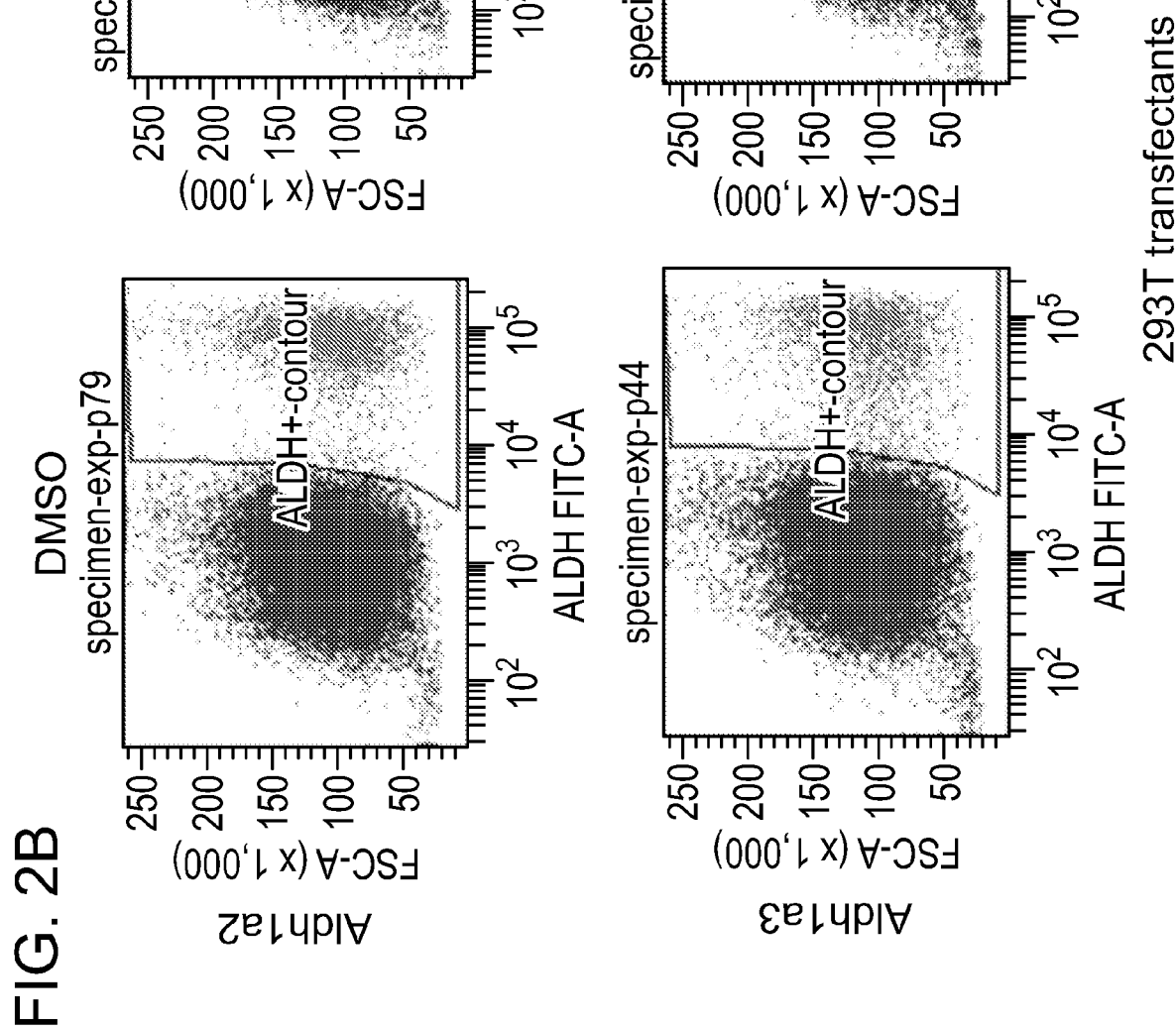
FIG. 2B is a histogram of 293T cells transiently transfected with human Aldh1a2 or Aldh1a3 and analyzed using the ALDEFLUOR™ protocol by flow cytometry in combination with DMSO or MBE1.5 at the listed concentrations, and shows the effect of either DMSO or MBE1.5 on the ALDEFLUOR™ activity induced by each enzyme.

FIG. 2B is a histogram of 293T cells transiently transfected with human Aldh1a2 or Aldh1a3 and analyzed using the ALDEFLUOR™ protocol by flow cytometry in combination with DMSO or MBE1.5 at the listed concentrations, and shows the effect of either DMSO or MBE1.5 on the ALDEFLUOR™ activity induced by each enzyme. FIG. 2B demonstrates that MBE1.5 does not inhibit Aldh1a2 activity at concentrations below 10 µM while it is effective at inhibiting Aldh1a3 activity in 293T cells transfected with human Aldh1a3.

Figure 3A:
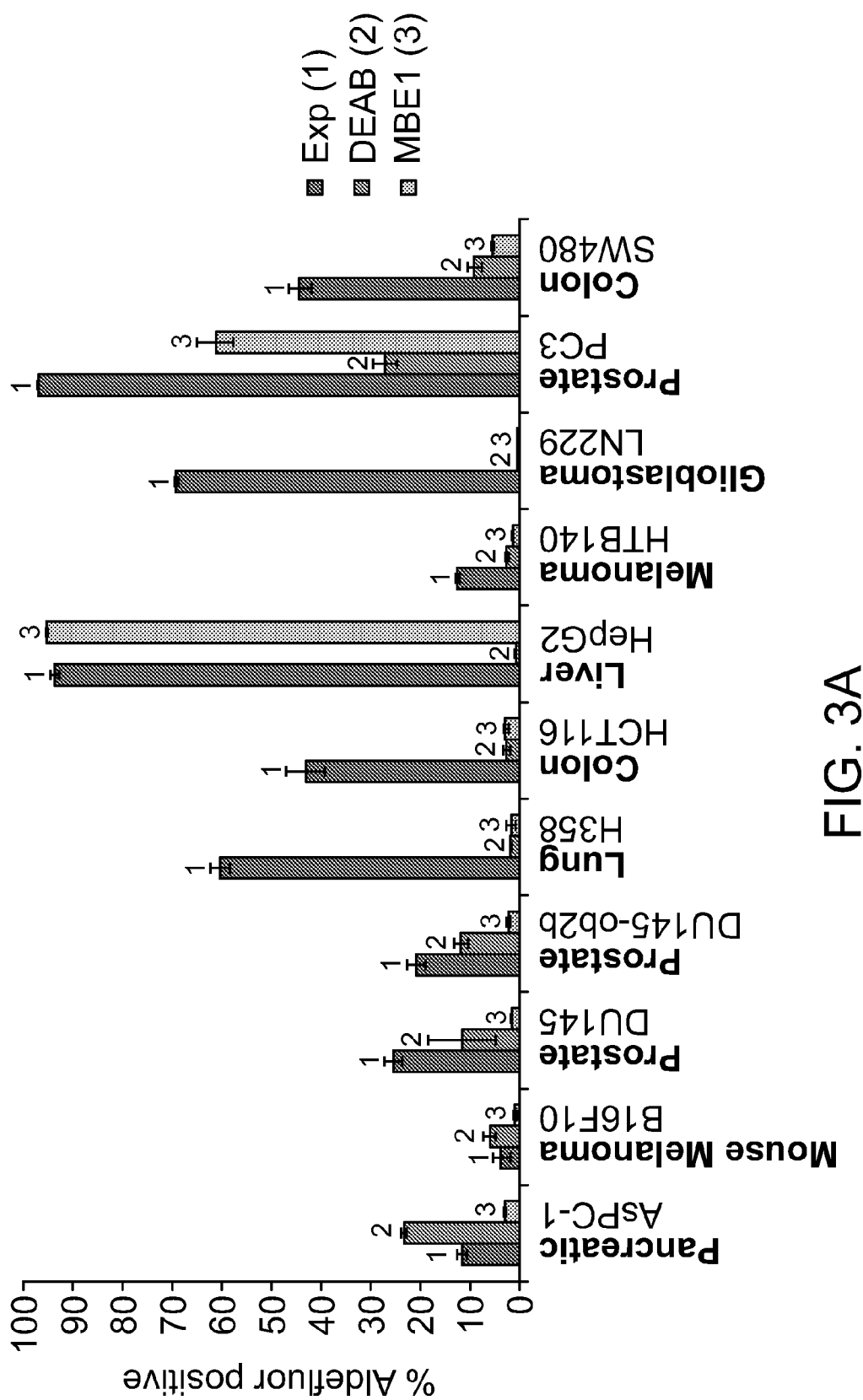
FIG. 3A is a bar graph of ALDEFLUOR™-positive cells in a variety of cancer types in the presence of DEAB or MBE1, and shows that ALDH1a3 activity is observed in many cancer types in addition to M1a (breast) and MDA-468 (breast), and inhibited by MBE1 in many cancer types.
Figure 3B:
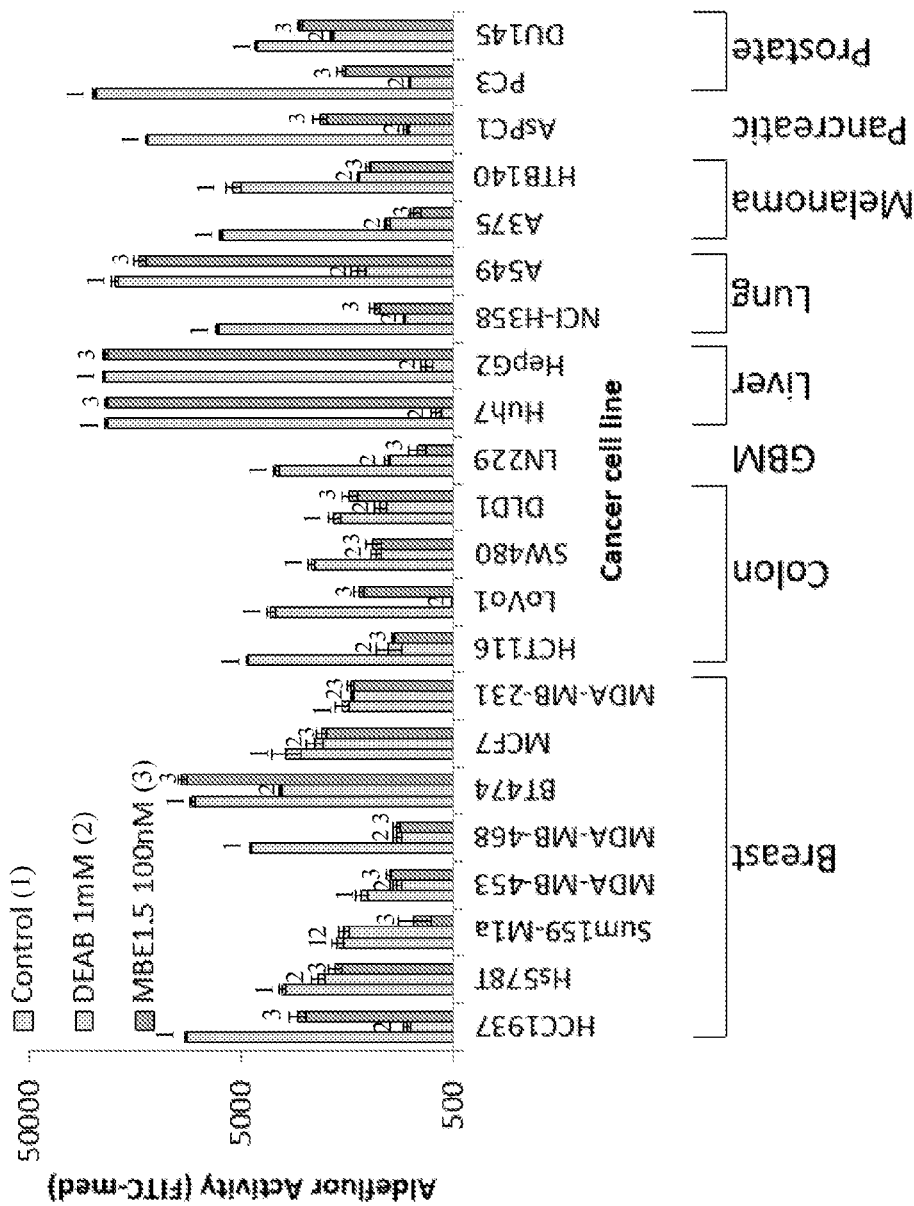
FIG. 3B is a bar graph of ALDEFLUOR™ activity in a variety of cancer types in the presence of 1 mM DEAB (a pan-ALDH inhibitor) or 100 nM MBE1.5 (a specific ALDH1a3 inhibitor), and shows that the majority of human cancer cell lines show Aldh1a3 activity.

FIG. 3A is a bar graph of ALDEFLUOR™-positive cells in a variety of cancer types in the presence of DEAB or MBE1, and shows that ALDH1a3 activity is observed in many cancer types in addition to Sum159-Mla (breast) and MDA-468 (breast), and inhibited by MBE1 in many cancer types. FIG. 3B is a bar graph of ALDEFLUOR™-positive cells in a variety of cancer types in the presence of 1 mM DEAB (a pan-ALDH inhibitor) or 100 nM MBE1.5 (a specific ALDH1a3 inhibitor), and shows that the majority of human cancer cell lines show ALDH1a3 activity. A notable exception is liver cancer, where it is expected that a large ALDEFLUOR™-positive population exists, and is driven by ALDH1a1.

An ALDEFLUOR™ assay was also used to assess the relative activity of several compounds described herein against SUM159-Mla-Aldh1a3 cells. The activity of several compounds in the assay at a concentration of 100 nM is reported in Table 1, along with the chemical structure and compound name associated with each compound.

TABLE 1

| Cmpd. No. | Compound Structure | Compound Name | Percent of Cells Positive for ALDEFLUOR™ at 100 nM | Inhibitory Activity at 100 nM (%) |
|---|---|---|---|---|
| MBE1 | 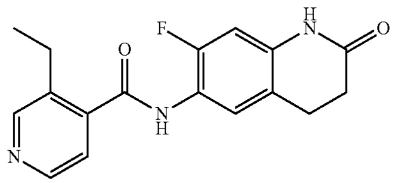 [SMILES: CCc1cnccc1C(=O)Nc1cc2c(cc1F)NC(=O)CC2] | 3-ethyl-N-(7-fluoro-2-oxo-1,2,3,4-tetrahydroquinolin-6-yl) isonicotinamide | 0.73 | 99 |
| MBE1.2 | 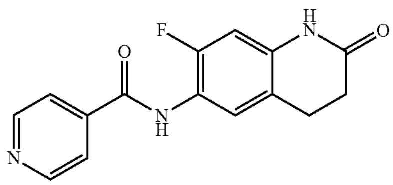 [SMILES: O=C1CCc2cc(NC(=O)c3ccncc3)c(F)cc2N1] | N-(7-fluoro-2-oxo-1,2,3,4-tetrahydroquinolin-6-yl) isonicotinamide | 70 | 8 |
| MBE1.3 | 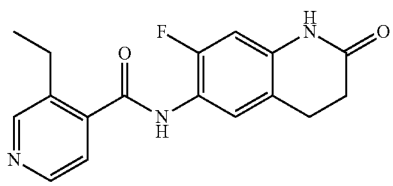 [SMILES: CCc1cnccc1C(=O)Nc1cc2c(cc1F)NC(=O)CC2] | 6-(((3-ethylpyridin-4-yl)methyl)amino)-7-fluoro-3,4-dihydroquinolin-2(1H)-one | 34 | 55 |
| MBE1.5 | 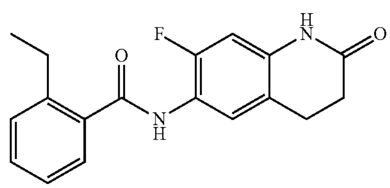 [SMILES: CCc1ccccc1C(=O)Nc1cc2c(cc1F)NC(=O)CC2] | 2-ethyl-N-(7-fluoro-2-oxo-1,2,3,4-tetrahydroquinolin-6-yl)benzamide | 0.03 | 100 |
| MBE1.5A | 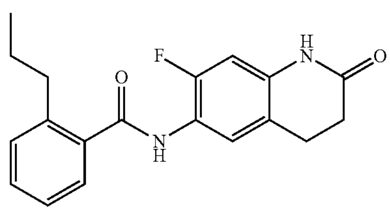 [SMILES: CCCc1ccccc1C(=O)Nc1cc2c(cc1F)NC(=O)CC2] | N-(7-fluoro-2-oxo-1,2,3,4-tetrahydroquinolin-6-yl)-2-propylbenzamide | | |
| MBE1.5B | 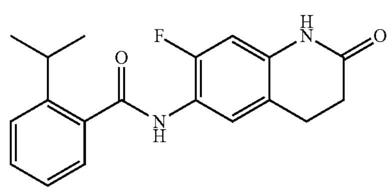 [SMILES: CC(C)c1ccccc1C(=O)Nc1cc2c(cc1F)NC(=O)CC2] | N-(7-fluoro-2-oxo-1,2,3,4-tetrahydroquinolin-6-yl)-2-isopropylbenzamide | | |
| MBE1.5C | 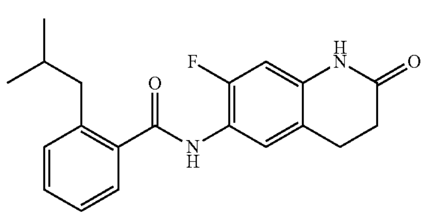 [SMILES: CC(C)Cc1ccccc1C(=O)Nc1cc2c(cc1F)NC(=O)CC2] | N-(7-fluoro-2-oxo-1,2,3,4-tetrahydroquinolin-6-yl)-2-isobutylbenzamide | | |

TABLE 1-continued

| Cmpd. No. | Compound Structure | Compound Name | Percent of Cells Positive for ALDEFLUOR™ at 100 nM | Inhibitory Activity at 100 nM (%) |
|---|---|---|---|---|
| MBE1.5D | 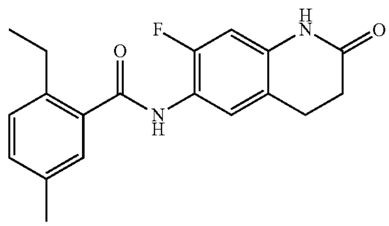 [SMILES: CCc1ccc(C)cc1C(=O)Nc1cc2c(cc1F)NC(=O)CC2] | 2-ethyl-N-(7-fluoro-2-oxo-1,2,3,4-tetrahydroquinolin-6-yl)-5-methylbenzamide | | |
| MBE1.6 | 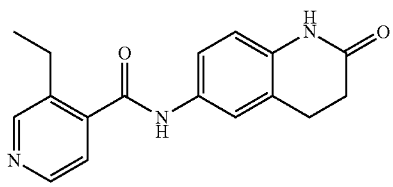 [SMILES: CCc1cnccc1C(=O)Nc1ccc2c(c1)CCC(=O)N2] | 3-ethyl-N-(2-oxo-1,2,3,4-tetrahydroquinolin-6-yl)isonicotinamide | 13 | 83 |
| MBE2 | 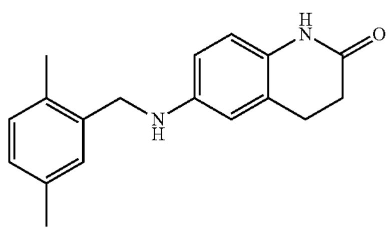 [SMILES: Cc1ccc(C)c(CNc2ccc3c(c2)CCC(=O)N3)c1] | 6-((2,5-dimethylbenzyl)amino)-3,4-dihydroquinolin-2(1H)-one | 42 | 45 |
| MBE3.1 | 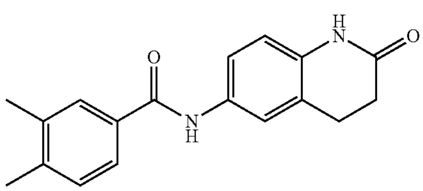 [SMILES: Cc1ccc(C(=O)Nc2ccc3c(c2)CCC(=O)N3)cc1C] | 3,4-dimethyl-N-(2-oxo-1,2,3,4-tetrahydroquinolin-6-yl)benzamide | 76 | 0.60 |
| MBE3.2 | 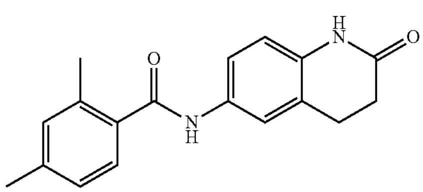 [SMILES: Cc1ccc(C(=O)Nc2ccc3c(c2)CCC(=O)N3)c(C)c1] | 2,4-dimethyl-N-(2-oxo-1,2,3,4-tetrahydroquinolin-6-yl)benzamide | 74 | 3.3 |
| MBE3.3 | 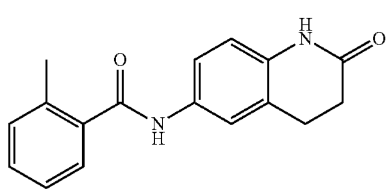 [SMILES: Cc1ccccc1C(=O)Nc1ccc2c(c1)CCC(=O)N2] | 2-methyl-N-(2-oxo-1,2,3,4-tetrahydroquinolin-6-yl)benzamide | 45 | 42 |
| MBE3.4 | 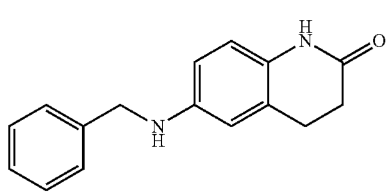 [SMILES: O=C1CCc2cc(NCc3ccccc3)ccc2N1] | 6-(benzylamino)-3,4-dihydroquinolin-2(1H)-one | 68 | 11 |

TABLE 1-continued

| Cmpd. No. | Compound Structure | Compound Name | Percent of Cells Positive for ALDEFLUOR™ at 100 nM | Inhibitory Activity at 100 nM (%) |
|---|---|---|---|---|
| MBE3.5 | 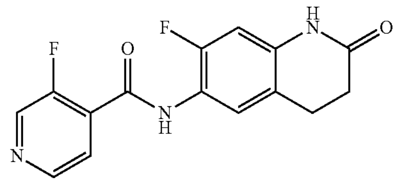 [SMILES: O=C1CCc2cc(NC(=O)c3ccncc3F)c(F)cc2N1] | 3-fluoro-N-(7-fluoro-2-oxo-1,2,3,4-tetrahydroquinolin-6-yl)isonicotinamide | 63 | 18 |
| MBE3.6 | 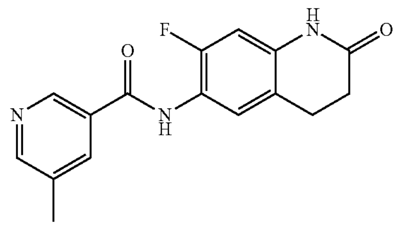 [SMILES: Cc1cncc(C(=O)Nc2cc3c(cc2F)NC(=O)CC3)c1] | N-(7-fluoro-2-oxo-1,2,3,4-tetrahydroquinolin-6-yl)-5-methylnicotinamide | 55 | 29 |
| MBE3.8 | 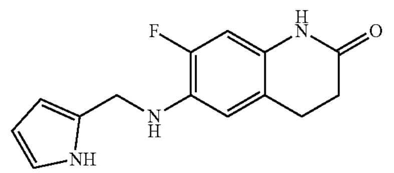 [SMILES: O=C1CCc2cc(NCc3ccc[nH]3)c(F)cc2N1] | 6-(((1H-pyrrol-2-yl)methyl)amino)-7-fluoro-3,4-dihydroquinolin-2(1H)-one | 75 | 2 |

FIG. 12 is a graph of ALDEFLUOR™ activity versus concentration, and shows the ALDEFLUOR™ activity of several compounds described herein against SUM159-M1a-Aldh1a3 cells at concentrations of 10 nM and 100 nM. In comparison to control (DMSO) or DEAB-treated cells, MBE 1.5C is nearly twice as potent as MBE 1.5, MBE 1.5A or MBE 1.5D at a concentration of 10 nM.

ALDH isoforms 1a1, 1a2, 1a3 and 3a1 were expressed in MCF7 or SUM159 cells, which were subsequently used in an ALDEFLUOR™ assay. FIG. 13A is a Western blot, and shows the expression of each ALDH isoform in the indicated cells. FIG. 13B is a line graph of percentage of ALDEFLUOR™-positive MCF7 cells expressing the indicated ALDH isoform versus the log of MBE 1.5 concentration, and shows that MBE 1.5 specifically inhibits ALDH1a3 at concentrations below 10 µM. FIG. 13C is a line graph of percentage of ALDEFLUOR™-positive SUM159 cells expressing the indicated ALDH isoform versus the log of MBE 1.5 concentration, and shows that MBE 1.5 specifically inhibits ALDH1a3 at concentrations below 10 µM.

Ex Vivo Analysis of ALDH Activity in Murine Lymphocytes

Bone marrow cells were collected from 12-week old C56BL6 mice via tibia and femur flush with PBS and were passed through a 100-µm cell sieve. Thymocytes and spleenocytes were isolated from corresponding tissues and were isolated by physical disruption against a 100 µm cell sieve. Cells were washed via centrifugation/resuspension and then suspended at $10^7$ cells/mL. The ALDEFLUOR™ assay with or without MBE1 was then conducted on these cells as described except with the addition of either anti-CDR (Biolegend #100308), anti-CD11c (BD Pharmigen #561119), anti-CD45 (eBioscience 30-F11), or anti-CD317 (Biolegend 129c1) during the incubation period at 1:200.

Figure 4A:
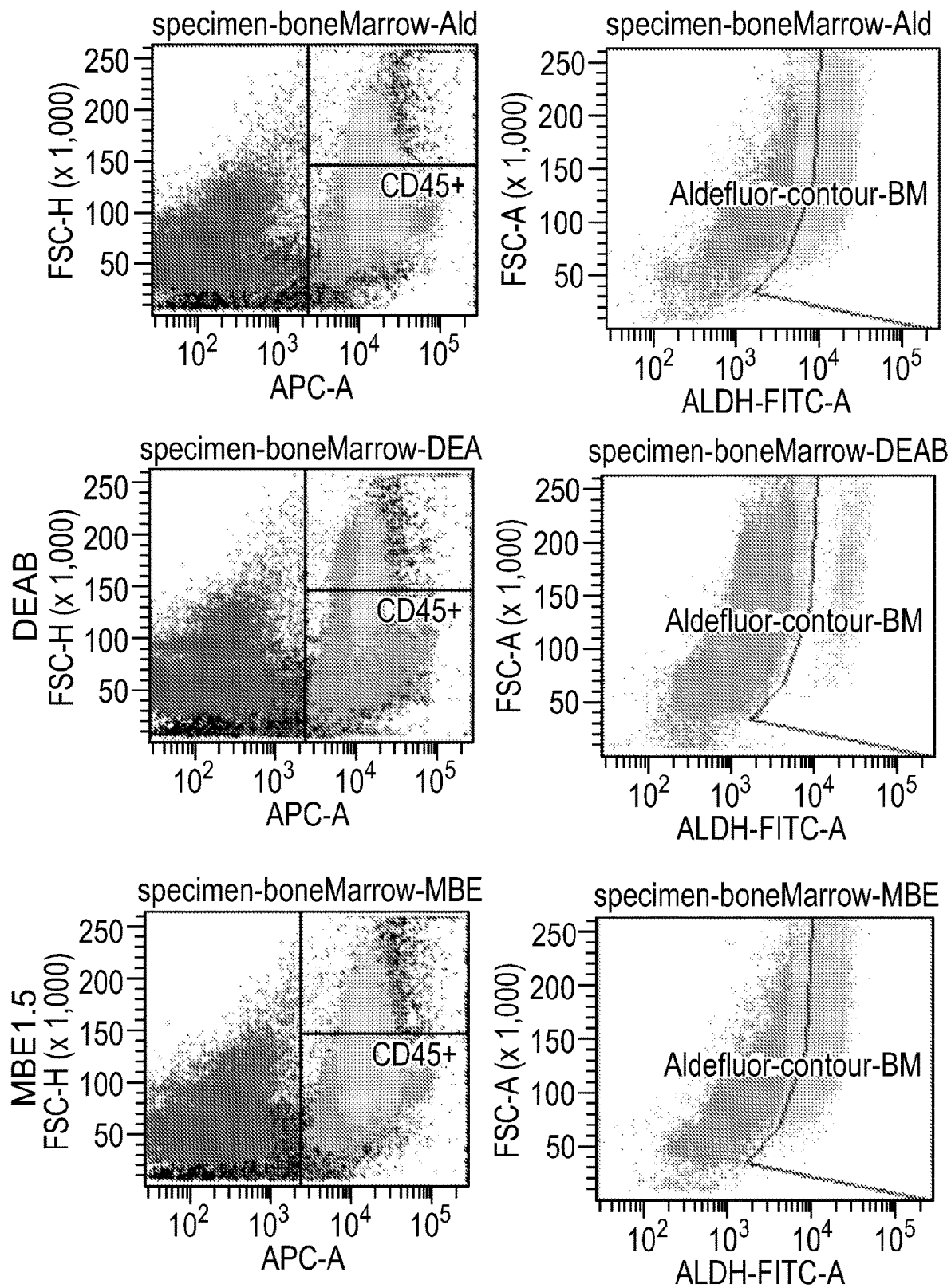
FIG. 4A is flow cytometry spectra, and shows that CD45-positive bone marrow cells are ALDEFLUOR®-positive, but are not affected by MBE1.5.
Figure 4B:
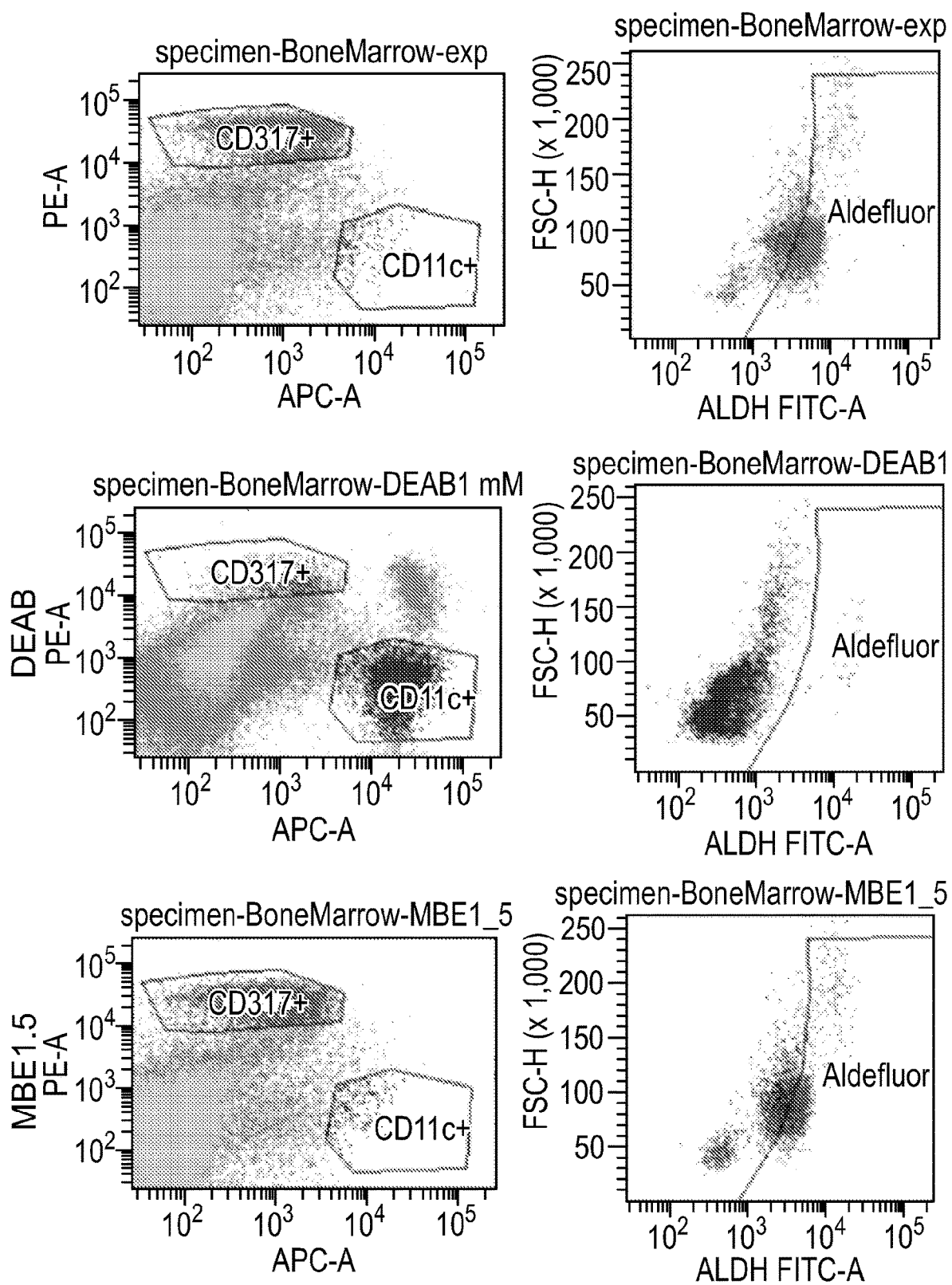
FIG. 4B is flow cytometry spectra, and shows that CD11c-positive bone marrow cells are ALDEFLUOR™-positive, but are not affected by MBE1.5

FIG. 4A is flow cytometry spectra, and shows that CD45-positive bone marrow cells are ALDEFLUOR™-positive, but are not affected by MBE1.5. FIG. 4B is flow cytometry spectra, and shows that CD11c-positive bone marrow cells are ALDEFLUOR™-positive, but are not affected by MBE1.5. Similar results (not shown) were obtained in other populations tested, including CD45-positive and CD3e-positive (CD45+CD3e+) and CD11c-positive and CD317-positive (CD11+CD317+). Thus, all populations tested were ALDEFLUOR™-positive, but were not affected by MBE1.5, revealing little potential for toxicity.

Mouse Models and Xenografts

All mice were originally ordered from the Jackson Laboratory (Bar Harbor, ME) and breeding was conducted in a specific pathogen-free (SPF) barrier facility. Toxicity experiments were performed on 8-12-week old male and female C57B16 mice. MBE1 was dissolved at 50 mg/mL in DMSO followed by a 1:2 dilution into Kolliphor EL, followed by a 1:5 dilution into PBS to yield a 5 mg/ml MBE1 solution, (10% DMSO, 10% Kolliphor EL, 80% PBS). This was administered via IP injection at ascending doses from 12.5 to 200 mg/kg body mass in a set of 3 mice at 24 h intervals. Body condition score, food uptake, fecal/urine production, behavior and body weight were measured as toxicity readouts. Five mice were then treated every 3 days with 25 mg/kg MBE1 for 18 days. Neither experiment showed any indication of either acute or chronic toxicity.

All xenograft experiments were conducted on 8-week old female mice (athymic Nu/Nu, or NOD/SCID Gamma). Xenograft experiments were conducted using 125,000 SUM159-M1a cells in 100 µL PBS for tail vein or intracardiac injection. Mice were randomized following injection. Bioluminescent imaging (BLI) was conducted using the IVIS 200 system and retroorbital luciferin injection. For drug treatment, MBE1 (prepared as above) was given to mice via IP injection in conjunction with paclitaxel (5 mg/mL in 10% ethanol, 10% Kolliphor EL, 80% PBS) at the time intervals and dosages indicated in FIG. 5A (tail vein injection) and FIG. 6A (intracardiac injection).

Figure 5A:
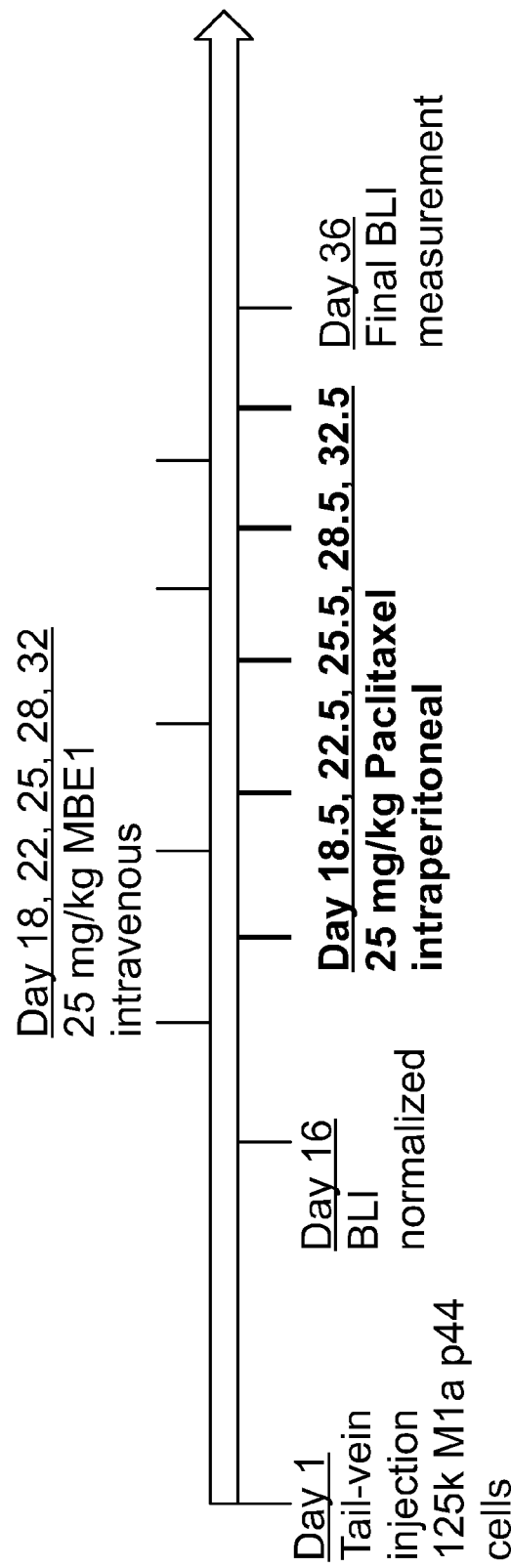
FIG. 5A is a diagram of the dosing strategy used to administer MBE1 and paclitaxel to mice injected with M1a-Aldh1a3 cells via intravenous tail-vein injection, and shows the design of an in vivo experiment designed to test the efficacy of MBE1 in treating metastatic cancer.
Figure 5B:
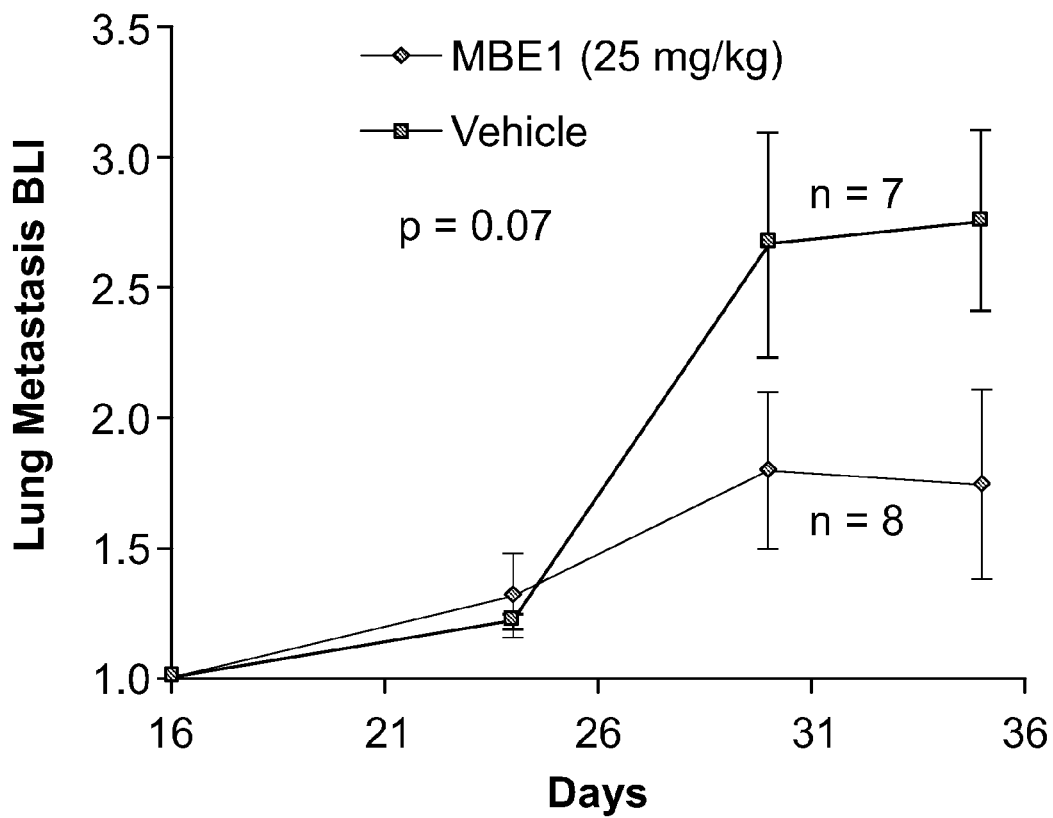
FIG. 5B is a line graph of lung metastasis, as measured using bioluminescence imaging (BLI), versus time (days), and compares lung metastasis in the presence and absence of MBE1 in the mice from the experiment outlined in FIG. 5A. Student's t-test, two-tailed, assuming unequal variance.
Figure 6A:
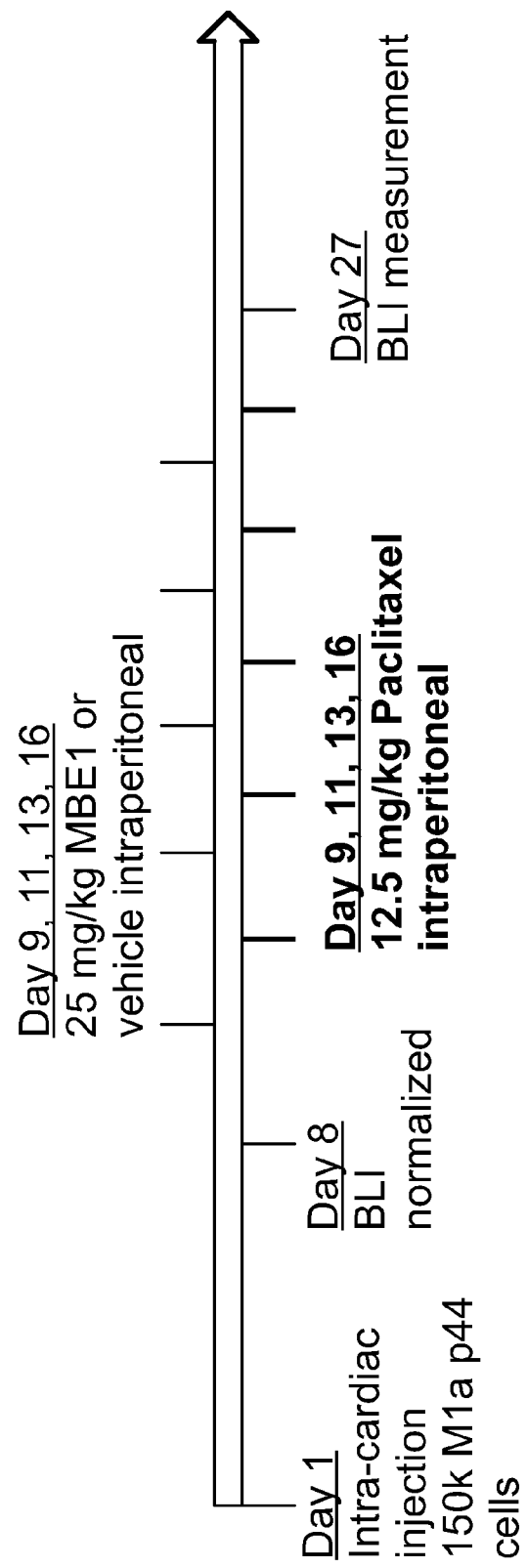
FIG. 6A is a diagram of the dosing strategy used to administer MBE1 and paclitaxel to mice injected with M1a-Aldh1a3 cells via intracardiac injection, and shows the design of an in vivo experiment designed to test the efficacy of MBE1 in treating metastatic cancer.
Figure 6B:
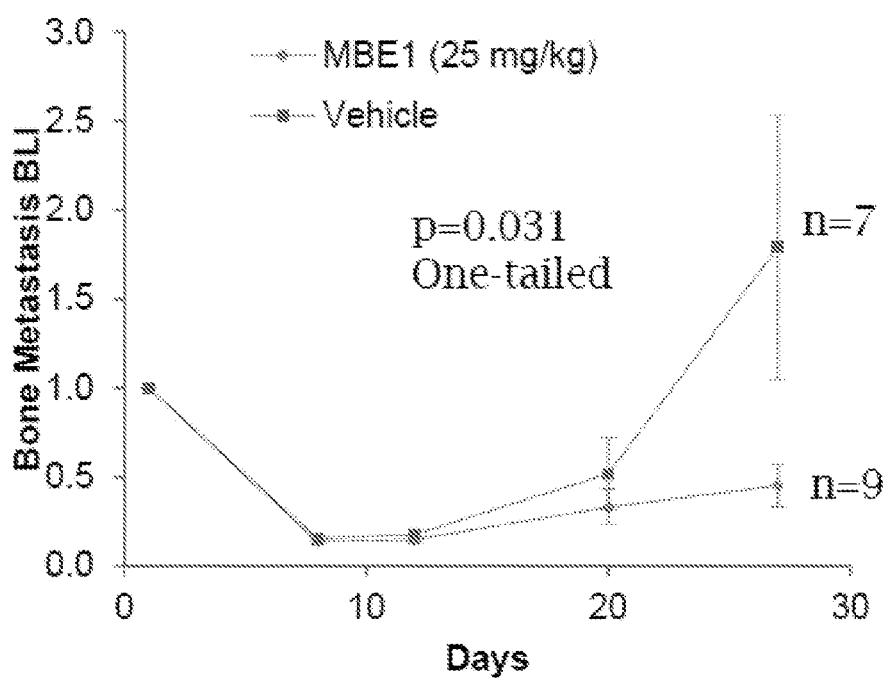
FIG. 6B is a line graph of bone metastasis, as measured using BLI, versus time (days), and compares bone metastasis in the presence and absence of MBE1 in the mice from the experiment outlined in FIG. 6A. Student's t-test, one-tailed, assuming unequal variance.

FIG. 5B is a line graph of lung metastasis, as measured using bioluminescence imaging (BLI), versus time (days), and compares lung metastasis in the presence and absence of MBE1 in the mice from the experiment outlined in FIG. 5A. FIG. 6B is a line graph of bone metastasis, as measured using BLI, versus time (days), and compares bone metastasis in the presence and absence of MBE1 in the mice from the experiment outlined in FIG. 6A. FIGS. 5B and 6B demonstrate that MBE1 is an effective therapeutic to treat established metastatic disease, and establishes that MBE1 and the compounds disclosed herein can be used to effectively inhibit ALDH1a3 and its downstream effects in vivo.

In another xenograft experiment, mice were injected with SUM159-M1-p44 cells via tail-vein injection, as described above, and randomized following injection. Metastatic burden was imaged on day 16 via intravital imaging. Mice were then treated with paclitaxel (25 mg/kg) and either vehicle or MBE1.5 (50 mg/kg) on days 17, 19 and 21. Lung metastatic burden was then imaged on day 22. Signals were normalized to day 16.

FIG. 14 is a line graph of lung metastasis, as measured by bioluminescent imaging (BLI), versus time (days), and shows that three doses of 50 mg/kg MBE1.5 in combination with 25 mg/kg paclitaxel, administered on days 17, 19 and 21 caused regression of established metastatic disease in a mouse xenograft model.

In yet another xenograft experiment, mice were injected with MDA-MB-468 cells via mammary fat pad, and were randomized following injection. Mice were treated with MBE1.5 (25 mg/kg daily, n=6) or vehicle (n=12), and paclitaxel (12.5 mg/kg every other day) for 12 days. Primary tumor measurements were taken by caliper between each treatment group.

FIG. 15A is a line graph of body mass (g) versus time (days), and shows that there was no gross toxicity associated with MBE1.5 treatment in this experiment. FIG. 15B is a line graph of tumor volume (mm$^3$) versus time (days), and shows that 12-day treatment with MBE1.5 caused regression of primary breast tumors. The tumors of two mice in the MBE1.5 treatment group were completely eliminated by the treatment.

In another xenograft experiment, mice were injected with Sum-159-M1a-Aldh1a3 cells via tail-vein injection, and were randomized following injection. Mice were treated with MBE1.5 (25 mg/kg daily) or vehicle, and paclitaxel (12.5 mg/kg every other day) for twelve days. Lung metastasis progression was tracked by intravital bioluminescence.

FIG. 16A is a line graph of lung metastasis bioluminescence versus time (days), and shows the progression of lung metastasis before and after treatment with MBE1.5 or vehicle. FIG. 16B is a Kaplan-Meier plot of mouse survival over time as a function of treatment group, and shows that 12-day treatment with MBE1.5 extended survival in mice with late-stage established breast cancer lung metastasis.

Pharmacokinetic Evaluation

Pharmacokinetic experiments were performed on 16-week old C57BL6 male mice. Mice were administered MBE1.5 (15% DMSO, 5% Kolliphor EL, 80% PBS) via IP injection. Blood was collected by terminal cardiac puncture at 15 minutes, 30 minutes, 1 hour, 3 hours, and 24 hours post-injection. Serum was obtained by blood separation via centrifugation at 16200 RCF for 1 min. Tissues were then collected following exsanguination. Serum and tissues were rapidly frozen in liquid nitrogen and submitted for pharmacokinetic evaluation.

Plasma Concentration Quantitation of MBE1.5 by LC/MS/MS for Mice PK Studies

Plasma MBE1.5 concentration was measured with LC/MS/MS assay in mice PK studies.

Chemicals: MBE1.5 and MBE2.0 were supplied as stocks (1 mg/mL) in MeOH with 1% DMSO. MBE2.0 was used as internal standard. HPLC grade acetonitrile and water were purchased from J.T. Baker (Center Valley, PA). The mouse plasma was purchased from Innovative Research (Novi, MI) for the preparation of plasma calibration standards.

LC/MS/MS Assay:

Preparation of standard solution: MBE1.5 stock was diluted in control mice plasma to obtain calibration range from 8.2 ng/mL to 18 µg/mL. 1 µg/mL MBE2.0 in methanol was used as a working internal standard (IS).

Sample preparation: The plasma standard and mouse plasma samples (20λ) were spiked with 54 µL IS and deproteinized with 120λ acetonitrile and methanol (v/v 5:1). After centrifugation at 13000 rpm for 15 minutes, 25λ of the supernatant was analyzed by LC-MS.

Liquid Chromatographic/Mass spectrometry: Quantitation of MBE1.5 was performed using TSQ Quantum triple quadruple mass spectrometer equipped with an API electrospray ionization (ESI) source, a Surveyor MS pump, a Surveyor Autosampler, with Xcalibur data acquisition software (ThermoElectron, San Jose, CA, USA).

LC conditions were as follows: mobile phase A: aqueous solution (0.1% formic acid); mobile phase B: acetonitrile (0.1% formic acid); flow rate 500 µL/min; gradient elution, 0 to 1 minute, 60% A; 1 to 2.5 minutes, 60% to 20% A; 2.5 to 7.0 minutes, 0% A, 7.0 to 9.0 minutes 0% A, 9.0 to 11.0 minutes, 0% to 60% A; and column: Luna® C18, 150×4.6 mm, 5 µm (Phenomenex, Torrance, CA). The retention times for MBE1.5 and IS were 6.3 minutes and 6.6 minutes, respectively.

MS/MS conditions were as follows: in single reaction monitoring mode, m/z 313.2/178.2 (MBE1.5), m/z 281.2/119.1 (MBE2.0, IS); ion spray voltage, 4500 v; capillary temperature 350° C.; sheath gas pressure 20 arbitrary units; Aux gas pressure 50 arbitrary units; collision pressure 1.5 arbitrary units. The collision energy and tube lens were optimized for each compound.

Calculation: Plasma calibration standards were used for the quantitation of MBE in plasma samples. The log linear regression was used for calibration curve to determine the concentration in plasma samples.

Results

LC/MS/MS assay: Plasma calibration curves for MBE1.5 were plotted using concentrations ranging from 8.2 ng/mL to 18 µg/mL. The limit of quantification was 8.2 ng/mL (LOD). The LC/MS/MS assay was in good linearity in the calibration range ($R^2>0.99$). Table 2 summarizes intra-assay accuracy and precision. No matrix effect was observed in this assay.

TABLE 2

MBE1.5 LC/MS/MS assay intra-assay accuracy and precision

| QC conc (µg/ml) | Measured (ng/mL, mean ± SD) | RSD (%) | Bias (%) |
|---|---|---|---|
| 0.0082 | 0.0084 ± 0.006 | 7.1 | 2.1 |
| 0.0246 | 0.0241 ± 0.002 | 7.3 | −2.0 |

TABLE 2-continued

MBE1.5 LC/MS/MS assay intra-assay accuracy and precision

| QC conc (μg/ml) | Measured (ng/mL, mean ± SD) | RSD (%) | Bias (%) |
|---|---|---|---|
| 0.222 | 0.214 ± 0.009 | 4.2 | −3.6 |
| 18.0 | 17.84 ± 0.793 | 4.4 | −0.8 |

Plasma PK of MBE1.5 in mice: The plasma concentration of MBE1.5 in mice PK studies is listed in Table 3. Preliminary PK data was analyzed using noncompartment model by Winnolin 2.0. The PK parameters are summarized in Table 4.

TABLE 3

Concentration of MBE1.5 in mouse plasma (μg/ml).

| Time (hr) | #1 | #2 | #3 | Mean | SD |
|---|---|---|---|---|---|
| 0 | <LOD | <LOD | <LOD | — | |
| 0.25 | 5.783 | 5.760 | 6.927 | 6.157 | 0.667 |
| 0.5 | 6.932 | 3.411 | 4.650 | 4.998 | 1.786 |
| 1 | 2.842 | 6.295 | 2.815 | 3.984 | 2.001 |
| 3 | 1.704 | 3.447 | 0.849 | 2.000 | 1.324 |
| 24 | <LOD | <LOD | <LOD | <LOD | |
| | 0.002* | 0.006* | 0.005* | 0.004* | 0.002 |

*Integrated peak area was less than LOD (limit of detection), forced to calculate.

TABLE 4

Pharmacokinetic parameters of MBE1.5 in mice (dose 25 mg/kg, i.p.)

| Calculation method | $AUC_{inf}$ (μg/mL*h) | $t_{1/2}$ (hr) | Clearance (mL/hr) |
|---|---|---|---|
| Time point to 3 hr | 15.70 | 1.90 | 39.87 |
| Time point to 24 hr | 16.90 | 2.32 | 36.96 |

Genetic Knockout of ALDH1a3

CRISPR-Cas9 vectors containing both the Cas9 gene and gRNA sequences containing homologous sequences to genomic Aldh1a3 were transduced into MDA-MB-468 cells by lentiviral infection followed by puromycin selection for viral integration, and the resulting cells were analyzed by ALDEFLUOR™ assay. Two ALDH1a3-targeting gRNA vectors were used to create two derivative cell lines, and one gRNA with a scrambled sequence was used to generate a control derivative cell line.

Figure 7A:
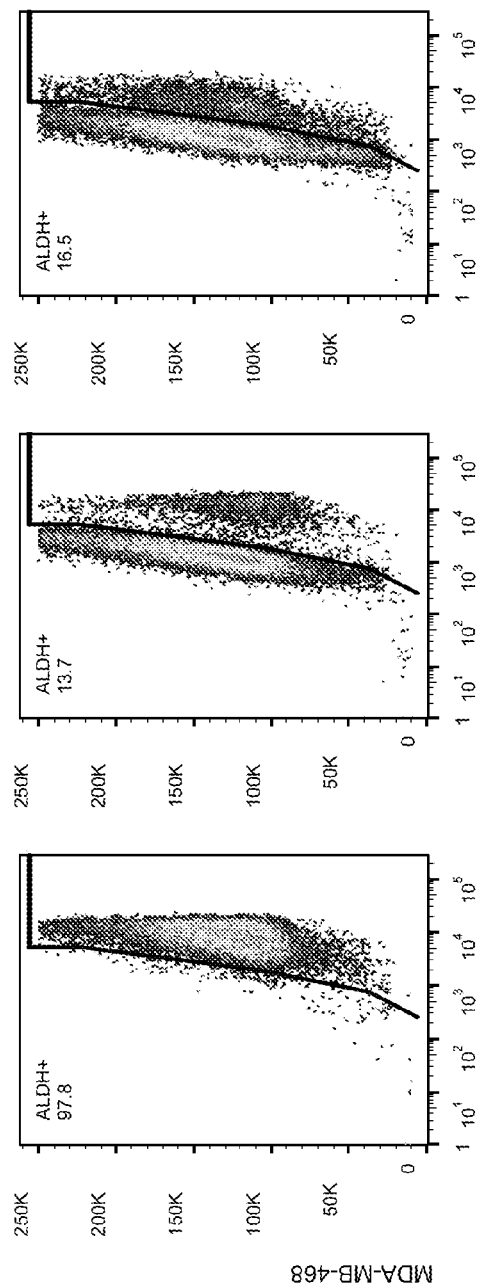
FIG. 7A is flow cytometry spectra, and shows that genetic knockout of ALDH1a3 (middle and rightmost spectra) in MDA-MB-468 breast cancer cells substantially decreases ALDEFLUOR™ activity compared to control MDA-MB-468 cells (leftmost spectra).
Figure 7B:
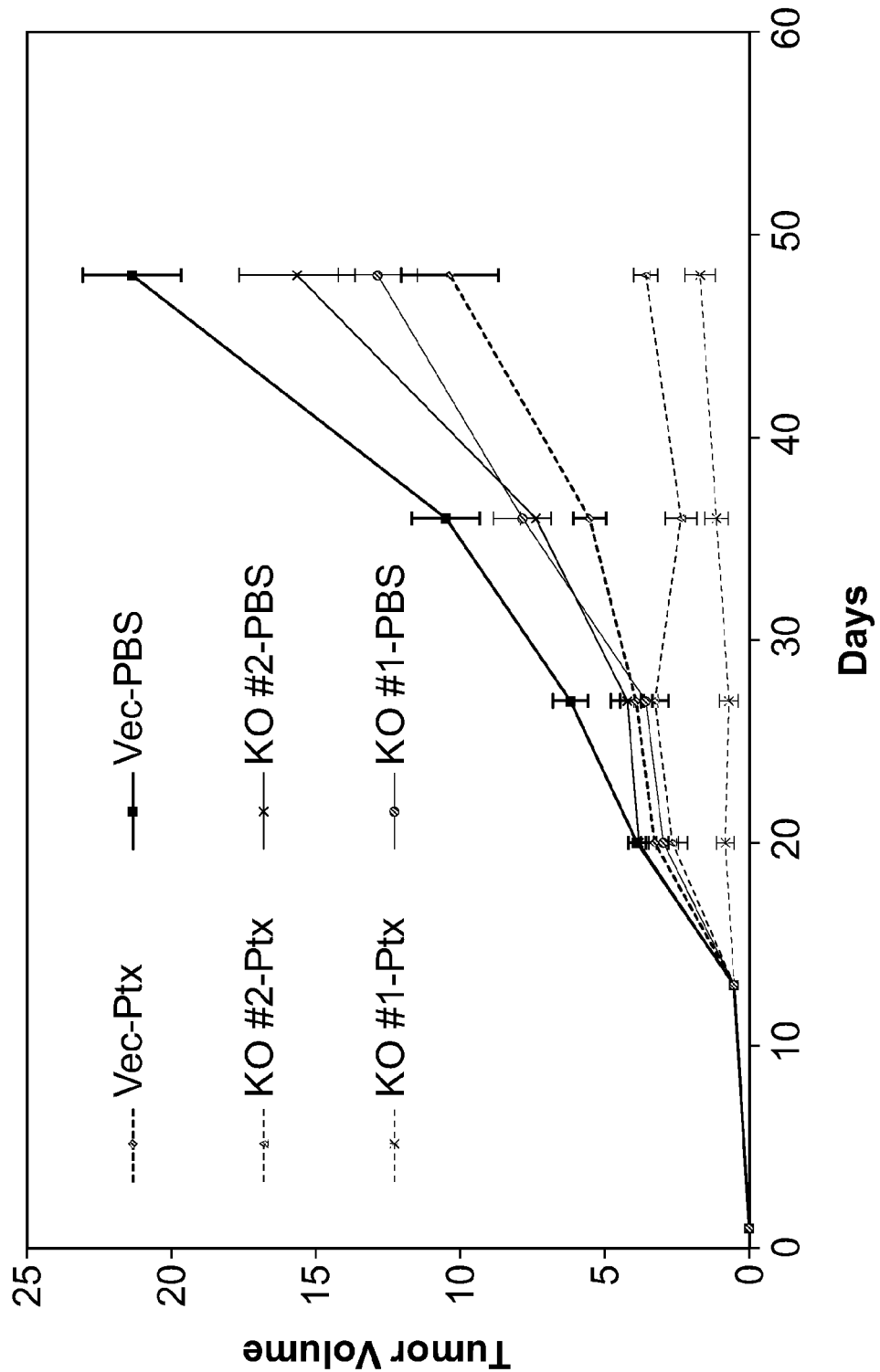
FIG. 7B is a line graph of tumor volume ($mm^3$) versus time (days), and shows that genetic knockout of ALDH1a3 in MDA-MB-468 breast cancer cells slows primary tumor growth and sensitizes tumors to paclitaxel.
Figure 7C:
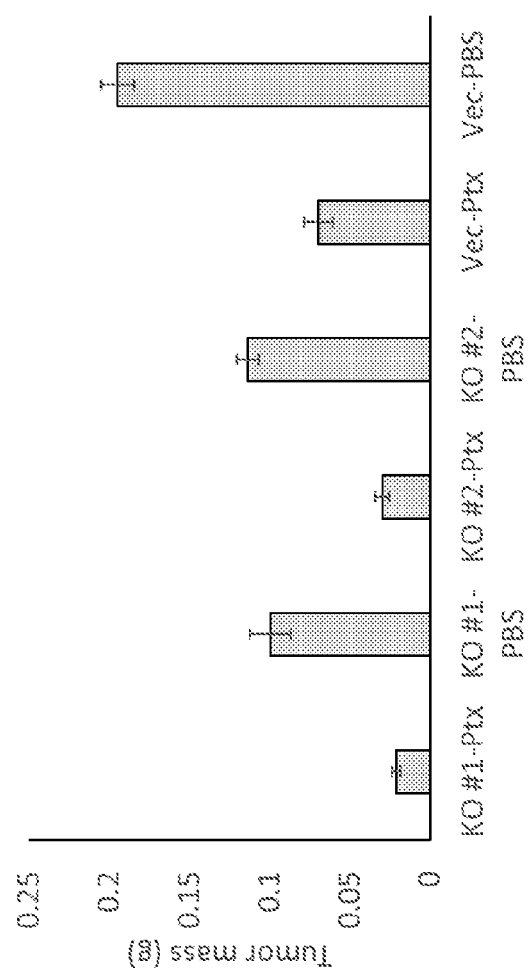
FIG. 7C is a bar graph of tumor mass (g) versus genetic knockout, and shows that genetic knockout of ALDH1a3 in MDA-MB-468 breast cancer cells slows primary tumor growth and sensitizes tumors to paclitaxel.

FIG. 7A is flow cytometry spectra, and shows that genetic knockout of ALDH1a3 (middle and rightmost spectra) in MDA-MB-468 breast cancer cells substantially decreases ALDEFLUOR™ activity compared to control MDA-MB-468 cells (leftmost spectra). FIG. 7B is a line graph of tumor volume (mm³) versus time (days), and shows that genetic knockout of ALDH1a3 in MDA-MB-468 breast cancer cells slows primary tumor growth and sensitizes tumors to paclitaxel. FIG. 7C is a bar graph of tumor mass (g) versus genetic knockout, and shows that genetic knockout of ALDH1a3 in MDA-MB-468 breast cancer cells slows primary tumor growth and sensitizes tumors to paclitaxel.

CRISPR-Cas9 vectors containing both the Cas9 gene and gRNA sequences containing homologous sequences to genomic Aldh1a3 were transfected into Sum159-Mia cells followed by selection for positively transfected cells by flow cytometry. Positively transfected cells were then virally transduced with lentiviral vectors containing either the vector backbone or full-length human Aldh1a3. Positive transductants were selected by puromycin, and the resulting cells were analyzed by ALDEFLUOR™ assay. In a xenograft experiment, the knockout-vector or knockout-Aldh1a3 or wild-type vector or wild-type-Aldh1a3 cells were injected by intracardiac injection into mice, and bone metastasis growth was tracked by intravital bioluminescent imaging. Bone metastasis-free survival was tracked by bioluminescence, and plotted using the Kaplan-Meier model.

Figure 9A:
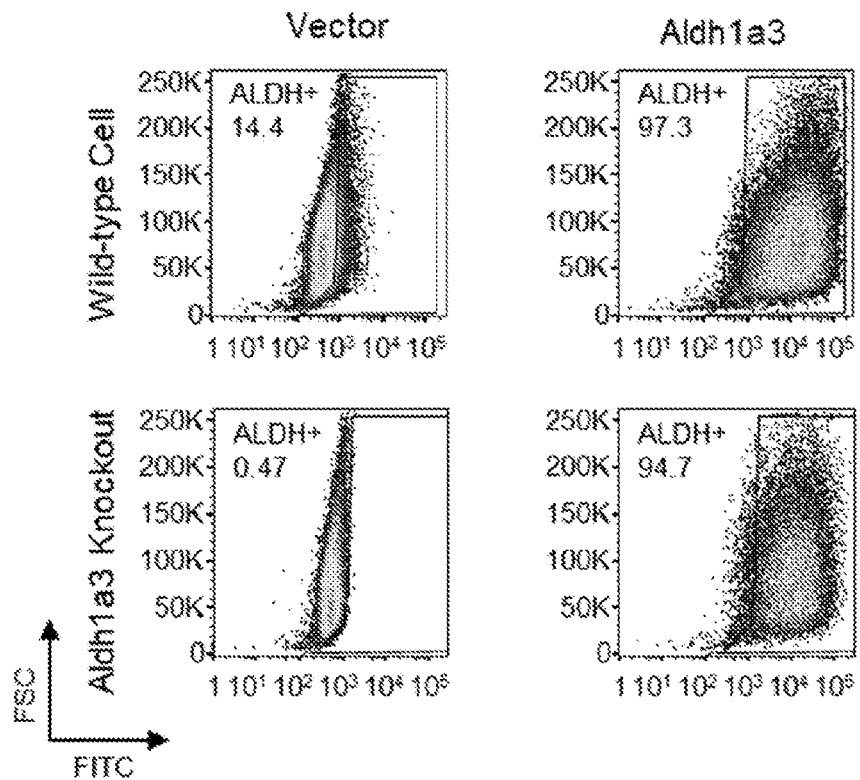
FIG. 9A is flow cytometry spectra, and shows that genetic knockout of ALDH1a3 in Sum159-Mia breast cancer cells nearly abolishes ALDEFLUOR™ activity in the cells, and that ALDEFLUOR™ activity can be rescued by transducing the cells with a rescue vector.
Figure 9B:
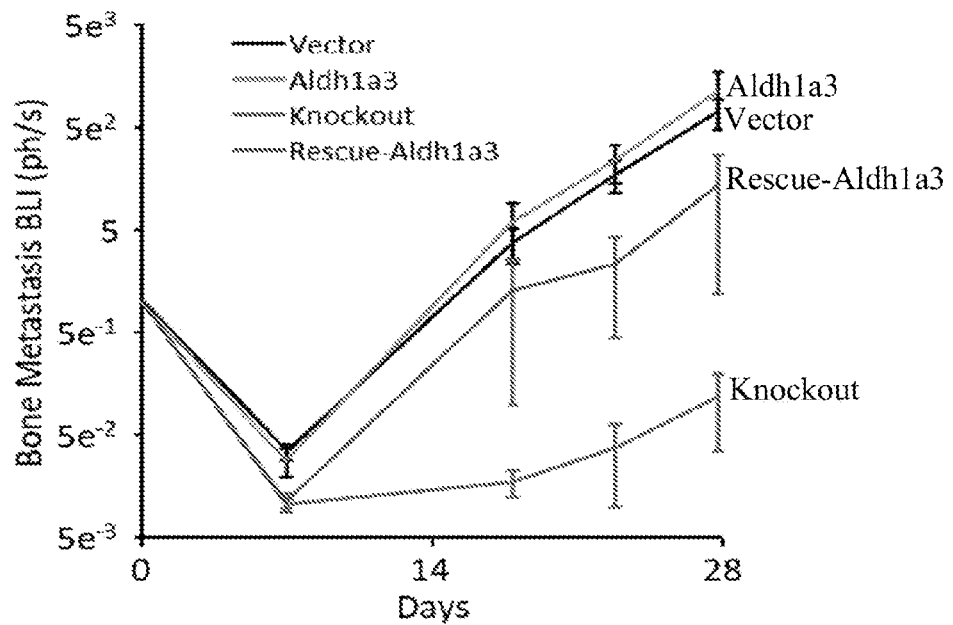
FIG. 9B is a line graph of bone metastasis, as measured by bioluminescence (ph/s), versus time (days), and shows that knockout of ALDH1a3 in Sum159-M1a breast cancer cells slows bone metastasis growth.
Figure 9C:
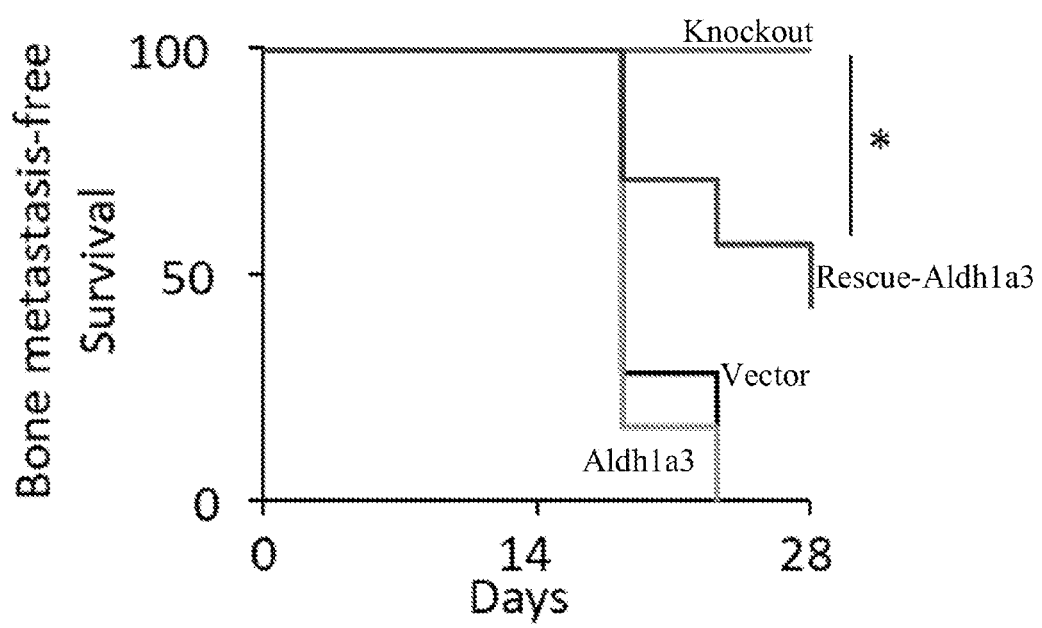
FIG. 9C is a Kaplan-Meier plot of bone metastasis-free survival over time, and shows that knockout of ALDH1a3 in Sum159-Mia breast cancer cells significantly increases survival time.
Figure 10A:
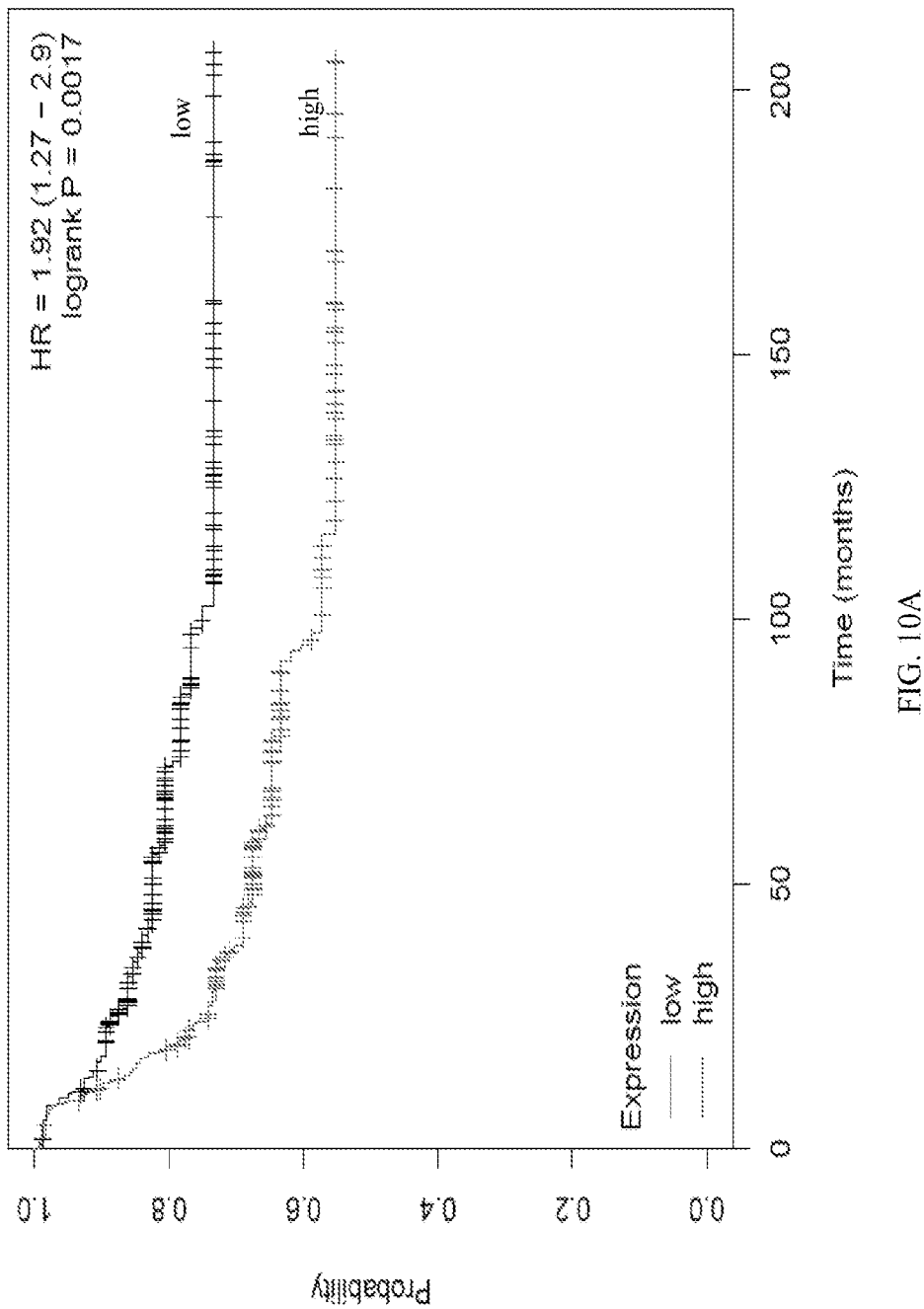
FIG. 10A is a patient survival curve stratified by high (red) and low (black) Aldh1a3 expression based on the data analysis tool hosted at kmplot.com, and shows the distant metastasis-free survival for renal clear cell cancer patients as a function of ALDH1a3 expression level.
Figure 10B:
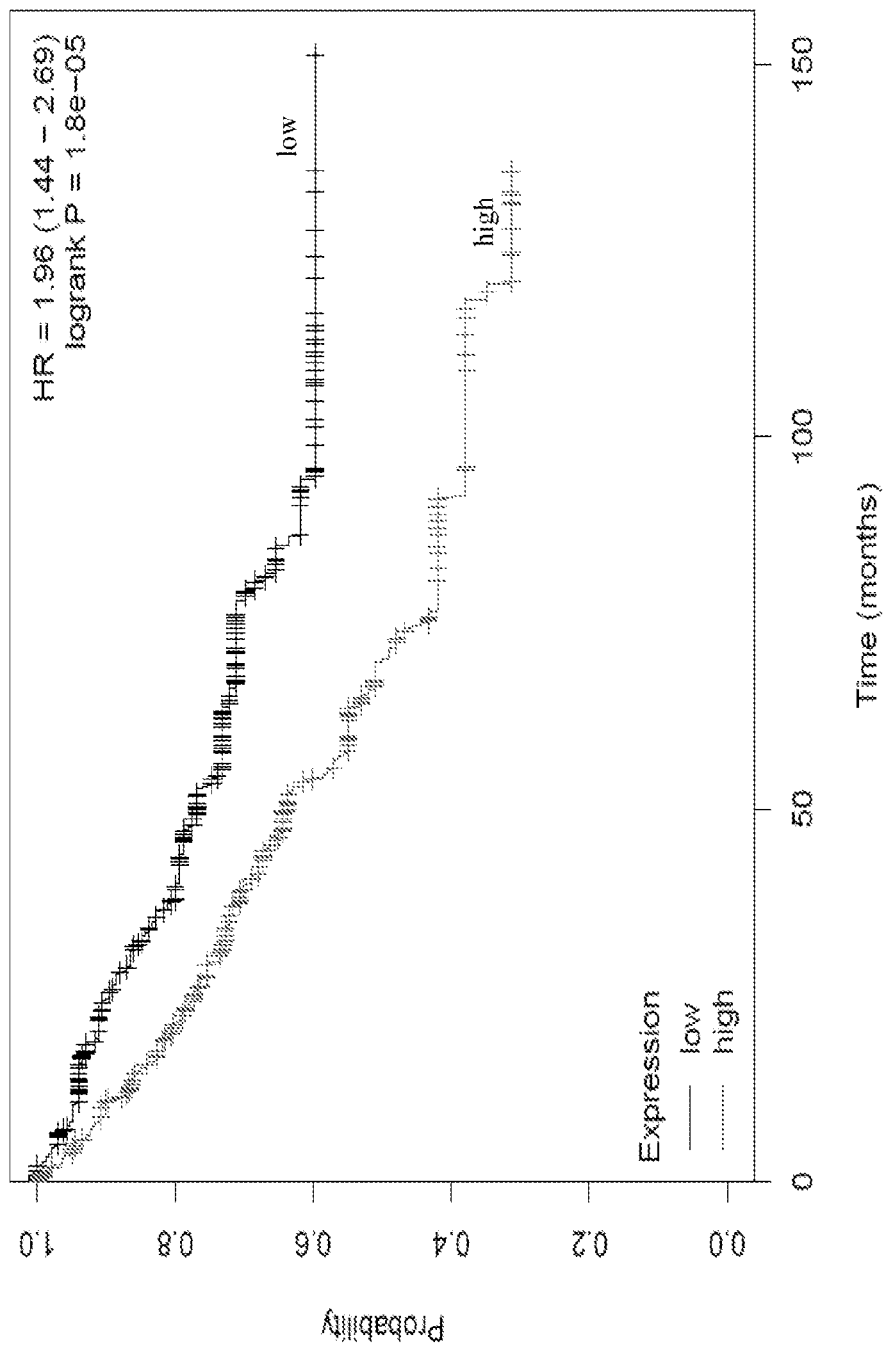
FIG. 10B is a patient survival curve stratified by high (red) and low (black) Aldh1a3 expression based on the data analysis tool hosted at kmplot.com, and shows the overall survival for triple negative breast cancer patients as a function of ALDH1a3 expression level.
Figure 10C:
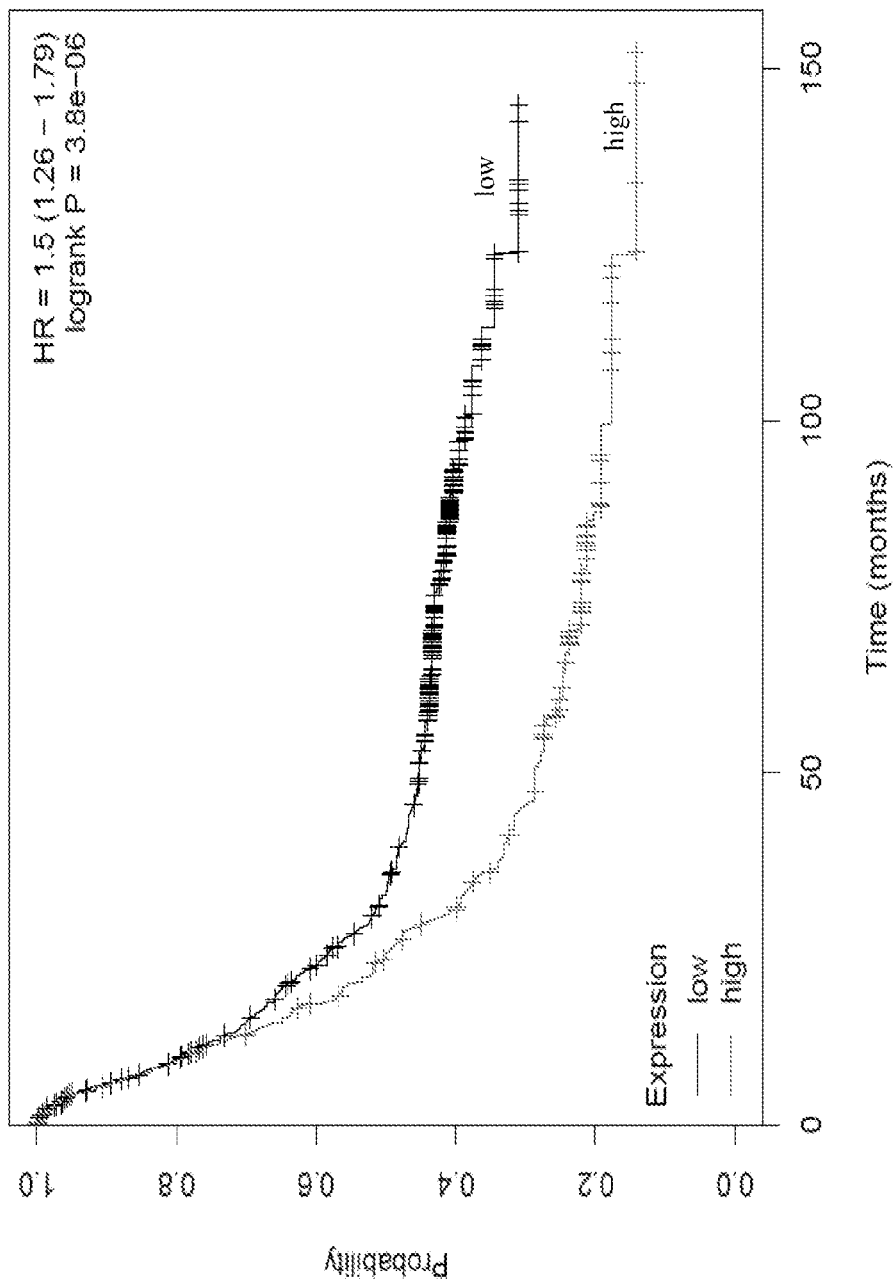
FIG. 10C is a patient survival curve stratified by high (red) and low (black) Aldh1a3 expression based on the data analysis tool hosted at kmplot.com, and shows the overall survival for gastric cancer patients as a function of ALDH1a3 expression level.
Figure 10D:
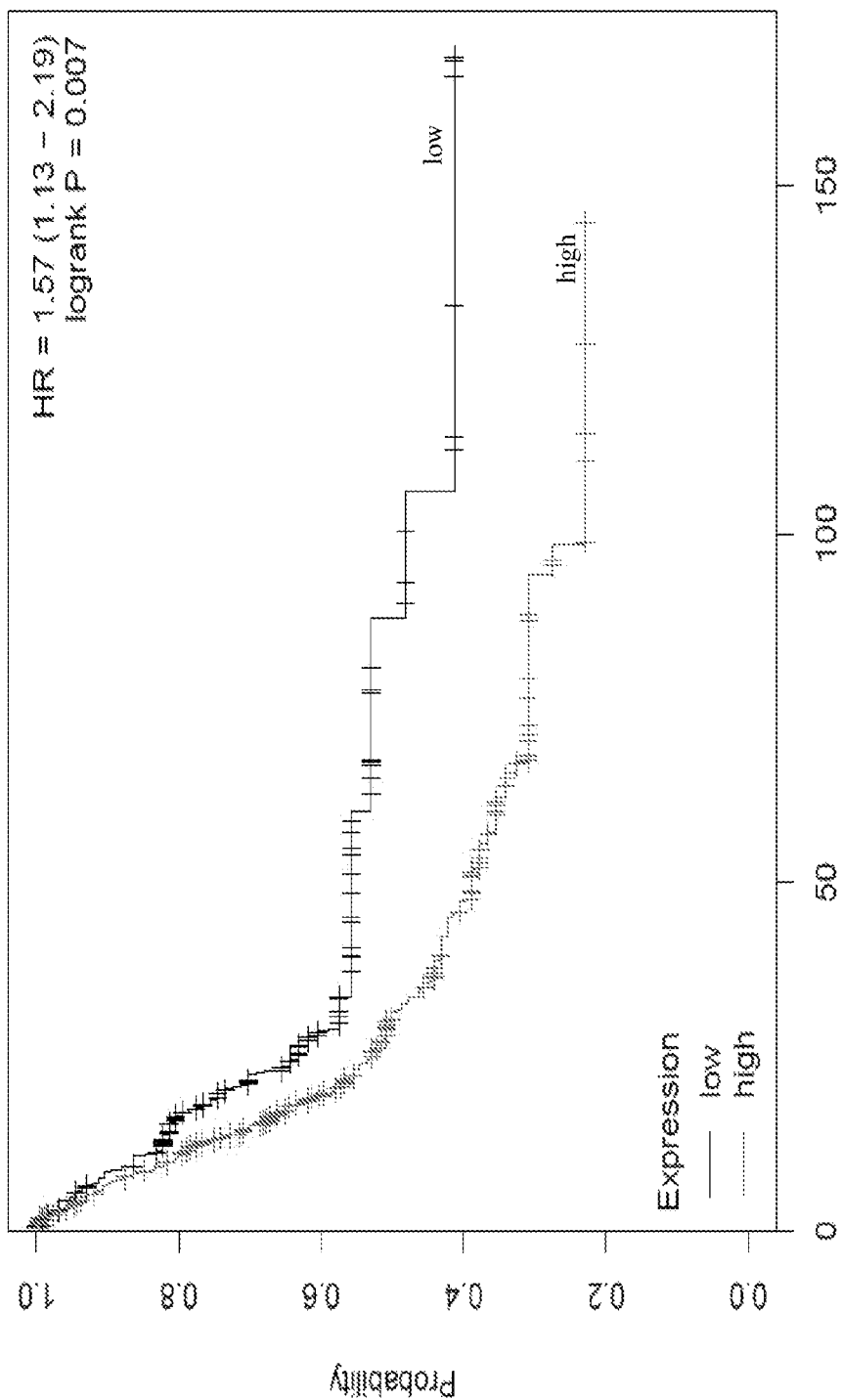
FIG. 10D is a patient survival curve stratified by high (red) and low (black) Aldh1a3 expression based on the data analysis tool hosted at kmplot.com, and shows the overall survival for bladder cancer patients as a function of ALDH1a3 expression level.
Figure 10E:
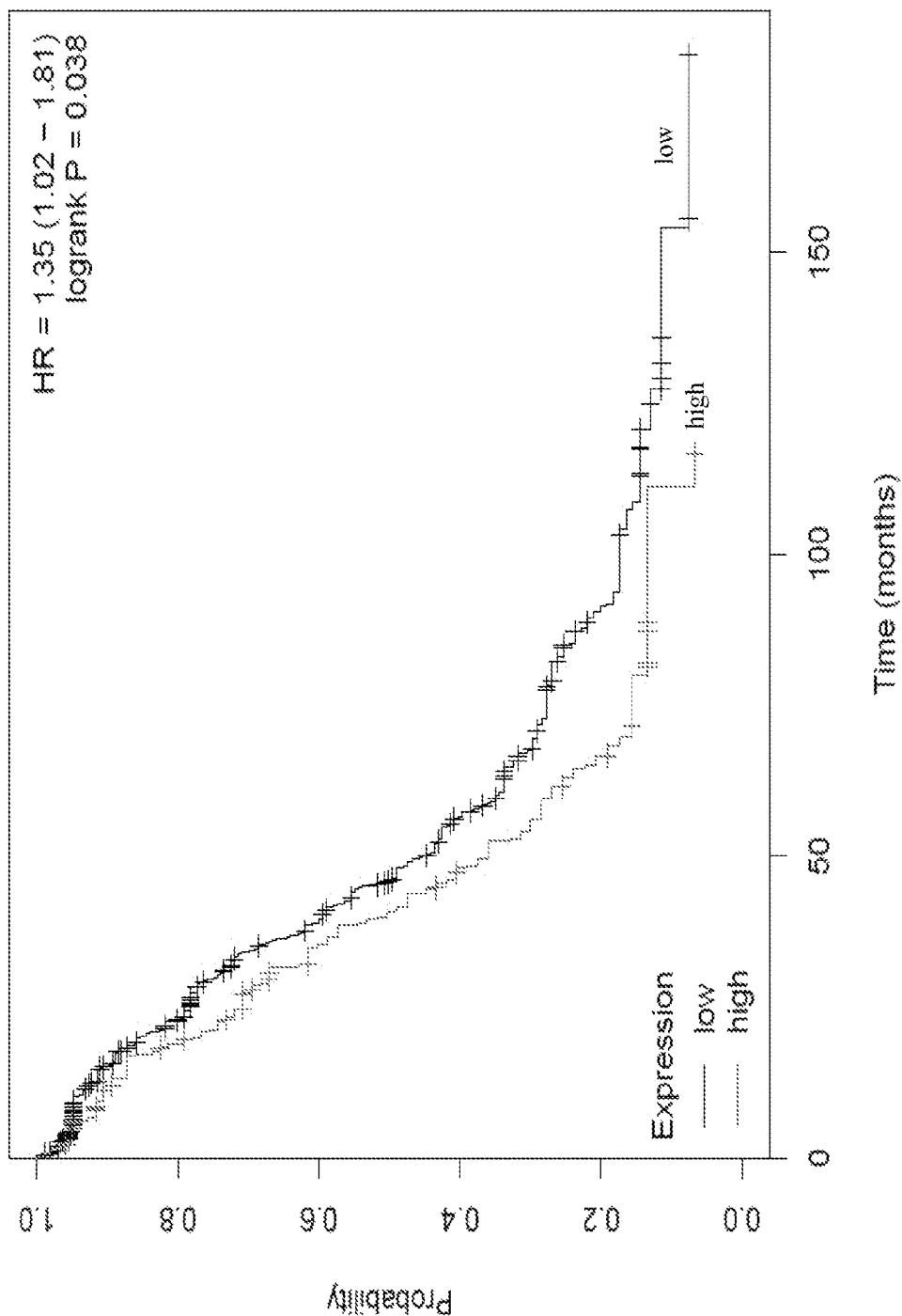
FIG. 10E is a patient survival curve stratified by high (red) and low (black) Aldh1a3 expression based on the data analysis tool hosted at kmplot.com, and shows the overall survival for ovarian cancer patients as a function of ALDH1a3 expression level.
Figure 10F:
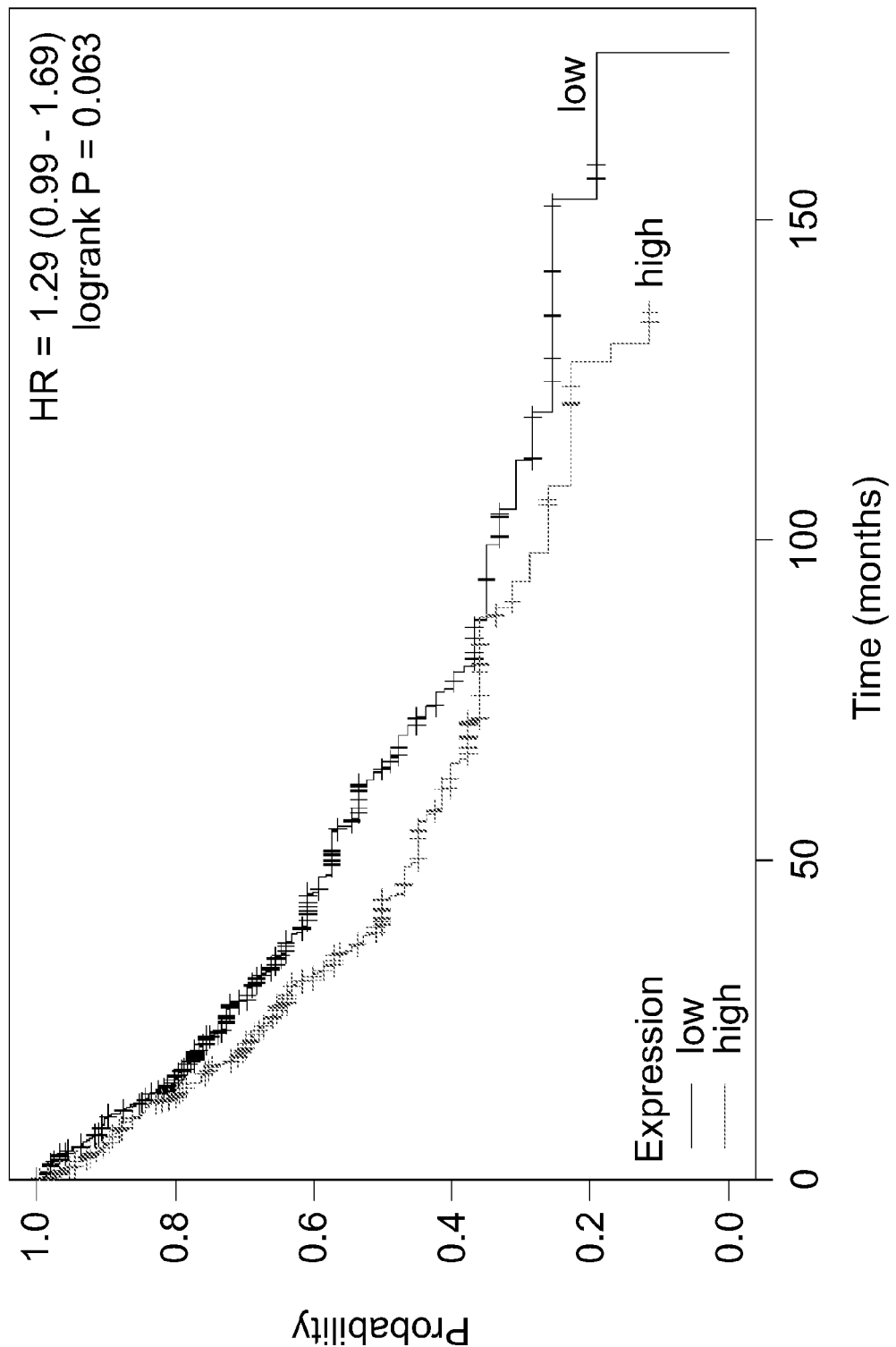
FIG. 10F is a patient survival curve stratified by high (red) and low (black) Aldh1a3 expression based on the data analysis tool hosted at kmplot.com, and shows the overall survival for lung squamous cancer patients as a function of ALDH1a3 expression level.
Figure 10G:
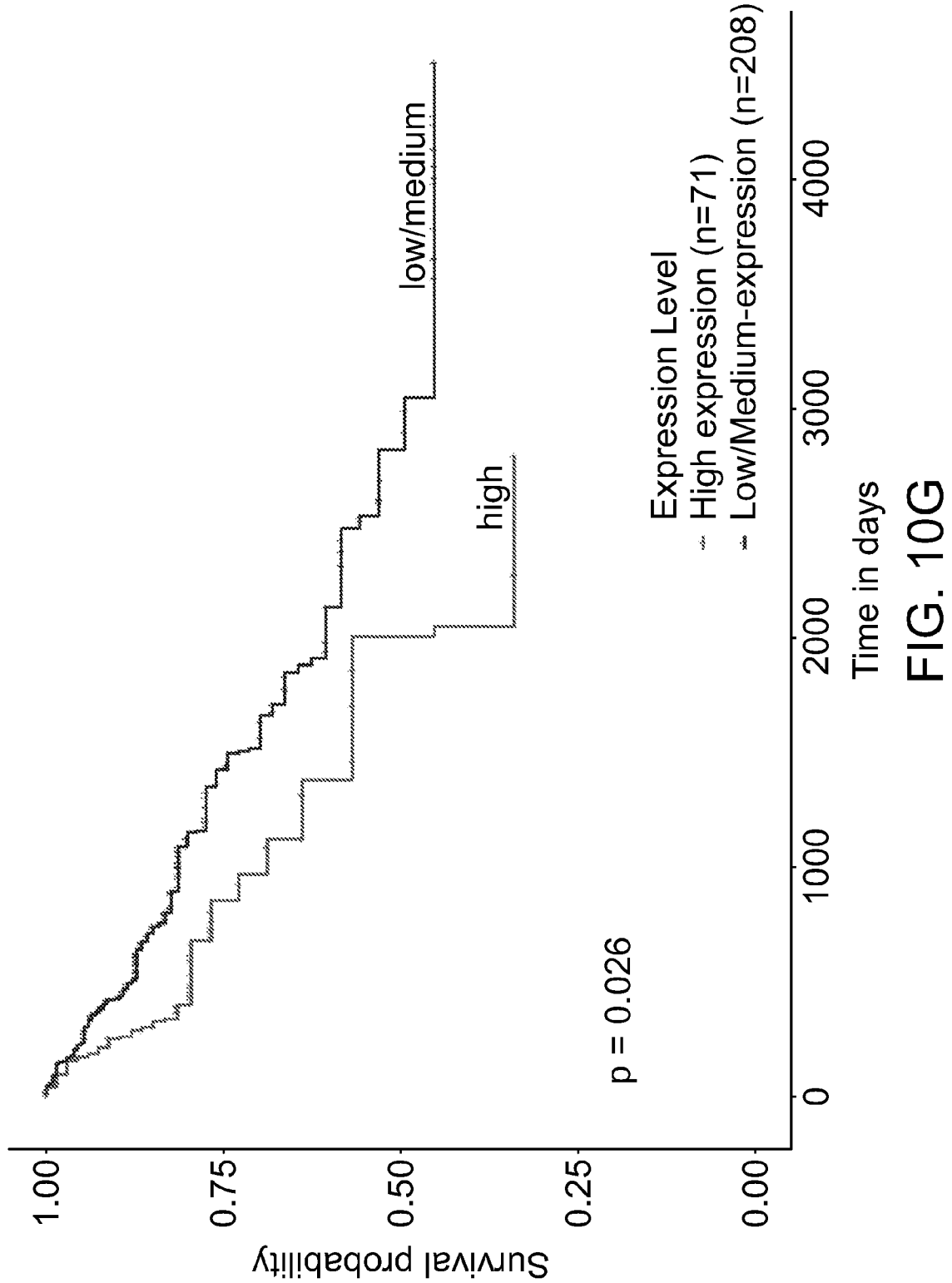
FIG. 10G is a patient survival curve stratified by high (red) and low (blue) Aldh1a3 expression based on survival time series data and patient-level RNA expression data from The Cancer Genome Atlas, and shows the overall survival for colorectal cancer patients as a function of ALDH1a3 expression level.
Figure 10H:
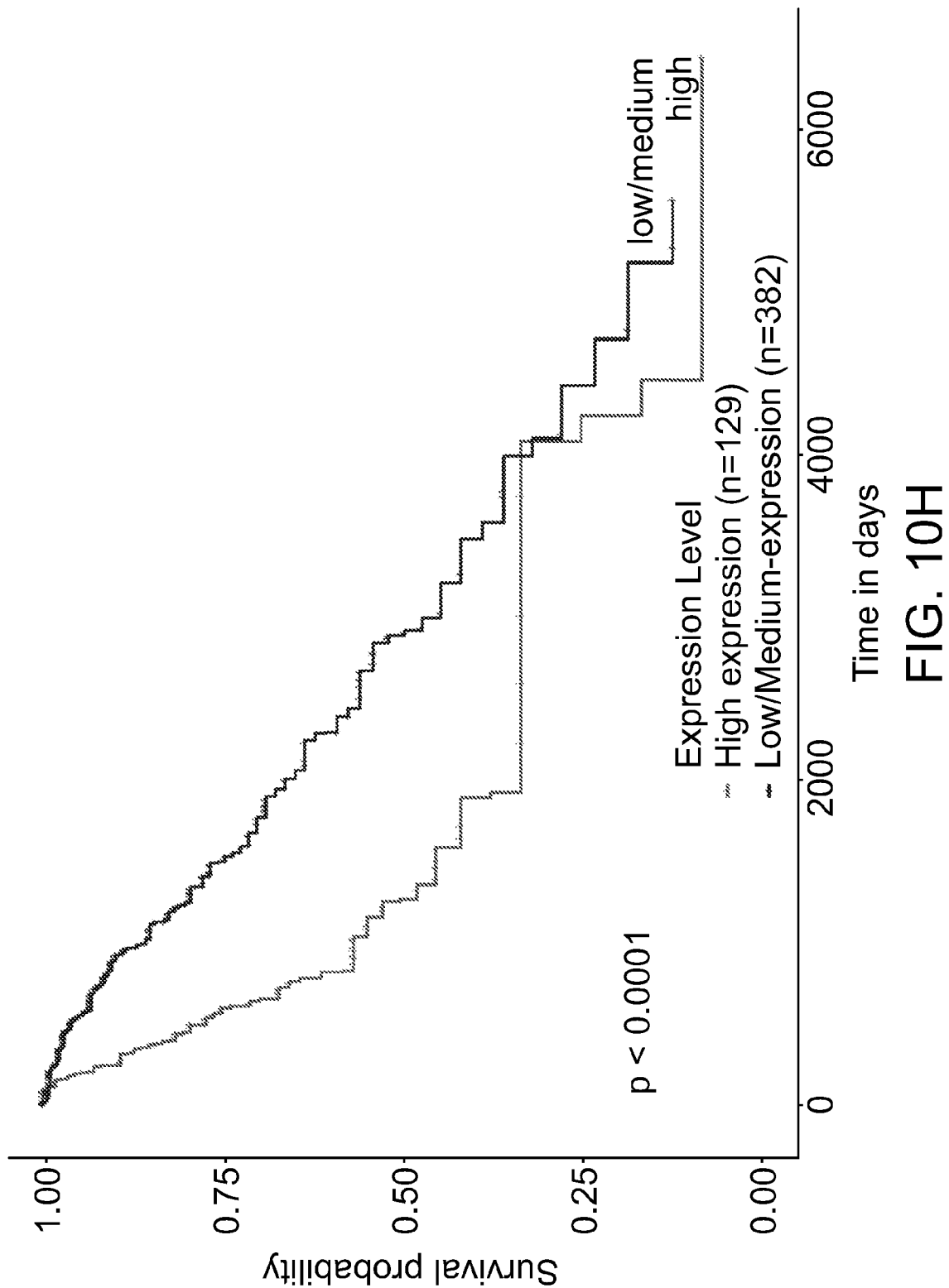
FIG. 10H is a patient survival curve stratified by high (red) and low (blue) Aldh1a3 expression based on survival time series data and patient-level RNA expression data from The Cancer Genome Atlas, and shows the overall survival for low-grade glioma patients as a function of ALDH1a3 expression level.

FIG. 9A is flow cytometry spectra, and shows that genetic knockout of ALDH1a3 in Sum159-Mia breast cancer cells nearly abolishes ALDEFLUOR™ activity in the cells, and that ALDEFLUOR™ activity can be rescued by transducing the cells with a rescue vector. FIG. 9B is a line graph of bone metastasis, as measured by bioluminescence (ph/s), versus time (days), and shows that knockout of ALDH1a3 in Sum159-Mia breast cancer cells slows bone metastasis growth. FIG. 9C is a Kaplan-Meier plot of bone metastasis-free survival over time, and shows that knockout of ALDH1a3 in Sum159-M1a breast cancer cells significantly increases survival time.

Genetic Expression of ALDH1a3

Lentiviral vectors encoding one of three human ALDH genes, ALDH1a1, ALDH1a3 or ALDH3a1, were introduced by viral transduction into luciferase-labeled Sum159-M1b cells followed by positive selection with puromycin, and the transduced cells were injected by tail-vein injection into mice. Growth of lung metastasis was tracked by intravital bioluminescence imaging once weekly. Lung nodes were counted ex vivo.

Figure 8A:
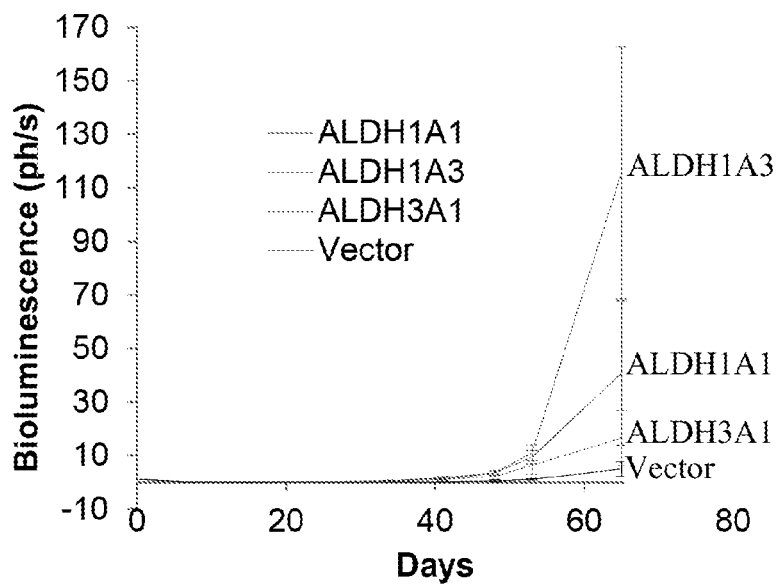
FIG. 8A is a line graph of bioluminescence (ph/s) versus time (days), and shows the development of lung metastasis in mice injected with SUM159-M1b cells transduced with vectors encoding three ALDH enzymes, ALDH1a1, ALDH1a3 and ALDH3a1.
Figure 8B:
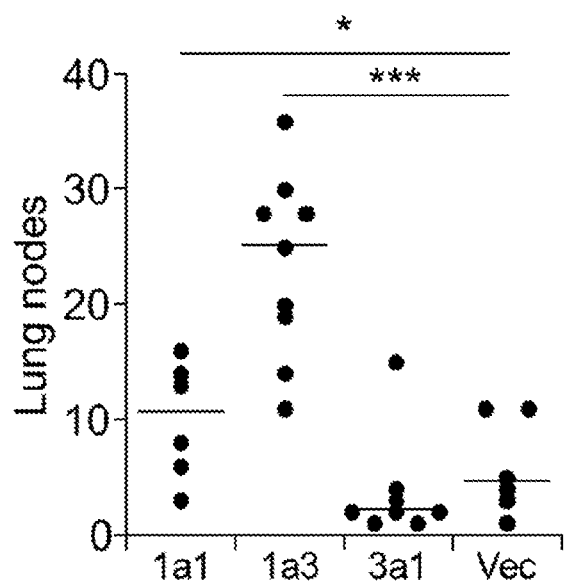
FIG. 8B is a plot of lung nodes counted ex vivo at the endpoint of the experiment described in FIG. 8A. Student's t-test, two-tailed, assuming unequal variance.

FIG. 8A is a line graph of bioluminescence (ph/s) versus time (days), and shows the development of lung metastasis in mice injected with SUM159-M1b cells transfected with vectors encoding three ALDH enzymes, ALDH1a1, ALDH1a3 and ALDH3a1. FIG. 8B is a plot of lung nodes counted ex vivo at the endpoint of the experiment described in FIG. 8A.

Survival Predictions

TCGA and Kaplan-Meier plotter (kmplot.com) data was used to generate expression data and survival curves for various cancers as a function of ALDH1a3 expression level. Cancer patients from each dataset were stratified by high or low Aldh1a3 expression according to either median expression value or the optimal stratification value. Kaplan-Meier analysis was then used to plot patient survival, whether measuring distant metastasis-free or overall survival, to assess the relationship between relative levels of Aldh1a3 between patients and corresponding survival metrics.

FIGS. 10A-10H are prognostic patient survival curves stratified by high (red) and low (black) Aldh1a3 expression based on the data analysis tool hosted at kmplot.com, and show the distant metastasis free survival for triple negative breast cancer patients (FIG. 10A) and overall survival for renal clear cell, gastric, bladder cancer, ovarian cancer, lung squamous cancer, colorectal cancer and low-grade glioma cancer patients (FIGS. 10B-10H, respectively) as a function of ALDH1a3 expression level.

In another set of predictions, mRNA expression of Aldh1a3 from the METABRIC clinical breast cancer dataset was segregated by tumor type and prior treatment with chemotherapy. Survival curves in the EMC-MSK dataset were generated by splitting patients according to subtype, and stratifying by median Aldh1a3 expression.

Figure 11A:
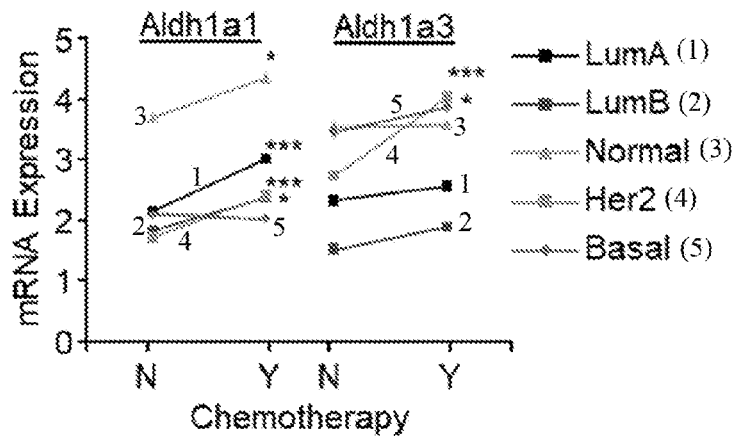
FIG. 11A is graph of mRNA expression of Aldh1a3 from the METABRIC clinical breast cancer dataset, and shows expression of Aldh1a3 by breast cancer subtype and history of chemotherapy.
Figure 11B:
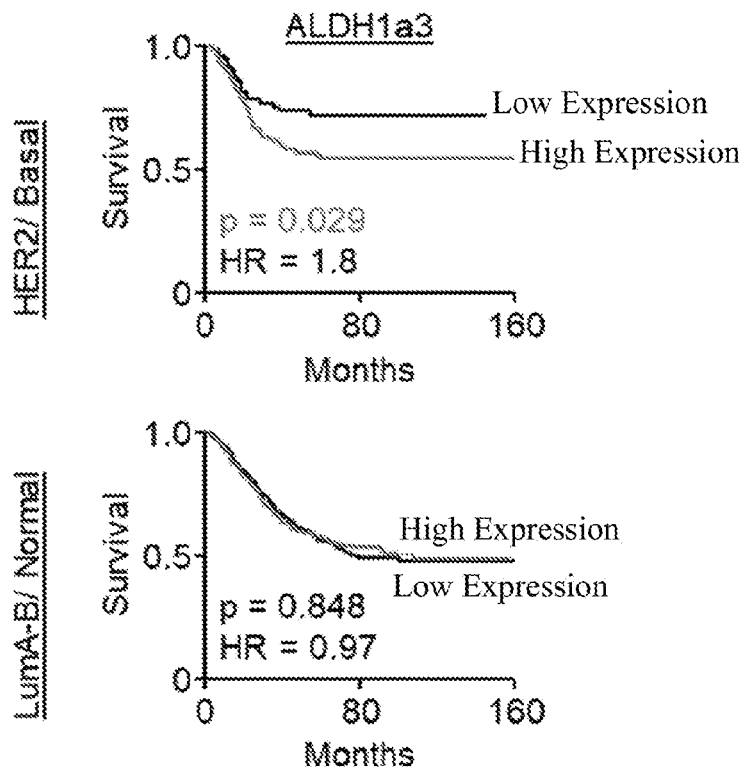
FIG. 11B is a set of survival curves based on the Erasmus Medical Center-Memorial Sloan-Kettering (EMC-MSK)

FIG. 11A is graph of mRNA expression of ALDH1a3 from the METABRIC clinical breast cancer dataset, and shows expression of ALDH1a3 by breast cancer subtype and history of chemotherapy. FIG. 11B is predicted survival curves based on the EMC-MSK dataset, and shows the predicted survival time of breast cancer patients by subtype and median ALDH1a3 expression level.

Table 5 reports the hazard ratio (p-value) of patients expressing high ALDH1a1 or ALDH1a3 in estrogen receptor (ER)-negative breast cancer derived from the Kaplan-Meier plotter database, and includes the Her2 and triple negative breast cancer (TNBC) populations that are at high risk for developing metastasis. ALDH1a3 is a poor prognosis predictor in ER-negative breast cancer patients, the population most likely to develop metastasis.

TABLE 5

Hazard ratio (p-value) of patients expressing high ALDH1a1 or ALDH1a3 in ER-negative breast cancer patient populations derived from the Kaplan-Meier plotter database

| Gene | All | Chemo-therapy | No Chemo-therapy |
| --- | --- | --- | --- |
| ALDH1a1 | 0.48 (0.00039) | 2.34 (0.065) | 0.48 (0.0071) |
| ALDH1a3 | 1.85 (0.004) | 3.3 (0.026) | 1.81 (0.032) |

REFERENCES

1 Vasiliou, V., Thompson, D. C., Smith, C., Fujita, M. & Chen, Y. Aldehyde dehydrogenases: from eye crystallins to metabolic disease and cancer stem cells. *Chem Biol Interact* 202, 2-10, doi:10.1016/j.cbi.2012.10.026 S0009-2797(12)00233-5 [pii] (2013).

2 Dupe, V. et al. A newborn lethal defect due to inactivation of retinaldehyde dehydrogenase type 3 is prevented by maternal retinoic acid treatment. *Proc Natl Acad Sci USA* 100, 14036-14041, doi:10.1073/pnas.2336223100 2336223100 [pii] (2003).

3 Anthony, T. E. & Heintz, N. The folate metabolic enzyme ALDH1L1 is restricted to the midline of the early CNS, suggesting a role in human neural tube defects. *J Comp Neurol* 500, 368-383, doi:10.1002/cne.21179 (2007).

4 Ducker, G. S. et al. Reversal of Cytosolic One-Carbon Flux Compensates for Loss of the Mitochondrial Folate Pathway. *Cell Metab* 24, 640-641, doi:S1550-4131(16) 30491-0 [pii]10.1016/j.cmet.2016.09.011 (2016).

Pappa, A. et al. Human aldehyde dehydrogenase 3A1 inhibits proliferation and promotes survival of human corneal epithelial cells. *J Biol Chem* 280, 27998-28006, doi: M503698200 [pii]10.1074/jbc.M503698200 (2005).

6 Black, W. et al. Molecular mechanisms of ALDH3A1-mediated cellular protection against 4-hydroxy-2-nonenal. *Free Radic Biol Med* 52, 1937-1944, doi:10.1016/j.freeradbiomed.2012.02.050 S0891-5849(12)00156-6 [pii] (2012).

7 Blanco-Gandia, M. C. & Rodriguez-Arias, M. Pharmacological treatments for opiate and alcohol addiction: a historical perspective of the last 50 years. *Eur J Pharmacol*, doi:S0014-2999(18)30451-5 [pii] 10.1016/j.ejphar.2018.08.007 (2018).

8 Rodriguez-Torres, M. & Allan, A. L. Aldehyde dehydrogenase as a marker and functional mediator of metastasis in solid tumors. *Clin Exp Metastasis* 33, 97-113, doi: 10.1007/s10585-015-9755-9 10.1007/s10585-015-9755-9 [pii] (2016).

9 Plaisancie, J. et al. Incomplete penetrance of biallelic ALDH1A3 mutations. *Eur J Med Genet* 59, 215-218, doi:10.1016/j.ejmg.2016.02.004 51769-7212(16)30015-5 [pii] (2016).

5 Yao, H. et al. CHD7 represses the retinoic acid synthesis enzyme ALDH1A3 during inner ear development. *JCI Insight* 3, doi:10.1172/jci.insight.97440 97440 [pii] (2018).

11 Minkina, A. et al. Retinoic acid signaling is dispensable for somatic development and function in the mammalian ovary. *Dev Biol* 424, 208-220, doi:S0012-1606(16) 30849-1 [pii]10.1016/j.ydbio.2017.02.015 (2017).

12 Wang, S. et al. ALDH1A3 correlates with luminal phenotype in prostate cancer. *Tumour Biol* 39, 1010428317703652, doi:10.1177/1010428317703652 (2017).

13 Kim-Muller, J. Y. et al. Aldehyde dehydrogenase 1a3 defines a subset of failing pancreatic beta cells in diabetic mice. *Nat Commun* 7, 12631, doi:10.1038/ncomms12631ncomms12631 [pii] (2016).

14 Shimamura, M., Karasawa, H., Sakakibara, S. & Shinagawa, A. Raldh3 expression in diabetic islets reciprocally regulates secretion of insulin and glucagon from pancreatic islets. *Biochem Biophys Res Commun* 401, 79-84, doi:10.1016/j.bbrc.2010.09.013 S0006-291X(10)01688-8 [pii] (2010).

15 Berenguer, M., Lancman, J. J., Cunningham, T. J., Dong, P. D. S. & Duester, G. Mouse but not zebrafish requires retinoic acid for control of neuromesodermal progenitors and body axis extension. *Dev Biol* 441, 127-131, doi: S0012-1606(18)30290-2 [pii] 10.1016/j.ydbio.2018.06.019 (2018).

16 Niederreither, K., Subbarayan, V., Dolle, P. & Chambon, P. Embryonic retinoic acid synthesis is essential for early mouse post-implantation development. *Nat Genet* 21, 444-448, doi:10.1038/7788 (1999).

17 Feng, R. et al. Retinoic acid homeostasis through aldh1a2 and cyp26a1 mediates meiotic entry in Nile tilapia (*Oreochromis niloticus*). *Sci Rep* 5, 10131, doi:10.1038/srep10131 srep10131 [pii] (2015).

18 Hall, J. A., Grainger, J. R., Spencer, S. P. & Belkaid, Y. The role of retinoic acid in tolerance and immunity. *Immunity* 35, 13-22, doi:10.1016/j.immuni.2011.07.002 S1074-7613(11)00270-6 [pii] (2011).

19 Mucida, D. et al. Reciprocal TH17 and regulatory T cell differentiation mediated by retinoic acid. *Science* 317, 256-260, doi:1145697 [pii]10.1126/science.1145697 (2007).

20 Lee, S. W. et al. Cutting edge: 4-1BB controls regulatory activity in dendritic cells through promoting optimal expression of retinal dehydrogenase. *J Immunol* 189, 2697-2701, doi:10.4049/jimmunol.1201248jimmunol.1201248 [pii] (2012).

21 Zhu, B. et al. IL-4 and retinoic acid synergistically induce regulatory dendritic cells expressing Aldh1a2. *J Immunol* 191, 3139-3151, doi:10.4049/jimmunol.1300329jimmunol.1300329 [pii] (2013).

22 Guilliams, M. et al. Skin-draining lymph nodes contain dermis-derived CD103(−) dendritic cells that constitutively produce retinoic acid and induce Foxp3(+) regulatory T cells. *Blood* 115, 1958-1968, doi:10.1182/blood-2009-09-245274blood-2009-09-245274 [pii] (2010).

23 Spiegl, N., Didichenko, S., McCaffery, P., Langen, H. & Dahinden, C. A. Human basophils activated by mast cell-derived IL-3 express retinaldehyde dehydrogenase-II and produce the immunoregulatory mediator retinoic 23 acid. *Blood* 112, 3762-3771, doi:10.1182/blood-2008-01-135251blood-2008-01-135251 [pii] (2008).

24 Fan, X. et al. Targeted disruption of Aldh1a1 (Raldh1) provides evidence for a complex mechanism of retinoic acid synthesis in the developing retina. *Mol Cell Biol* 23, 4637-4648 (2003).

25 Bowles, J. et al. Male-specific expression of Aldh1a1 in mouse and chicken fetal testes: implications for retinoid balance in gonad development. *Dev Dyn* 238, 2073-2080, doi:10.1002/dvdy.22024 (2009).

26 Levi, B. P., Yilmaz, O. H., Duester, G. & Morrison, S. J. Aldehyde dehydrogenase 1a1 is dispensable for stem cell function in the mouse hematopoietic and nervous systems. *Blood* 113, 1670-1680, doi:10.1182/blood-2008-05-156752blood-2008-05-156752 [pii] (2009).

27 Chute, J. P. et al. Inhibition of aldehyde dehydrogenase and retinoid signaling induces the expansion of human hematopoietic stem cells. *Proc Natl Acad Sci USA* 103, 11707-11712, doi:0603806103 [pii]10.1073/pnas.0603806103 (2006).

28 Cooper, T. T. et al. Inhibition of Aldehyde Dehydrogenase-Activity Expands Multipotent Myeloid Progenitor Cells with Vascular Regenerative Function. *Stem Cells* 36, 723-736, doi:10.1002/stem.2790 (2018).

29 Arnold, S. L. et al. Importance of ALDH1A enzymes in determining human testicular retinoic acid concentrations. *J Lipid Res* 56, 342-357, doi:10.1194/jlr.M054718jlr.M054718 [pii] (2015).

30 Kiefer, F. W. et al. Retinaldehyde dehydrogenase 1 regulates a thermogenic program in white adipose tissue. *Nat Med* 18, 918-925, doi:10.1038/nm.2757 nm.2757 [pii] (2012).

31 Kim, J. I. et al. Aldehyde dehydrogenase 1a1 mediates a GABA synthesis pathway in midbrain dopaminergic neurons. *Science* 350, 102-106, doi:10.1126/science.aac4690350/6256/102 [pii] (2015).

32 Ginestier, C. et al. ALDH1 is a marker of normal and malignant human mammary stem cells and a predictor of poor clinical outcome. *Cell Stem Cell* 1, 555-567, doi:10.1016/j.stem.2007.08.014S1934-5909(07)00133-6 [pii] (2007).

33 Charafe-Jauffret, E. et al. Aldehyde dehydrogenase 1-positive cancer stem cells mediate metastasis and poor clinical outcome in inflammatory breast cancer. *Clin Cancer Res* 16, 45-55, doi:10.1158/1078-0432.CCR-09-16301078-0432.CCR-09-1630 [pii] (2010).

34 Charafe-Jauffret, E. et al. Breast cancer cell lines contain functional cancer stem cells with metastatic capacity and a distinct molecular signature. *Cancer Res* 69, 1302-1313, doi:10.1158/0008-5472.CAN-08-27410008-5472.CAN-08-2741 [pii] (2009).

35 Brooks, M. D., Burness, M. L. & Wicha, M. S. Therapeutic Implications of Cellular Heterogeneity and Plasticity in Breast Cancer. *Cell Stem Cell* 17, 260-271, doi:10.1016/j.stem.2015.08.014S1934-5909(15)00369-0 [pii] (2015).

36 Marcato, P. et al. Aldehyde dehydrogenase activity of breast cancer stem cells is primarily due to isoform ALDH1A3 and its expression is predictive of metastasis. *Stem Cells* 29, 32-45, doi:10.1002/stem.563 (2011).

37 Luo, Y. et al. ALDH1A isozymes are markers of human melanoma stem cells and potential therapeutic targets. *Stem Cells* 30, 2100-2113, doi:10.1002/stem.1193 (2012).

38 Perez-Alea, M. et al. ALDH1A3 is epigenetically regulated during melanocyte transformation and is a target for melanoma treatment. *Oncogene* 36, 5695-5708, doi:10.1038/onc.2017.160onc2017160 [pii] (2017).

39 Sullivan, K. E., Rojas, K., Cerione, R. A., Nakano, I. & Wilson, K. F. The stem cell/cancer stem cell marker ALDH1A3 regulates the expression of the survival factor tissue transglutaminase, in mesenchymal glioma stem cells. *Oncotarget* 8, 22325-22343, doi:10.18632/oncotarget.1647916479 [pii] (2017).

40 Flahaut, M. et al. Aldehyde dehydrogenase activity plays a Key role in the aggressive phenotype of neuroblastoma. *BMC Cancer* 16, 781, doi:10.1186/s12885-016-2820-1 10.1186/s12885-016-2820-1 [pii] (2016).

41 Mao, P. et al. Mesenchymal glioma stem cells are maintained by activated glycolytic metabolism involving aldehyde dehydrogenase 1A3. *Proc Natl Acad Sci USA* 110, 8644-8649, doi:10.1073/pnas.1221478110 1221478110 [pii] (2013).

42 Wu, W. et al. Aldehyde dehydrogenase 1A3 (ALDH1A3) is regulated by autophagy in human glioblastoma cells. *Cancer Lett* 417, 112-123, doi:S0304-3835(18)30009-0 [pii]10.1016/j.canlet.2017.12.036 (2018).

43 Zhang, W. et al. ALDH1A3: A Marker of Mesenchymal Phenotype in Gliomas Associated with Cell Invasion. *PLoS One* 10, e0142856, doi:10.1371/journal.pone.0142856PONE-D-15-27556 [pii] (2015).

44 Cheng, P. et al. FOXD1-ALDH1A3 Signaling Is a Determinant for the Self-Renewal and Tumorigenicity of Mesenchymal Glioma Stem Cells. *Cancer Res* 76, 7219-7230, doi:0008-5472.CAN-15-2860 [pii]10.1158/0008-5472.CAN-15-2860 (2016).

45 Shao, C. et al. Essential role of aldehyde dehydrogenase 1A3 for the maintenance of non-small cell lung cancer stem cells is associated with the STAT3 pathway. *Clin Cancer Res* 20, 4154-4166, doi:10.1158/1078-0432.CCR-13-32921078-0432.CCR-13-3292 [pii] (2014).

46 Yun, X. et al. Targeting USP22 Suppresses Tumorigenicity and Enhances Cisplatin Sensitivity Through ALDH1A3 Downregulation in Cancer-Initiating Cells from Lung Adenocarcinoma. *Mol Cancer Res* 16, 1161-1171, doi:10.1158/1541-7786.MCR-18-00421541-7786.MCR-18-0042 [pii] (2018).

47 Jia, J. et al. An integrated transcriptome and epigenome analysis identifies a novel candidate gene for pancreatic cancer. *BMC Med Genomics* 6, 33, doi:10.1186/1755-8794-6-331755-8794-6-33 [pii] (2013).

48 Kim, I. G., Lee, J. H., Kim, S. Y., Kim, J. Y. & Cho, E. W. Fibulin-3 negatively regulates ALDH1 via c-MET suppression and increases gamma-radiation-induced sensitivity in some pancreatic cancer cell lines. *Biochem Biophys Res Commun* 454, 369-375, doi:10.1016/j.bbrc.2014.10.084S0006-291X(14)01893-2 [pii] (2014).

49 Golubovskaya, V. et al. Down-regulation of ALDH1A3, CD44 or MDR1 sensitizes resistant cancer cells to FAK autophosphorylation inhibitor Y15. *J Cancer Res Clin Oncol* 141, 1613-1631, doi:10.1007/s00432-015-1924-3 (2015).

50 Canino, C. et al A STAT3-NFkB/DDIT3/CEBPbeta axis modulates ALDH1A3 expression in chemoresistant cell subpopulations. *Oncotarget* 6, 12637-12653, doi:3703 [pii]10.18632/oncotarget.3703 (2015).

51 Cortes-Dericks, L., Froment, L., Boesch, R., Schmid, R. A. & Karoubi, G. Cisplatin-resistant cells in malignant pleural mesothelioma cell lines show ALDH(high)CD44 (+) phenotype and sphere-forming capacity. *BMC Cancer* 14, 304, doi:10.1186/1471-2407-14-3041471-2407-14-304 [pii] (2014).

52 di Martino, S. et al. HSP90 inhibition alters the chemotherapy-driven rearrangement of the oncogenic secretome. *Oncogene* 37, 1369-1385, doi:10.1038/s41388-017-0044-810.1038/s41388-017-0044-8 [pii] (2018).

53 Casanova-Salas, I. et al. MiR-187 Targets the Androgen-Regulated Gene ALDH1A3 in Prostate Cancer. *PLoS One* 10, e0125576, doi:10.1371/journal.pone.0125576PONE-D-14-46743 [pii] (2015).

54 Kashii-Magaribuchi, K. et al. Induced Expression of Cancer Stem Cell Markers ALDH1A3 and Sox-2 in Hierarchical Reconstitution of Apoptosis-resistant Human Breast Cancer Cells. *Acta Histochem Cytochem* 49, 149-158, doi:10.1267/ahc.16031JST.JSTAGE/ahc/16031 [pii] (2016).

55 Marcato, P. et al. Aldehyde dehydrogenase 1A3 influences breast cancer progression via differential retinoic acid signaling. *Mol Oncol* 9, 17-31, doi:10.1016/j.molonc.2014.07.010S1574-7891(14)00165-3 [pii] (2015).

56 Thomas, M. L. et al. Citral reduces breast tumor growth by inhibiting the cancer stem cell marker ALDH1A3. *Mol Oncol* 10, 1485-1496, doi:S1574-7891(16)30085-0 [pii] 10.1016/j.molonc.2016.08.004 (2016).

57 Chen, M. H. et al. ALDH1A3, the Major Aldehyde Dehydrogenase Isoform in Human Cholangiocarcinoma Cells, Affects Prognosis and Gemcitabine Resistance in Cholangiocarcinoma Patients. *Clin Cancer Res* 22, 4225-4235, doi:10.1158/1078-0432.CCR-15-18001078-0432.CCR-15-1800 [pii] (2016).

58 Zhang, W. et al. Genome-wide DNA methylation profiling identifies ALDH1A3 promoter methylation as a prognostic predictor in G-CIMP-primary glioblastoma. *Cancer Lett* 328, 120-125, doi:10.1016/j.canlet.2012.08.033 S0304-3835(12)00534-4 [pii] (2013).

59 Yang, Z. L. et al. Positive ALDH1A3 and negative GPX3 expressions are biomarkers for poor prognosis of gallbladder cancer. *Dis Markers* 35, 163-172, doi:10.1155/2013/187043 (2013).

60 Trasino, S. E., Harrison, E. H. & Wang, T. T. Androgen regulation of aldehyde dehydrogenase 1A3 (ALDH1A3) in the androgen-responsive human prostate cancer cell line LNCaP. *Exp Biol Med* (Maywood) 232, 762-771, doi:232/6/762 [pii] (2007).

61 Coyle, K. M. et al. Breast cancer subtype dictates DNA methylation and ALDH1A3-mediated expression of tumor suppressor RARRES1. *Oncotarget* 7, 44096-44112, doi:10.18632/oncotarget.9858 9858 [pii] (2016).

62 Croker, A. K. et al. Differential Functional Roles of ALDH1A1 and ALDH1A3 in Mediating Metastatic Behavior and Therapy Resistance of Human Breast Cancer Cells. *Int J Mol Sci* 18, doi:E2039 [pii]10.3390/ijms18102039 ijms18102039 [pii] (2017).

63 Shimamura, M., Kurashige, T., Mitsutake, N. & Nagayama, Y. Aldehyde dehydrogenase activity plays no functional role in stem cell-like properties in anaplastic thyroid cancer cell lines. Endocrine 55, 934-943, doi:10.1007/s12020-016-1224-y10.1007/s12020-016-1224-y [pii] (2017).

64 Moreb, J. S. et al. ALDH isozymes downregulation affects cell growth, cell motility and gene expression in lung cancer cells. *Mol Cancer* 7, 87, doi:10.1186/1476-4598-7-87 1476-4598-7-87 [pii] (2008).

65 Moreb, J. S. et al. The enzymatic activity of human aldehyde dehydrogenases 1A2 and 2 (ALDH1A2 and ALDH2) is detected by Aldefluor, inhibited by diethylaminobenzaldehyde and has significant effects on cell proliferation and drug resistance. *Chem Biol Interact* 195, 52-60, doi:10.1016/j.cbi.2011.10.007S0009-2797(11)00311-5 [pii] (2012).

Liu, Y. et al. ALDH1A1 mRNA expression in association with prognosis of triple-negative breast cancer. *Oncotarget* 6, 41360-41369, doi:10.18632/oncotarget.6023 6023 [pii] (2015).

67 Tomita, H., Tanaka, K., Tanaka, T. & Hara, A. Aldehyde dehydrogenase 1A1 in stem cells and cancer. *Oncotarget* 7, 11018-11032, doi:10.18632/oncotarget.6920 6920 [pii] (2016).

68 Koppaka, V. et al. Aldehyde dehydrogenase inhibitors: a comprehensive review of the pharmacology, mechanism of action, substrate specificity, and clinical application. *Pharmacol Rev* 64, 520-539, doi:10.1124/pr.111.005538 pr.111.005538 [pii] (2012).

69 Yasgar, A. et al. A High-Content Assay Enables the Automated Screening and Identification of Small Molecules with Specific ALDH1A1-Inhibitory Activity. *PLoS One* 12, e0170937, doi:10.1371/journal.pone.0170937 PONE-D-16-39942 [pii] (2017).

70 Gibb, Z., Lambourne, S. R., Curry, B. J., Hall, S. E. & Aitken, R. J. Aldehyde Dehydrogenase Plays a Pivotal Role in the Maintenance of Stallion Sperm Motility. *Biol Reprod* 94, 133, doi:10.1095/biolreprod.116.140509 biolreprod.116.140509 [pii] (2016).

71 Kurth, I. et al. Cancer stem cell related markers of radioresistance in head and neck squamous cell carcinoma. *Oncotarget* 6, 34494-34509, doi:10.18632/oncotarget.5417 5417 [pii] (2015).

72 Piskounova, E. et al. Oxidative stress inhibits distant metastasis by human melanoma cells. *Nature* 527, 186-191, doi:10.1038/nature15726nature15726 [pii] (2015).

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A compound represented by one of the following structural formulas:

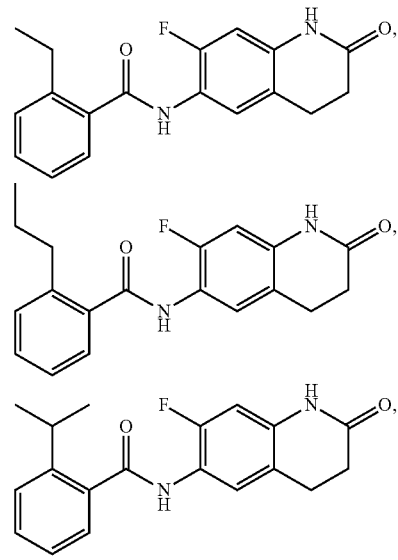

-continued
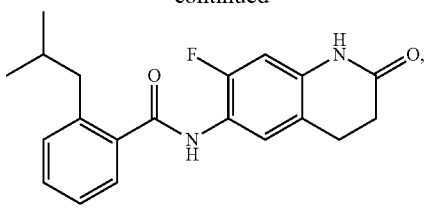
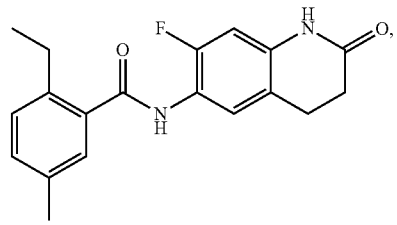
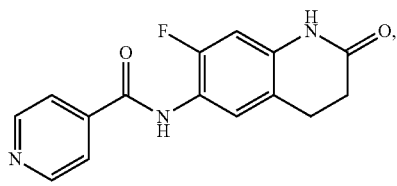
-continued
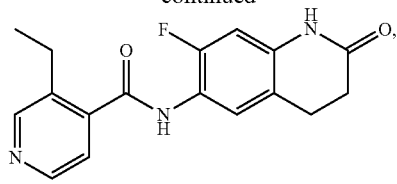
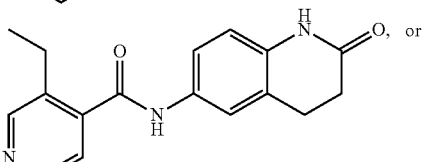
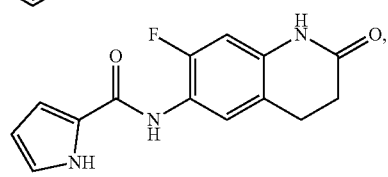
or a pharmaceutically acceptable salt thereof.
2. A composition comprising a compound of claim 1, or a pharmaceutically acceptable salt thereof, and a pharmaceutically acceptable carrier or excipient.
* * * * *